(12) United States Patent
Rikihisa et al.

(10) Patent No.: US 7,888,491 B2
(45) Date of Patent: *Feb. 15, 2011

(54) **OUTER MEMBRANE PROTEIN OF *EHRLICHIA CANIS* AND *EHRLICHIA CHAFFEENSIS***

(75) Inventors: Yasuko Rikihisa, Worthington, OH (US); Norio Ohashi, Columbus, OH (US)

(73) Assignee: The Ohio State University Research Foundation, Columbus, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/901,714

(22) Filed: Jul. 29, 2004

(65) Prior Publication Data

US 2004/0265333 A1 Dec. 30, 2004

Related U.S. Application Data

(62) Division of application No. 10/314,639, filed on Dec. 9, 2002, now Pat. No. 6,893,640, which is a division of application No. 09/314,701, filed on May 19, 1999, now Pat. No. 6,544,517.

(60) Provisional application No. 60/100,843, filed on Sep. 18, 1998.

(51) Int. Cl.
C07H 21/04 (2006.01)
A61K 39/12 (2006.01)
A61K 39/02 (2006.01)

(52) U.S. Cl. ............... 536/23.7; 536/23.32; 536/23.33; 530/300; 530/350; 435/243; 424/184.1; 424/185.1; 424/190.1; 424/191.1; 424/234.1

(58) Field of Classification Search ............... 424/184.1, 424/185.1, 190.1, 191.1, 234.1; 435/243; 530/300, 350; 536/23.7, 23.32, 23.33
See application file for complete search history.

(56) References Cited

U.S. PATENT DOCUMENTS

| | | | |
|---|---|---|---|
| 4,478,914 | A | 10/1984 | Giese |
| 5,401,656 | A | 3/1995 | Dawson |
| 5,413,931 | A | 5/1995 | Dawson et al. |
| 5,789,176 | A | 8/1998 | Dawson et al. |
| 5,869,335 | A | 2/1999 | Munderloh et al. |
| 6,025,338 | A | 2/2000 | Barbet et al. |
| 6,231,869 | B1 | 5/2001 | Reed et al. |
| 6,392,023 | B1 | 5/2002 | Walker et al. |
| 6,432,649 | B1 | 8/2002 | Stich et al. |
| 6,544,517 | B1 | 4/2003 | Rikihisa et al. |
| 6,893,640 | B2 | 5/2005 | Rikihisa et al. |
| 6,923,963 | B2 * | 8/2005 | Rikihisa et al. .......... 424/184.1 |
| 7,063,846 | B2 | 6/2006 | Rikihisa et al. |

FOREIGN PATENT DOCUMENTS

| | | |
|---|---|---|
| WO | 98/16554 | 4/1998 |
| WO | WO 98/16554 | 4/1998 |
| WO | WO 99/13720 | 3/1999 |
| WO | WO 00/32745 | 6/2000 |

OTHER PUBLICATIONS

Brouqui et al., "Antigenic characterization of Ehrlichiae: protein immunoblotting of *Ehrlichia canis*, *Ehrlichia sennetsu*, and *Ehrlichia risticii*,", *J. Clin. Microbiol.* (1992) vol. 30, No. 5, pp. 1062-1066. Abstract Only.

Brouqui et al., "Serologic diagnosis of human monocytic ehrlichiosis by immunoblot analysis", *Clin. Diagn. Lab. Immunol.* (1994) vol. 1, No. 6, pp. 645-649. Abstract Only.

Chen et al., "Analysis and untrastructural localization of *Ehrlichia chaffeensis* proteins with monoclonal antibodies", *The American Journal of Tropical Medicine and Hygiene* (1996) vol. 54, No. 4, pp. 405-412. Abstract Only.

Chen et al., "Identification of the antigenic constituents of *Ehrlichia chaffeensis*", *Am. J. Trp. Med. Hyg.* (1994) vol. 50, No. 1, pp. 52-28. Abstract Only.

Chen et al., "Western Immonublotting analysis of the antibody responses of patients with human monocytotropic ehrlichiosis to different strains of *Ehrlichia chaffeensis* and *Ehrlichia canis*", *Clin. Diagn. Labl. Immunol.* (1997) vol. 4, No. 6, pp. 731-735. Abstract Only.

Dawson et al., "The interface between research and the diagnoses of an emerging tick-borne disease, human ehrlichiosis due to *Ehrlichia chaffeensis*", *Archives of Journal of Medicine* (1996) vol. 156, No. 2, p. 137 (6).

(Continued)

*Primary Examiner*—Rodney P. Swartz
(74) *Attorney, Agent, or Firm*—Calfee, Halter & Griswold LLP

(57) ABSTRACT

Diagnostic tools for for serodiagnosing ehrlichiosis in mammals, particularly in members of the Canidae family and in humans are provided. The diagnostic tools are a group of outer membrane proteins of *E. chaffeensis* and variants thereof, referred to hereinafter as the "OMP proteins", a group of outer membrane proteins of *E. canis* and variants thereof referred to hereinafter as the "P30F proteins", and antibodies to the OMP proteins and the P30F proteins. The OMP proteins of *E. chaffeensis* encompass OMP-1, OMP-1A, OMP1-B, OMP-1C, OMP1-D, OMP1-E, OMP1-F, OMP1-H, OMP-1R, OMP-1S, OMP-1T, OMP-1U, OMP-1V, OMP-1W, OMP-1X, OMP-1Y and OMP-1Z. The P30F proteins of *E. canis* encompass P30, P30a, P30-1, P30-2, P30-3, P304, P30-5, P30-6, P30-7, P30-8, P30-9, P30-10, P30-11, and P30-12. Isolated polynucleotides that encode the *E. chaffeensis* OMP proteins and isolated polynucleotides that encode the *E. canis* P30F protein are also provided. The present invention also relates to kits containing reagents for diagnosing human ehrlichiosis and canine ehrlichiosis, and to immunogenic compositions containing one or more OMP proteins or P30F proteins.

32 Claims, 64 Drawing Sheets

OTHER PUBLICATIONS

Felek et al., "Transcriptional Analysis of p30 Major Outer Membrane Protein Genes of *Ehrlichia canis* in Naturally Infected Ticks and Sequence Analysis of p30-10 of *E. canis* from Diverse Geographic Regions", *Journal of Clinical Microbiology* (2003) vol. 41, No. 2, pp. 886-888.
GenBank Accession AF021338, Feb. 19, 1998.
GenBank Accession AF062761, Jul. 19, 1998.
GenBank Accession AF068234, Jun. 8, 1998.
GenBank Accession AF077732, Aug. 13, 1998.
GenBank Accession AF077733, Aug. 13, 1998.
GenBank Accession AF077734, Aug. 13, 1998.
GenBank Accession AF077735, Aug. 13, 1998.
GenBank Accession AF078553, Oct. 27, 1998.
GenBank Accession AF078554, Oct. 27, 1998.
GenBank Accession AF078555, Oct. 27, 1998.
GenBank Accession AF082745, Oct. 20, 1998.
GenBank Accession AF082746, Oct. 20, 1998.
GenBank Accession AF082747, Oct. 20, 1998.
GenBank Accession AF082748, Oct. 20, 1998.
GenBank Accession AF082749, Oct. 20, 1998.
GenBank Accession AF082750, Oct. 20, 1998.
GenBank Accession L01987, Mar. 17, 1994.
GenBank Accession No. AF125274.
GenBank Accession No. AF125275.
GenBank Accession No. AF125276.
GenBank Accession No. AF125277.
GenBank Accession No. AF125278.
GenBank Accession No. AF125279.
GenBank Accession U07862, Jan. 5, 1995.
GenBank Accession U36193, Aug. 8, 1996.
GenBank Accession U50830, Jul. 15, 1996.
GenBank Accession U50831, Jul. 15, 1996.
GenBank Accession U50832, Jul. 15, 1996.
GenBank Accession U50833, Jul. 15, 1996.
GenBank Accession U50834, Jul. 15, 1996.
GenBank Accession U50835, Jul. 15, 1996.
GenBank Accession U72291, Feb. 19, 1998.
GenBank Accession X74250, Oct. 10, 1994.
Kelly et al., "Serological evidence for antigenic relationships between *Ehrlichia canis* and *Cowdria ruminatium*", *Res. Vet. Sci.* (1994) vol. 56, No. 2, pp. 170-174. Abstract Only.
McBride et al., "Molecular characterization of a new 28-kilodalton protein gene and a multigene locus enclding five homologous 28-kilodalton immunodominant outer member proteins of *Ehrlichia canis*", *Rickettsiae and rickettsial diseases at the turn of the third millenium*, D. Raoult, P. Brouqul, Editors, Elsevier, Paris, Jun. 1999, pp. 43-47.
McBride et al., "Molecular Cloning of the Gene for a Conserved Major Innumoreactive 28-Kilodalton Protein of *Ehrlichia canis*: a Potential Serodiagnostic Antigen", *Clinical and Diagnostic Laboratory Immunology* (1999) vol. 6, No. 3, pp. 392-399.
Oberle et al., "Derivation of the complete *msp4* gene sequence of *Anaplasma marginale* without cloning", *Gene* (1993) vol. 136, pp. 291-294.
Ohashi et al., "Characterization of *p30* Multigene Family of *Ehrlichia canis*", Abstract D/B-126, Ninety-ninth General Meeting of the American Society for Microbiology, Chicago, IL, May 30-Jun. 3, 1999, p. 233.
Ohashi et al., "Cloning and Characterization of Multigenes Enclding the Immunodominant 30-Kilodalton Major Outer Membrane Proteins of *Ehrlichia canis* and Application of the Recombinant Protein for Serodiagnosis", *Journal of Clinical Microbiology* (1998) vol. 36, No. 9, pp. 2671-2680.
Ohashi et al., "Cloning, Sequencing, and Overexpression of *Ehrlichia canis* Immunoreactive Protein Gene Homologous to Members of *eEhrlichia chaffeensis omp-1* Gene Family", Abstract D-28, 98th General Meeting of the American Society for Microbiology, Atlanta, GA, May 17-21, 1998.
Ohashi et al., "Immunodominant Major Outer Membrane Protein of *Ehrlichia chaffeensis* Are Encoded by a Polymorphic Multigene Family", *Infection and Immunity* (1998) vol. 66, No. 1, pp. 132-139.

Ohashi et al., "Immunoprotective 28-kDa outer membrane protein of *Ehrlichia chafeensis* is a member of multi-sized protein antigen family", Abstract D-80, 97th General Meeting of the American Society for Microbiology, Miami Beach, FL, May 4-8, 1997.
Reddy et al, "Molecular Characterization of a 28 kDa Surface Antigen Family of the Tribe *Ehrlichiae*", *Biochemical and Biophysical Research Communications* (1998) vol. 247, No. 3, pp. 636-643.
Reddy et al., "Sequence Heterogeneity of the Major Antigen Protein 1 Genes from *Cowdria ruminantium* Isolates from Different Geographical Areas", *Clinical and Diagnostic Laboratory Immunology* (1996) vol. 1376, No. 4, pp. 417-422.
Rikihisa et al., "E: Enzyme-Linked Immunosorbent Assay and Western Immunoblot Analyses of *Ehrlichia canis* and a Canine Granulogytic *Ehrlichia* Infection", *Journal of Clinical Microbiology* (1992) vol. 20, No. 2, pp. 143-148. Abstract Only.
Sulsona et al., "The *map1* Gene of *Cowdria ruminantium* is a Menber of a Multigene Family Containing Both Conserved and Variable Genes", *Biochemical and Biophysical Research Communications* (1999), vol. 257, pp. 300-305.
Unver et al., "Transcriptional Analysis of p30 Major Outer Membrane Multigene Family of *Ehrlichia canis* in Dogs, Ticks, and Cell Culture at Different Temperatures", *Infection and Immunity* (2001) vol. 69, No. 10, pp. 6172-6178.
Unver et al., "Dot Immunoblot Assay for Canine Ehrlichiosis: Using Recombinant Major Protein Antigen of *Ehrlichia canis*", Abstract D-29, 98th General Meeting of the American Society for Microbiology, Atlanta, GA, May 17-21, 1998.
Unver et al., "Western and Dot Blotting Analysis of *Ehrlichia chaffeensi*-IFA Positive and—Negative Human Sera Using Native and Recombinant *E. chaffeensis* and *E. canis* Antigen", Abstract D/B-138, Ninety-ninth General Meeting of the American Society for Microbiology, Chicago, IL, May 30-Jun. 3, 1999, p. 236.
Van Vliet et al., "Molecular Cloning, Sequence Analysis and Expression of the Gene Encoding the Immunodominant 32-Kilodalton Protein of *Cowdria ruminantium*", *Infection and Immunity* (1994) vol. 62, No. 4, pp. 1451-1456.
Yu et al., "Characterization of the genus-common outer member proteins in *Ehrlichia*", *Rickettsiae and rickettsial diseases at the turn of the third millenium*, D. Raoult, P. Brouqui, Editors, Elsevier, Paris, Jun. 1999, pp. 103-107.
Yu et al., "Comparison of *Ehrlichia chaffeensis* Recombinant Proteins for Serologic Diagnosis of Human Monocytotropic Ehrlichiosis", *Journal of Clinical Microbiology* (1999) vol. 37, No. 8, pp. 2568-2575.
Yu et al., "Genetic Diversity of the 28-Kilodalton Outer Membrane Protein gene in Human Isolates of *Ehrlichia chaffeensis*", *Journal of Clinical Microbiology* (1999), vol. 37, No. 4, pp. 1177-1143.
Yu et al., "Sequence and characterization of an *Erlichia chaffeensis* gene encoding 314 amino acids high homologous to the NAD A enzyme", *FEMS Microbiol. Lett.* (1197) vol. 154, No. 1, pp. 53-58. Abstract Only.
Zhang et al., "Binding of Outer Membrane Proteins of *Ehrlichia chaffeensis* to DHB2 Cells", Abstract D-79, 97th General Meeting of the American Society for Microbiology, Miami Beach, FL, May 4-8, 1997.
"Cloning and Characterization of Multigenes Encoding the Immunodominant 30-Kilodalton Major Outer Membrane Proteins of *Ehrlichia canis* and Application of the Recombinant Protein for Serodiagnosis" by Ohashi, et al., *Journal of Clinical Microbiology*, vol. 36, No. 9, Sep. 1998, pp. 2671-2680.
"Immunodominant Major Outer Membrane Protein of *Ehrlichia chaffeensis* Are Encoded by a Polymorphic Multigene Family" by Ohashi, et al., *Infection and Immunity*, vol. 66, No. 1, Jan. 1998, pp. 132-139.
Abstract D-79, "Binding of Outer Membrane Proteins of *Ehrlichia chaffeensis* to DHB2 Cells" by Zhang, et al., 97th General Meeting of the American Society for Microbiology, Miami Beach, Florida, May 4-8, 1997.
Abstract D-80, "Immunoprotective 28-kDa outer membrane protein of *Ehrlichia chaffeensis* is a member Of multi-sized protein antigen family" by Ohashi, et al., 97th General Meeting of the American Society for Microbiology, Miami Beach, Florida, May 408, 1997.

Abstract D-28, "Cloning, Sequencing, and Overexpression of *Ehrlichia canis* Immunoreactive Protein Gene Homologous to Members of *Ehrlichia chaffeensis omp-1* Gene Family" by Ohashi, et al., 98th General Meeting of the American Society for Microbiology, May 17-2, 1998, Atlanta, Georgia.

Abstract D-29, "Dot Immunoblot Assay for Canine Ehrlichiosis: Using Recombinant Major Protein Antigen of *Ehrlichia canis*" by Unver, et al., 98th General Meeting of the American Society for Microbiology, May 17-21, 1998, Atlanta, Georgia.

"Molecular Characterization of a 28 kDa Surface Antigen Family of the Tribe *Ehrlichiae*" by G. Reddy, et al. *Biochemical and Biophysical Research Communications*, vol. 247, No. 3, 1998, pp. 636-643.

"Sequence Heterogeneity of the Major Antigen Protein 1 Genes from *Cowdria ruminantium* Isolates from Different Geographical Areas" by G. Reddy, et al., *Clinical and Diagnostic Laboratory Immunology*, vol. 3, No. 4, Jul. 1996, pp. 417-422.

"Derivation of the complete *msp4* gene sequence of *Anaplasma marginale* without cloning" by Oberle, et al., *Gene*, vol. 136, Dec. 1993, pp. 291-294.

"Molecular Cloning, Sequence Analysis and Expression of the Gene Encoding the Immunodominant 32-Kilodalton Protein of *Cowdria ruminantium*" by van Vliet, et al., *Infection and Immunity*, vol. 62, No. 4, Apr. 1994, pp. 1451-1456.

"Sequence and characterization of an *Ehrlichia chaffeensis* gene encoding 314 amino acids highly homologous to the NAD A enzyme" by Yu, et al., *FEMS Microbiol Lett*, Sep. 1, 1997, 154 (1), pp. 53-58.

"E: Enzyme-Linked Immunosorbent Assay and Western Immunoblot Analyses of *Ehrlichia canis* and a Canine Granulocytic *Ehrlichia* Infection" by Rikihisa, et al., *Journal of Clinical Microbiology*, vol. 20, No. 2, Jan. 1992, pp. 143-148.

"Serological evidence for antigenic relationships between *Ehrlichia canis* and *Cowdria ruminatium*" by Kelly, et al., *Res Vet Sci*, 56 (2), Mar. 1994, pp. 170-174.

"The interface between research and the diagnoses of an emerging tick-borne disease, human ehrlichiosis due to *Ehrlichia chaffeensis*" by Dawson, et al., *Archives of Journal of Medicine*, vol. 156, No. 2, Jan. 22, 1996, pp. 137 (6).

"Western Immunoblotting analysis of the antibody response of patients with human monocytotropic ehrlichiosis to different strains of *Ehrlichia chaffeensis* and *Ehrlichia canis*" by Chen, et al., *Clin Diagn Lab Immunol*, Nov. 1997, 4 (6), pp. 731-735.

"Analysis and untrastructural localization of *Ehrlichia chaffeensis* proteins with monoclonal antibodies" by Chen, et al, *The American Journal of Tropical Medicine and Hygiene*, 1996, 54 (4) pp. 405-412.

"Identification of the antigenic constituents of *Ehrlichia chaffeensis*"by Chen, et al., *Am J Trp Med Hyg* Jan. 1994, 50 (1) pp. 52-58.

"Antigenic characterization of *Ehrlichiae*: protein immunoblotting of *Ehrlichia canis*, *Ehrlichia sennetsu*, and *Ehrlichia risticii*" by Brouqui, et al., *J Clin Microbiol*, May 1992, 30 (5) pp. 1062-1066.

"Serologic diagnosis of human monocytic ehrlichiosis by immunoblot analysis" by Brouqui, et al., *Clin Diagn Lab Immunol*, Nov. 1994, 1 (6) pp. 645-649.

Abstract D/B-126, "Characterization of *p30* Multigene Family of *Ehrlichia canis*" by Ohashi, et al., Ninety-ninth General Meeting of the American Society for Microbiology, May 30-Jun. 3, 1999, Chicago, Illinois, p. 233.

Abstract D/B-138, "Western and Dot Blotting Analysis of *Ehrlichia chaffeensi*-IFA Positive and -Negative Human Sera Using Native and Recombinant *E. chaffeensis* and *E. canis* Antigen" by Unver, et al., Ninety-ninth General Meeting of the American Society for Microbiology, May 30-Jun. 3, 1999, Chicago, Illinois, p. 236.

"Molecular Cloning of the Gene for a Conserved Major Innumoreactive 28-Kilodalton Protein of *Ehrlichia canis*: a Potential Serodiagnostic Antigen" by McBride, et al., *Clinical and Diagnostic Laboratory Immunology*, vol. 6, No. 3, May 1999, pp. 392-399.

"The *mag1* Gene of a *Cowdria ruminantium* is a Member of a Multigene Family Containing Both Conserved and Variable Genes" by Sulsona, et al., *Biochemical and Biophysical Research Communications*, 257, 300-305 (1999).

"Comparison of *Ehrlichia chaffeensis* Recombinant Proteins for Serologic Diagnosis of Human Monocytotropic Ehrlichiosis" by Yu, et al., *Journal of Clinical Microbiology*, vol. 37, No. 8, Aug. 1999, p. 2568-2575.

"Genetic Diversity of the 28-Kilodalton Outer Membrane Protein Gene in Human Isolates of *Ehrlichia chaffeensis*" by Yu, et al., *Journal of Clinical Microbiology*, vol. 37, No. 4, Apr. 1999, pp. 1137-1143.

"Molecular characterization of a new 28-kilodalton protein gene and a multigene locus encoding five homologous 28-kilodalton immunodominant outer membrane proteins of *Ehrlichia canis*" by McBride, et al., *Rickettsiae and rickettsial diseases at the turn of thethird millenium*, D. Raoult, P. Brouqui, eds., Elsevier, Paris, Jun. 1999, pp. 43-47.

"Characterization of the genus-common outer membrane proteins in *Ehrlichia*" by Yu, et al., *Rickettsiae and rickettsial diseases at the turn of the third millenium*, D. Raoult, P. Brouqui, eds., Elsevier, Paris, Jun. 1999, pp. 103-107.

"Transcriptional Analysis of p30 Major Outer Membrane Multigene Family of *Ehrlichia canis* in Dogs, Ticks, and Cell Celture at Different Temperatures" by Unver et al., *Infection and Immunity*, vol. 69, No. 10, Oct. 2001, pp. 6172-6178.

"Transcriptional Analysis of p30 Major Outer Membrane Protein Genes of *Ehrlichia canis* in Naturally Infected Ticks and Sequence Analysis of p30-10 of *E.canis* from Diverse Geographic Regions" by Felek et al., *Journal of Clinical Microbiology*, vol. 41, No. 2, Feb. 2003, pp. 886-888.

"Detection of *Ehrlichia chaffeensis* in Human Tissue by Using a Species-Specific Monoclonal Antibody", p. 3284-3288, Journal of Clinical Microbiology, Dec. 1993.

"Cloning and Sequencing of the gene for a 120-kDa immunodominant protein of *Ehrlichia chaffeensis*", Xue-Jie Yu et al., Gene 184 (1997) 149-154.

Office action in related U.S. patent application "Methods for detecting *Ehrlichia canis* and *Ehrlichia chaffeensis* in vertebrate and invertebrate hosts", U.S. Appl. No. 09/648,520, filed Aug. 25, 2000, now U.S. Patent No. 6,432,649, office action dated Jul. 18, 2001.

European search report dated Feb. 21, 2005 in connection with EP appl. No. 98949384.6.

International Search Report in connection with PCT appl. No. PCT/US98/19600, dated Feb. 25, 1999—WO 99/13720.

U.S. Appl. No. 09/157,132, filed Sep. 18, 1998 (abandoned).

Alleman et al., "*Anaplasma marginale* major surface protein 3 is encoded by a polymorphic, multigene family," Infect. Immun. 65: 156-163 (1997).

Altschul et al., "Basic local alignment search tool," J. Mol. Biol. 215: 403-410 (1990).

Anderson et al., "*Ehrlichia chaffeensis*, a new species associated with human ehrlichiaosis," J. Clin. Microbiol. 29: 2838-2842 (1991).

Anderson et al., "Detection of the etiologic agent of human ehrlichiosis by polymerase chain reaction," J. Clin. Microbiol. 30: 775-780 (1992).

Barbet, AF, "Recent developments in the molecular biology of anaplasmosis", Vet. Parasitol. 57: 43-49 (1995).

Barbour, "Linear DNA of *Borrelia* species and antigenic variation," Trends Microbiol. 1: 236-239 (1993).

Caldwell, et al., "Purification of Partial characterization of the major outer membrane protein *Chlamydia trachomatis*," Infect. Immun. 31: 1161-1176 (1981).

Chen et al., "Antigenic diversity among strains of *Ehrlichia chaffeensis*," In Proceedings of the Vth International Symposium of Rickettsiae and Rickettsial Diseases, Stara Lesna, Slovak Academy of Sciences 329-334: (J. Kasar, R. Toman, editors, Batislava, Slovak Republic, Sep. 1-6, 1996).

Chen et al., "Genetic and antigenic diversity of *Ehrlichia chaffeensis*: comparative analysis of a novel human strain from Oklahoma and previously isolated strains," J. Infect. Dis. 175: 856-863 (1997).

Chopra, et al., "Lysozyme-promoted association of protein I molecules in the outer membrane of *Escherichia coli*," J. Bacteriol. 132: 411-418 (1977).

Dame et al., "Phylogenetic relationship of *Cowdria ruminantium* agent of heartwater, to *Anaplasma marginale* and other members of the order Rickettsiales determined on the basis of 16S rRNA," Int. J. Syst. Bacteriol. 42: 270-274 (1992).

Dawson et al., "Serological diagnosis of human ehrlichiosis using two *Ehrlichia canis* isolates," J. Infect. Dis. 163: 564-567 (1991).

Dayoff et al., In Atlas of Protein Sequence and Structure 345-362 (M.O. Dayoff, editor, National BioMed Research Foundation, Washington D.C., vol. 5, Supplement 3, 1978).

Dumler et al., "Human ehrlichiosis: hematopathology and immunohistologic detection of *Ehrlichia chaffeensis*," Hum. Pathol. 24: 391-396 (1993).

Dumler et al "Isolation and characterization of a new strain of *Ehrlichia chaffeensis* from a patient with nearly fatal monocytic ehrlichiosis" J Clin Microbiol 33:1704-11 1995.

Eid et al., "Expression of a major surface protein 2 antigenic variants during acute *Anaplasma marginale* rickettsemia," Infect. Immun. 64: 836-841 (1996).

Eng et al., "Epidemiologic, clinical, and laboratory findings of human ehrlichiosis in the United States, 1988." JAMA 264: 2251-2258 (1990).

Felsenstein, "PHYLIP-phylogeny inference package (version 3.3)," Cladistics 5:164-166 (1989).

Filip et al., "Solubilization of the cytoplasmic Membrane of *Escherichia coli* by the ionic detergent sodium-lauryl sarcosinate," J. Bacteriol. 115: 717-722 (1973).

GenBank Accession AF082744, Sep. 18, 2000.

Haas et al., "The repertoire of silent pilus genes in *Neisseria gonorrhoeae*: evidence for gene conversion," Cell 44: 107-115 (1986).

Ijdo, JW et al "Cloning of the gene encoding the 44-kilodalton antigen of the agent of human granulocytic ehrlichiosis and characterization of the humoral response", Infection and Immunity, p. 3264-3269 (Jul. 1998).

Iqbal et al., "Reisolation of *Ehrlichia canis* from blood and tissues of dogs after treatment with doxycycline treatment," J. Clin. Microbiol. 32: 1644-1649 (1994).

Iqbal et al., "Comparison of PCR with other tests for early diagnosis of canine ehrlichiosis," J. Clin. Microbiol. 32: 1658-1662 (1994).

Iqbal et al., "Application of polymerase chain reaction for detection of *Ehrlichia canis* in tissues of dogs," Vet. Microbiol. 42: 281-287 (1994).

Khan et al., "A Method for quantitation of Protein in the Presence of Percoll", Anal. Biochem. 117: 108-112 (1981).

Kim et al, "Characterization of monoclonal antibodies to the 44-kilodalton major outer membrane protein of the human granulocytic ehrlichiosis agent", J. of Clinical Microbiology, pp. 3278-3284 (Nov. 1998).

Koehler, et al., "Overexpression and surface localization of the *Chlamydia trachomatis* major outer membrane protein in *Escherichia coli*", Mol. Microbiol. 6: 1087-1094 (1992).

Maeda et al., "Human infection with *Ehrlichia canis*, a leukocytic rickettsia," N. Engl. J. Med. 316: 853-856 (1987).

Mahan et al., "An immunoblotting diagnostic assay for heartwater based on the immunodominant 32-kilodalton protein of *Cowdria ruminantium* detects false positive in the field sera," J. Clin. Microbiol. 31: 2729-2737 (1993).

Kelly et al., "Serological evidence for antigenic relationships between *Ehrlichia canis* and *Cowdria ruminatium*," Res. Vet. Sci. 56 (2): 170-174 (1994).

Matthewman, LA et al "Reactivity of sera collected from dogs in Mutare, Zimbabwe, to antigens of *Ehrlichia canis* and *Cowdria ruminantium*" Vet Rec 134:19, 498-499, May 7, 1994.

McBride et al. "A conserved, transcription ally active p28 multigene locus of *Ehrlichia canis*," Gene 254 (1-2): 245-252 (2000).

Murphy CI et al "Major antigenic proteins of the agent of human granulocytic ehrlichiosis are encoded by members of a multigene family" Infect and Immunity pp. 3711-3718, Aug. 1998.

Needleman et al. "A General Method Applicable to the Search for Similarities in the Amino Acid Sequence of Two Proteins" J. Mol. Bio. 48:443-453 (1970).

Ohashi et al., "Purification and partial characterization of a type-specific antigen of *Rickettsia tsutsugamushi*," Infect. Immun. 57: 1427-1431 (1989).

Ohashi et al., "Diversity of immunodominant 56-kDa type-specific antigen (TSA) of *Rickettsia tsutsugamushi*: Sequence and comparative analyses of the gene encoding TSA homologues from four antigenic variants," J. Biol. Chem. 267: 12728-12735 (1992).

Ohashi et al., "Demonstration of Antigenic and Genotypic Variation in *Orientia tsutsugamushi* which were isolated in Japan, and their classificaiton into type and subtype" Microbiol. Immunol., 40 (9), 627-638, (1996).

Ohashi et al., "Analysis of transcriptionally active gene clusters of major outer membrane protein multigene family in *Ehrlichia canis* and *E. chaffeensis*", Infection and Immunity, 2083-2091, 2001.

Oliver, "Protein secretion in *Escherichia coli*," Annu. Rev. Microbiol. 39: 615-648 (1985).

Palmer er al., "The immunoprotective *Anaplasma marginale* major surface protein 2 is encoded by a polymorphic multigene family," Infect. Immun. 62: 3808-3816 (1994).

Perez et al., "*Ehrlichia canis*-like agent isolated from a man in Venezuela: Antigenic and Genetic characterization", J. Clin. Microbiol. 34: 2133-2139 (1996).

Pretzman et al., "Enzyme-linked immunosorbent assay for Potomac horse fever disease," J. Clin. Microbiol. 25: 31-36 (1987).

Pretzman et al "16S rRNA Gene Sequence of *Neorickettsia helminthoeca* and Its Phylogenetic Alignment with Members of the Genus *Ehrlichia*" Int J Syst Bacteriol 45: 315-318 1995.

Reddy, G. Roman, et al., "A Family of 28 kDa Variant Surface Antigen Genes of the tribe *Ehrlichiae*: Does it Play a role in immune evasion?" Abstract, Annual Meeting of ASRRD Sep. 23, 1997.

Rikihisa et al "Clinical histopathological and immunological responses of ponies to *Ehrlichia sennetsu* and subsequent *Ehrlichia risticii* challenge" Infect Immun 56: 2960-66 1988.

Rikihisa, "Ultrastructure of rickettsiae with special emphasis on *Ehrlichia*. Ehrlichiosis: A vectorborne Disease of Animals and Humans," In Current Topics in Veterinary Medicine and Animal Sciences 54: 22-31 (Williams and Kakoma, Editors, Kluwer Publishing Co., Norwell, MA 1990).

Rikihisa, "The tribe *Ehrlichieae* and ehrlichial diseases," Clin. Microbiol. Rev. 4: 286-308 (1991).

Rikihisa "Cross-reacting antigens between *Neorickettsia helminthoeca* and *Ehrlichia* species shown by immunofluorescence and Western immunoblotting" J Clin Microbiol 29: 2024-2029 (1991).

Rikihisa et al., "Analyses of *Ehrlichia canis* and Canine Granulocytic *Ehrlichia* Infection," Journal of Clinical Microbiology 30: 143-148 (1992).

Rikihisa et al., "C reactive protein and a1-acidglyco protein concentrations in dogs infected with *Ehrlichia canis*," J. Clin. Microbiol. 32: 912-917 (1994).

Rikihisa et al., "Western immunoblot analysis of *Ehrlichia chaffeensis*, *E. canis*, or *E. ewingii* infection of dogs and humans," J. Clin. Microbiol. 32: 2107-2112 (1994).

Rikihisa et al., "Inhibition of infection of macrophages with *Ehrlichia risticii* by cytochalasins, monodansylcadaverine and taxol.," Infect. Immun. 62: 5126-5132 (1994).

Rikihisa, "Ehrlichial Diseases in Zoonotic Diseases," Clin. Microbiol. 2: 413-419 (1995) and English translation.

Rikihisa et al., Ultrastructural and Antigenic characterization of a granulocytic ehrlichiosis agent directly isolated and stably cultivated from a patient in New York State J. Infect. Dis. 175: 210-213 (1997).

Rikihisa, "*Ehrlichiae* (Plenary Session)," In Proceedings of the 5th International Symposium on Rickettsiae and Rickettsial Diseases 272-286 (Slovak Academy of Sciences, Bratislava, Slovak Republic: International Society of Rickettsiae and Rickettsial Diseases 1996).

Rikihisa et al., "Clinical and biological aspects of infections caused by *Ehrlichia chaffeensis*," Microb. Infect. 1: 367-376 (Jun. 1999).

Rikihisa et al., "*Ehrlichiae* of Veterinary Importance," In Rickettsiae and rickettsial diseases at the turn of the third millenium, 393-405 (D. Raoult, P. Brouqui, Editors, Elsevier, Paris, Jun. 1999).

Storey JR et al "Molecular Cloning and sequencing of three granulocytic *Ehrlichia* genes encoding high-molecular-weight immunoreactive proteins" Infec and Immun 1356-66 Apr. 1998.

Su et al., "*Chlamydia trachomatis*-host cell interactions: role of the chlamydial major outer membrane protein as an adhesin," Infect. Immun. 58: 1017-1025 (1990).

Sumner et al., "*Ehrlichia chaffeensis* expresses an immunoreactive protein homologous to the *Escherichia coli* GroEL protein," Infect. Immun. 61: 3536-3539 (1993).

Van Vliet et al., "Phylogenetic position of *Cowdria ruminatium* (rickettsiales) determined by analysis of amplified 16S ribosomal DNA sequences", Int. J. Syst. Bacteriol. 42: 494-498 (1992).

Verstreate, et al., "Outer membrane proteins of *Brucella abortus*: isolation and characterization," Infect. Immun. 35: 979-989 (1982).

Weiss et al., "Energy metabolism of monocytic *Ehrlichia*," Proc. Natl. Acad. Sci. 86:1674-1678 (1989).

Wells et al., "Lack of lysosomal fusion with phagosomes containing *Ehrlichia risticii* in P388D1 Cells: Abrogation of inhibition with oxytetracycline" Infect. Immun. 56: 3209-3215 (1998).

Wen et al., "Diversity of 16S rRNA Genes of new *Ehrlichia* strains isolated from horses with clinical signs of potomac horse fever" Int. J. Sys. Bacteriol, 45: 315-318 (1995).

Wen et al., "Comparison of Nested PCR with Immunofluorescent-Antibody Assay for detection of *Ehrlichia canis* infection in dogs Treated with doxycycline" J. Clin. Microbiol. 35: 1852-1855 (1997).

Yamamoto et al "Serosurvey of anti-*Ehrlichia canis* antibody in dogs" J Japanese Small Animal Veterinary Med Assoc 47: 765-767 (1994) & English translation.

Yu et al., "Genetic divergence of a 120-kDa immunodominant protein of *Ehrlichia chaffeensis*: a potential recombinant diagnostic tool," In Proceedings of the Vth International Symposium of Rickettsiae and Rickettsial Diseases, Stara Lesna, Slovak Academy of Sciences 324-328 ( J. Kasar, R. Toman, editors, Batislava, Slovak Republic, Sep. 1-6, 1996).

Yu et al. "Characterization of the complete transcriptionally active *Ehrlichia chaffeensis* 28 kDa outer membrane protein multigene family", Gene, 248, 59-68, 2000.

Zhang et al., "Antigenic variation in Lyme disease borreliae by promiscuous recombination of VMP-like sequence cassettes," Cell 89: 275-285 (1997).

Zhang et al., "*Ehrlichia sennetsu* groE operon and antigenic properties of the GroEL homolog," FEMS Immunol. Med. Microbiol. 18: 39-46 (1997).

Zhi et al "Multiple p44 Genes Encoding Major Outer Membrane Proteins are Expressed in Human Granulocytic Ehrlichiosis Agent" J Biol Chem vol. 274 Issue 25 pp. 17828-17836 Jun. 18, 1999.

Yu et al "Sequence and characterization of an *Erlichia chaffeensis* gene encoding 314 amino acids high homologous to the NADA enzyme" FEMS Microbiol Lett 154 (1) 53-58 (1997).

Office action from related U.S. Appl. No. 10/138,162, "Methods for detecting *Ehrlichia canis* and *Ehrlichia chaffeensis* in vertebrate and invertebrate hosts", filed May 2, 2002, Office action mailed Oct. 5, 2005.

Walker, DH et al., "Emergence of the Ehrlichioses as Human Health Problems", Emerg. Infect Dis 2 (1): 18-29 (1996).

Dawson, JE et al., "Polymerase chain reaction evidence of *Ehrlichia chaffensis*, an etiologic agent of human ehrlichiosis, in dogs from southeast Virginia", Am. J. Vet. Res. 57 (8): 1175-1179 (1996).

Dawson, JE et al., "*Ehrlichia*-like 16S rDNA sequence from wild white-tailed deer (*Odocoileus virginianus*)", J. Parasitol. 82 (1): 52-58 (1996).

Genbank Accession Version AF077732.1.
Genbank Accession Version AF077733.1.
Genbank Accession Version AF077734.1.
Genbank Accession Version AF077735.1.
Genbank Accession Version AF082744.1.
Genbank Accession Version AF082745.1.
Genbank Accession Version AF082746.1.
Genbank Accession Version AF082747.1.
Genbank Accession Version AF082748.1.
Genbank Accession Version AF082749.1.
Genbank Accession Version AF082750.1.

* cited by examiner

```
       10         20         30         40         50         60
ATGAATTACA AAAAAGTTTT CATAACAAGT GCATTGATAT CATTAATATC TTCTCTACCT
       70         80         90        100        110        120
GGAGTATCAT TTTCCGACCC AGCAGGTAGT GGTATTAACG GTAATTTCTA CATCAGTGGA
      130        140        150        160        170        180
AAATACATGC CAAGTGCTTC GCATTTTGGA GTATTCTCTG CTAAGGAAGA AAGAAATACA
      190        200        210        220        230        240
ACAGTTGGAG TGTTTGGACT GAAGCAAAAT TGGGACGGAA GCGCAATATC CAACTCCTCC
      250        260        270        280        290        300
CCAAACGATG TATTCACTGT CTCAAATTAT TCATTTAAAT ATGAAAACAA CCCGTTTTTA
      310        320        330        340        350        360
GGTTTTGCAG GAGCTATTGG TTACTCAATG GATGGTCCAA GAATAGAGCT TGAAGTATCT
      370        380        390        400        410        420
TATGAAACAT TTGATGTAAA AAATCAAGGT AACAATTATA AGAATGAAGC ACATAGATAT
      430        440        450        460        470        480
TGTGCTCTAT CCCATAACTC AGCAGCAGAC ATGAGTAGTG CAAGTAATAA TTTTGTCTTT
      490        500        510        520        530        540
CTAAAAAATG AAGGATTACT TGACATATCA TTTATGCTGA ACGCATGCTA TGACGTAGTA
      550        560        570        580        590        600
GGCGAAGGCA TACCTTTTTC TCCTTATATA TGCGCAGGTA TCGGTACTGA TTTAGTATCC
      610        620        630        640        650        660
ATGTTTGAAG CTACAAATCC TAAAATTTCT TACCAAGGAA AGTTAGGTTT AAGCTACTCT
      670        680        690        700        710        720
ATAAGCCCAG AAGCTTCTGT GTTTATTGGT GGGCACTTTC ATAAGGTAAT AGGGAACGAA
      730        740        750        760        770        780
TTTAGAGATA TTCCTACTAT AATACCTACT GGATCAACAC TTGCAGGAAA AGGAAACTAC
      790        800        810        820        830        840
CCTGCAATAG TAATACTGGA TGTATGCCAC TTTGGAATAG AACTTGGAGG AAGGTTTGCT
      850        860        870        880        890        900
TTCTAA....  .........  .........  .........  .........  .........
```

FIG. 3A

```
          10         20         30         40         50         60
MNYKKVFITS ALISLISSLP GVSFSDPAGS GINGNFYISG KYMPSASHFG VFSAKEERNT
          70         80         90        100        110        120
TVGVFGLKQN WDGSAISNSS PNDVFTVSNY SFKYENNPFL GFAGAIGYSM DGPRIELEVS
         130        140        150        160        170        180
YETFDVKNQG NNYKNEAHRY CALSHNSAAD MSSASNNFVF LKNEGLLDIS FMLNACYDVV
         190        200        210        220        230        240
GEGIPFSPYI CAGIGTDLVS MFEATNPKIS YQGKLGLSYS ISPEASVFIG GHFHKVIGNE
         250        260        270        280        290        300
FRDIPTIIPT GSTLAGKGNY PAIVILDVCH FGIELGGRFA F.......... ..........
```

FIG. 3B

```
          10         20         30         40         50         60
ATGAATTACA AGAAAATTTT TGTAAGCAGT GCATTAATTT CATTAATGTC AATCTTACCT
          70         80         90        100        110        120
TACCAATCTT TTGCAGATCC TGTAACTTCA AATGATACAG GAATCAACGA CAGCAGAGAA
         130        140        150        160        170        180
GGCTTCTACA TTAGTGTAAA GTATAATCCA AGCATATCAC ACTTCAGAAA ATTCTCAGCT
         190        200        210        220        230        240
GAAGAAGCTC CCATCAATGG AAATACTTCT ATCACTAAAA AGGTTTTCGG GCTGAAAAAA
         250        260        270        280        290        300
GACGGAGATA TAGCACAATC TGCGAATTTT AACAGGACAG ATCCAGCCCT CGAGTTTCAG
         310        320        330        340        350        360
AATAACCTAA TATCAGGATT CTCAGGAAGT ATTGGTTATG CTATGGATGG GCCAAGAATA
         370        380        390        400        410        420
GAACTTGAAG CTGCATACCA AAAATTTGAT GCAAAAAATC CTGACAACAA TGACACTAAT
         430        440        450        460        470        480
AGCGGTGACT ACTATAAATA CTTTGGACTA TCTCGTGAAG ACGCAATAGC AGATAAGAAA
         490        500        510        520        530        540
TATGTTGTCC TTAAAAATGA AGGCATCACT TTTATGTCAT AATGGTTAA CACTTGCTAT
         550        560        570        580        590        600
GACATTACAG CTGAAGGAGT ACCTTTCATA CCGTATGCAT GTGCAGGTGT AGGAGCAGAC
         610        620        630        640        650        660
CTTATAAACG TATTTAAGGA TTTTAATTTA AAATTCTCAT ACCAAGGGAA AATAGGTATT
         670        680        690        700        710        720
AGCTATCCAA TCACACCAGA AGTTTCCGCT TTTATTGGAG GATACTACCA CGGAGTTATA
         730        740        750        760        770        780
GGAAATAATT TTAACAAAAT ACCTGTAATA ACACCTGTAG TATTAGAAGG AGCTCCTCAA
         790        800        810        820        830        840
ACCACATCTG CGCTAGTAAC TATTGACACT GGATACTTTG GCGGAGAAGT TGGAGTAAGG
         850        860        870        880        890        900
TTCACCTTCT AG........ .......... .......... .......... ..........
```

*FIG. 4A*

```
         10         20         30         40         50         60
MNYKKIFVSS ALISLMSILP YQSFADPVTS NDTGINDSRE GFYISVKYNP SISHFRKFSA
         70         80         90        100        110        120
EEAPINGNTS ITKKVFGLKK DGDIAQSANF NRTDPALEFQ NNLISGFSGS IGYAMDGPRI
        130        140        150        160        170        180
ELEAAYQKFD AKNPDNNDTN SGDYYKYFGL SREDAIADKK YVVLKNEGIT FMSLMVNTCY
        190        200        210        220        230        240
DITAEGVPFI PYACAGVGAD LINVFKDENL KFSYQGKIGI SYPITPEVSA FIGGYYHGVI
        250        260        270        280        290        300
GNNGNKIPVI TPVVLEGAPQ TTSALVTIDT GYFGGEVGVR FTF.......  ..........
```

FIG. 4B

```
         10         20         30         40         50         60
ATGAACTGCA AAAAATTTTT TATAACAACT GCATTGGCAT TGCCAATGTC TTTCTTACCT
         70         80         90        100        110        120
GGAATATTAC TTTCTGAACC AGTACAAGAT GACAGTGTGA GTGGCAATTT CTATATTAGT
        130        140        150        160        170        180
GGCAAGTACA TGCCAAGTGC TTCTCATTTT GGAGTTTTCT CTGCCAAAGA AGAAAAAAAT
        190        200        210        220        230        240
CCTACTGTCG CGTTGTATGG TTTGAAACAA GATTGGAACG GTGTTAGTGC TTCAAGTCAT
        250        260        270        280        290        300
GCTGATGCGG ACTTTAATAA CAAAGGTTAT TCTTTTAAAT ACGAAAACAA TCCATTTCTA
        310        320        330        340        350        360
GGTTTTGCAG GAGCTATTGG TTATTCAATG GGTGGTCCAA GAATAGAGTT TGAAGTGTCC
        370        380        390        400        410        420
TATGAAACAT TTGACGTGAA AAATCAAGGT GGTAATTACA AAAATGATGC TCACAGATAC
        430        440        450        460        470        480
TGTGCCTTAG ATCGTAAAGC AAGCAGCACT AATGCCACAG CTAGTCACTA CGTGCTACTA
        490        500        510        520        530        540
AAAAATGAAG GACTACTTGA TATATCACTT ATGTTGAATG CATGCTATGA CGTAGTAAGT
        550        560        570        580        590        600
GAAGGAATAC CTTTCTCTCC TTACATATGT GCAGGTGTTG GTACCGATTT AATATCCATG
        610        620        630        640        650        660
TTTGAAGCTA TAAACCCTAA AATTTCTTAT CAAGGAAAGT TAGGTTTGAG TTACTCTATA
        670        680        690        700        710        720
AACCCAGAAG CTTCTGTCTT TGTTGGTGGA CATTTTCATA AAGTTGCAGG TAATGAATTC
        730        740        750        760        770        780
AGGGACATTT CTACTCTTAA AGCGTTTGCT ACACCATCAT CTGCAGCTAC TCCAGACTTA
        790        800        810        820        830        840
GCAACAGTAA CACTGAGTGT GTGTCACTTT GGAGTAGAAC TTGGAGGAAG ATTTAACTTC
        850        860        870        880        890        900
TAA
```

*FIG. 5A*

```
          10         20         30         40         50         60
MNCKKFFITT ALALPMSFLP GILLSEPVQD DSVSGNFYIS GKYMPSASHF GVFSAKEEKN
          70         80         90        100        110        120
PTVALYGLKQ DWNGVSASSH ADADFNNKGY SFKYENNPFL GFAGAIGYSM GGPRIEFEVS
         130        140        150        160        170        180
YETFDVKNQG GNYKNDAHRY CALDRKASST NATASHYVLL KNEGLLDISL MLNACYDVVS
         190        200        210        220        230        240
EGIPFSPYIC AGVGTDLISM FEAINPKISY QGKLGLSYSI NPEASVFVGG HFHKVAGNEF
         250        260        270        280        290        300
RDISTLKAFA TPSSAATPDL ATVTLSVCHF GVELGGRFNF .......... ..........
```

FIG. 5B

```
          10         20         30         40         50         60
  ATGAACTGCG AAAAATTTTT TATAACAACT GCATTAACAT TACTAATGTC CTTCTTACCT
          70         80         90        100        110        120
  GGAATATCAC TTTCTGATCC AGTACAGGAT GACAACATTA GTGGTAATTT CTACATCAGT
         130        140        150        160        170        180
  GGAAAGTATA TGCCAAGCGC TTCGCATTTT GGAGTTTTTT CTGCCAAGGA AGAAAGAAAT
         190        200        210        220        230        240
  ACAACAGTTG GAGTATTTGG AATAGAGCAA GATTGGGATA GATGTGTAAT ATCTAGAACC
         250        260        270        280        290        300
  ACTTTAAGCG ATATATTCAC CGTTCCAAAT TATTCATTTA AGTATGAAAA TAATCTATTT
         310        320        330        340        350        360
  TCAGGATTTG CAGGAGCTAT TGGCTACTCA ATGGATGGCC CAAGAATAGA GCTTGAAGTA
         370        380        390        400        410        420
  TCTTATGAAG CATTCGATGT TAAAAATCAA GGTAACAATT ATAAGAACGA AGCACATAGA
         430        440        450        460        470        480
  TATTATGCTC TGTCCCATCT TCTCGGCACA GAGACACAGA TAGATGGTGC AGGCAGTGCG
         490        500        510        520        530        540
  TCTGTCTTTC TAATAAATGA AGGACTACTT GATAAATCAT TTATGCTGAA CGCATGTTAT
         550        560        570        580        590        600
  GATGTAATAA GTGAAGGCAT ACCTTTTTCT CCTTATATAT GTGCAGGTAT TGGTATTGAT
         610        620        630        640        650        660
  TTAGTATCCA TGTTTGAAGC TATAAATCCT AAAATTTCTT ATCAAGGAAA ATTAGGCTTA
         670        680        690        700        710        720
  AGTTACCCTA TAAGCCCAGA AGCTTCTGTG TTTATTGGTG GACATTTTCA TAAGGTGATA
         730        740        750        760        770        780
  GGAAACGAAT TTAGAGATAT TCCTACTATG ATACCTAGTG AATCAGCGCT TGCAGGAAAA
         790        800        810        820        830        840
  GGAAACTACC CTGCAATAGT AACACTGGAC GTGTTCTACT TTGGCATAGA ACTTGGAGGA
         850        860        870        880        890        900
  AGGTTTAACT TCCAACTTTG A......... .......... .......... ..........
```

FIG. 6A

```
          10         20         30         40         50         60
MNCEKFFITT ALTLLMSFLP GISLSDPVQD DNISGNFYIS GKYMPSASHF GVFSAKEERN
          70         80         90        100        110        120
TTVGVFGIEQ DWDRCVISRT TLSDIFTVPN YSFKYENNLF SGFAGAIGYS MDGPRIELEV
         130        140        150        160        170        180
SYEAFDVKNQ GNNYKNEAHR YYALSHLLGT ETQIDGAGSA SVFLINEGLL DKSFMLNACY
         190        200        210        220        230        240
DVISEGIPFS PYICAGIGID LVSMFAEINP KISYQGKLGL SYPISPEASV FIGGHFHKVI
         250        260        270        280        290        300
GNEFRDIPTM IPSESALAGK GNYPAIVTLD VFYFGIELGG RFNFQL.... ..........
```

FIG. 6B

```
         10         20         30         40         50         60
ATGAATTGCA AAAAATTTTT TATAACAACT GCATTAGTAT CACTAATGTC CTTTCTACCT
         70         80         90        100        110        120
GGAATATCAT TTTCTGATCC AGTGCAAGGT GACAATATTA GTGGTAATTT CTATGTTAGT
        130        140        150        160        170        180
GGCAAGTATA TGCCAAGTGC TTCGCATTTT GGCATGTTTT CTGCCAAAGA AGAAAAAAAT
        190        200        210        220        230        240
CCTACTGTTG CATTGTATGG CTTAAAACAA GATTGGGAAG GGATTAGCTC ATCAAGTCAC
        250        260        270        280        290        300
AATGATAATC ATTTCAATAA CAAGGGTTAT TCATTTAAAT ATGAAAATAA CCCATTTTTA
        310        320        330        340        350        360
GGGTTTGCAG GAGCTATTGG TTATTCAATG GGTGGTCCAA GAGTAGAGTT TGAAGTGTCC
        370        380        390        400        410        420
TATGAAACAT TTGACGTTAA AAATCAGGGT AATAACTATA AAATGATGC TCACAGATAC
        430        440        450        460        470        480
TGTGCTTTAG GTCAACAAGA CAACAGCGGA ATACCTAAAA CTAGTAAATA CGTACTGTTA
        490        500        510        520        530        540
AAAAGCGAAG GATTGCTTGA CATATCATTT ATGCTAAATG CATGCTATGA TATAATAAAC
        550        560        570        580        590        600
GAGAGCATAC CTTTGTCTCC TTACATATGT GCAGGTGTTG GTACTGATTT AATATCCATG
        610        620        630        640        650        660
TTTGAAGCTA CAAATCCTAA AATTTCTTAC CAAGGGAAGT TAGGTCTAAG TTACTCTATA
        670        680        690        700        710        720
AACCCAGAAG CTTCTGTATT TATTGGTGGA CATTTTCATA AGGTGATAGG AAACGAATTT
        730        740        750        760        770        780
AGGGACATTC CTACTCTGAA AGCATTTGTT ACGTCATCAG CTACTCCAGA TCTAGCAATA
        790        800        810        820        830        840
GTAACACTAA GTGTATGTCA TTTTGGAATA GAACTTGGAG GAAGGTTTAA CTTCTAA...
```

FIG. 7A

```
          10         20         30         40         50         60
MNCKKFFITT ALVSLMSFLP GISFSDPVQG DNISGNFYVS GKYMPSASHF GMFSAKEEKN
          70         80         90        100        110        120
PTVALYGLKQ DWEGISSSSH NDNHFNNKGY SFKYENNPFL GFAGAIGYSM GGPRVEFEVS
         130        140        150        160        170        180
YETFDVKNQG NNYKNDAHRY CALGQQDNSG IPKTSKYVLL KSEGLLDISF MLNACYDIIN
         190        200        210        220        230        240
ESIPLSPYIC AGVGTDLISM FEATNPKISY QGKLGLSYSI NPEASVFIGG HFHKVIGNEF
         250        260        270        280        290        300
RDIPTLKAFV TSSATPDLAI VTLSVCHFGI ELGGRFNF.. .......... ..........
```

*FIG. 7B*

```
          10         20         30         40         50         60
   ATGAATTGCA AAAAATTTTT TATAACAACT ACATTAGTAT CGCTAATGTC CTTCTTACCT
          70         80         90        100        110        120
   GGAATATCAT TTTCTGATGC AGTACAGAAC GACAATGTTG GTGGTAATTT CTATATCAGT
         130        140        150        160        170        180
   GGGAAATATG TACCAAGTGT TTCACATTTT GGCGTATTCT CTGCTAAACA GGAAAGAAAT
         190        200        210        220        230        240
   ACAACAACCG GAGTATTTGG ATTAAAGCAA GATTGGGATG GCAGCACAAT ATCTAAAAAT
         250        260        270        280        290        300
   TCTCCAGAAA ATACATTTAA CGTTCCAAAT TATTCATTTA AATATGAAAA TAATCCATTT
         310        320        330        340        350        360
   CTAGGTTTTG CAGGAGCTGT TGGTTATTTA ATGAATGGTC CAAGAATAGA GTTAGAAATG
         370        380        390        400        410        420
   TCCTATGAAA CATTTGATGT GAAAAACCAG GGTAATAACT ATAAGAACGA TGCTCACAAA
         430        440        450        460        470        480
   TATTATGCTT TAACCCATAA CAGTGGGGGA AAGCTAAGCA ATGCAGGTGA TAAGTTTGTT
         490        500        510        520        530        540
   TTTCTAAAAA ATGAAGGACT ACTTGATATA TCACTTATGT TGAATGCATG CTATGATGTA
         550        560        570        580        590        600
   ATAAGTGAAG GAATACCTTT CTCTCCTTAC ATATGTGCAG GTGTTGGTAC TGATTTAATA
         610        620        630        640        650        660
   TCCATGTTTG AAGCTATAAA CCCTAAAATT TCTTATCAAG GAAAGTTAGG TTTGAGTTAC
         670        680        690        700        710        720
   TCCATAAGCC CAGAAGCTTC TGTTTTTGTT GGTGGACATT TTCATAAGGT GATAGGGAAT
         730        740        750        760        770        780
   GAATTCAGAG ATATTCCTGC TATGATACCC AGTACCTCAA CTCTCACAGG TAATCACTTT
         790        800        810        820        830        840
   ACTATAGTAA CACTAAGTGT ATGCCACTTT GGAGTGGAAC TTGGAGGAAG GTTTAACTTT
         850        860        870        880        890        900
   TAA....... .......... .......... .......... .......... ..........
```

FIG. 8A

```
          10         20         30         40         50         60
MNCKKFFITT TLVSLMSFLP GISFSDAVQN DNVGGNFYIS GKYVPSVSHF GVFSAKQERN
          70         80         90        100        110        120
TTTGVFGLKQ DWDGSTISKN SPENTFNVPN YSFKYENNPF LGFAGAVGYL MNGPRIELEM
         130        140        150        160        170        180
SYETFDVKNQ GNNYKNDAHK YYALTHNSGG KLSNAGDKFV FLKNEGLLDI SLMLNACYDV
         190        200        210        220        230        240
ISEGIPFSPY ICAGVGTDLI SMFEAINPKI SYQGKLGLSY SISPEASVFV GGHFHKVIGN
         250        260        270        280        290        300
EFRDIPAMIP STSTLTGNHF TIVTLSVSHF GVELGGRFNF .......... ..........
```

FIG. 8B

```
          10         20         30         40         50         60
   ATGGAAAATC TCATGAATAA GAAAAACAAA TTCTTTACAA TAAGTACAGC AATGGTATGC
          70         80         90        100        110        120
   TTATTGTTAT TACCTGGTAT ATCATTTTCA GAAACTATAA ACAACAGTGC TAAAAAACAG
         130        140        150        160        170        180
   CCTGGGTTAT ATATCAGTGG GCAGTACAAA CCTAGTGTTT CAGTTTTTAG TAATTTTTCA
         190        200        210        220        230        240
   GTAAAAGAAA CTAATGTTCC CACAAAGCAG TTAATAGCAC TTAAAAAAGA CATTAATTCT
         250        260        270        280        290        300
   GTTGCAGTTG GTAGTAATGC TACTACAGGT ATTAGCAATC CAGGTAATTT CACAATTCCT
         310        320        330        340        350        360
   TATACTGCAG AATTTCAAGA TAATGTTGCC AATTTCAATG GGGCTGTTGG TTACTCTTTT
         370        380        390        400        410        420
   CCTGATAGTC TAAGAATTGA AATAGAGGGA TTTCATGAAA AATTTGATGT CAAAAACCCT
         430        440        450        460        470        480
   GGAGGTTACA CACAAGTAAA AGATGCGTAC CGTTATTTTG CACTAGCACG TGATTTAAAA
         490        500        510        520        530        540
   GATGGCTTCT TTGAACCTAA AGCGGAAGAT ACAGGTGTTT ATCATACTGT TATGAAAAAT
         550        560        570        580        590        600
   GATGGATTAT CTATTTTATC TACTATGGTT AACGTCTGTT ACGATTTTTC TGTAGATGAA
         610        620        630        640        650        660
   TTACCAGTCT TACCTTATAT ATGTGCAGGT ATGGGTATAA ACGCCATAGA ATTCTTCGAC
         670        680        690        700        710        720
   GCTTTACATG TAAAATTTGC TTACCAAGGC AAACTAGGTA TTAGCTATCA ACTATTTACT
         730        740        750        760        770        780
   AAAGTAAATT TATTCCTTGA TGGGTATTAC CATCAAGTAA TAGGCAATCA ATTCAAAAAC
         790        800        810        820        830        840
   TTAAACGTAA ACCATGTTTA CACACTTAAA GAATCTCCTA AAGTCACATC TGCAGTAGCT
         850        860        870        880        890        900
   ACACTTGACA TTGCATACTT TGGTGGCGAA GTTGGAATAA GATTCACATT TTAA......
```

*FIG. 9A*

```
         10         20         30         40         50         60
MENLMNKKNK FFTISTAMVC LLLLPGISFS ETINNSAKKQ PGLYISGQYK PSVSVFSNFS
         70         80         90        100        110        120
VKETNVPTKQ LIALKKDINS VAVGSNATTG ISNPGNFTIP YTAEFQDNVA NFNGAVGYSF
        130        140        150        160        170        180
PDSLRIEIEG FHEKFDVKNP GGYTQVKDAY RYFALARDLK DGFFEPKAED TGVYHTVMKN
        190        200        210        220        230        240
DGLSILSTMV NVCYDFSVDE LPVLPYICAG MGINAIEFED ALHVKFAYQG KLGISYQLFT
        250        260        270        280        290        300
KVNLFLDGYY HQVIGNQFKN LNVNHVYTLK ESPKVTSAVA TLDIAYFGGE VGIRFTF...
```

FIG. 9B

```
          10         20         30         40         50         60
ATGATATATA AAGAAAAACT TACTAGAGTG GGAGAATATA TCTTAGCATA TTTATCATTT
          70         80         90        100        110        120
ATTCTTTCTA CTTATATCTT TCTAGTGCTG GTAAATATTA TTAGATATAA CAGCCTTGCT
         130        140        150        160        170        180
ATATGTGTTA TCAGTCTACT AAGAACTAAT ATCTTTAACG TTAGCACAAA AAAATTAATA
         190        200        210        220        230        240
AAAGATAAAT GTCGTGATAC TAAGTTTAGT AACATGAATT GTTATTTGTA CGGTAAACCG
         250        260        270        280        290        300
TTAAATTTAC AAATTTTTTA TGGAATATTT TCCTTTATTA GAAACTTTCA AAATAACACA
         310        320        330        340        350        360
CTAATAATTC CTAATGATAG TAAATGCGGC TTCTATACCA CGTTATGGGA TAATCCAGCA
         370        380        390        400        410        420
CTACATTATA CATATACACT TACTGGCAGT GAGTACCGTA ATTTTTTTGA CATTCTATAT
         430        440        450        460        470        480
GAAAACATTA TCTGTCAATG TAAATTACTT ATTAACTATA ACCGTTCTGT ATTAAACCAA
         490        500        510        520        530        540
CATAATAAAA ATACTCTCGT AATAATACCA ATACCTAATG CTAGAGAGTT CAGTAATGAA
         550        560        570        580        590        600
ATTCGAGTAA GGAATATATC AATAAATAAG GAAAGTTCTT ATGAGTGCTA A.........
```

FIG. 10A

```
         10         20         30         40         50         60
MIYKEKLTRV GEYILAYLSF ILSTYIFLVL VNIIRYNSLA ICVISLLRTN IFNVSTKKLI
         70         80         90        100        110        120
KDKCRDTKFS NMNCYLYGKP LNLQIFYGIF SFIRNFQNNT LIIPNDSKCG FYTTLWDNPA
        130        140        150        160        170        180
LHYTYTLTGS EYRNFEDILY ENIICQCKLL INYNRSVLNQ HNKNTLVIIP IPNAREFSNE
        190        200        210        220        230        240
IRVRNISINK ESSYEC.... .......... .......... .......... ..........
```

FIG. 10B

```
         10         20         30         40         50         60
ATGAATAAAA AAAACAAGTT TATTATAGCT ACAGCATTGG TATATTTACT GTCATTACCT
         70         80         90        100        110        120
AGTGTATCGT TTTCAGAGGT TACAAACAGC AGTATTAAAA AACACTCTGG GTTATATATT
        130        140        150        160        170        180
AGTGGACAAT ACAAACCAAG TGTTTCTGTT TTTAGTAGTT CTCAATTAA AGAAACTAAC
        190        200        210        220        230        240
ACTATCACAA AAAATCTTAT AGCGTTAAAA AAAGATATTA ACTCTCTTGA AGTTAACGCC
        250        260        270        280        290        300
GATGCTAGTC AAGGTATTAG TCATCCAGGA AATTTTACTA TACCTTATAT AGCAGCATTT
        310        320        330        340        350        360
GAAGATAATG CTTTTAATTT CAACGGTGCT ATTGGTTACA TTACTGAAGG TCTAAGGATT
        370        380        390        400        410        420
GAAATAGAAG GTTCCTATGA AGAATTTGAT GCTAAAAACC CTGGAGGTTA TGGTCTAAAT
        430        440        450        460        470        480
GATGCCTTTC GGTACTTTGC TTTAGCACGT GATATGGAAA GCAACAAGTT CCAACCAAAA
        490        500        510        520        530        540
GCACAAAGCT CACAAAAAGT ATTTCACACT GTAATGAAGA GTGATGGGTT ATCTATAATA
        550        560        570        580        590        600
TCTATCATGG TTAACGGCTG TTATGATTTT TCTTCGGATA ATTTATTAGT ATCACCTTAT
        610        620        630        640        650        660
ATATGTGGAG GTATAGGTGT GGATGCAATA GAATTTTTTG ACGCATTACA CATTAAACTT
        670        680        690        700        710        720
GCGTGCCAAA GCAAATTAGG CATCACTTAT CAATTATCTT ATAATATCAG CTTATTTGCT
        730        740        750        760        770         780
GATGGATATT ATCATCAAGT AATAGGTAAC CAATTCAGAA ATTTAAACGT TCAACATGTA
        790        800        810        820        830        840
GCTGAACTTA ATGATGCACC TAAAGTTACA TCTGCAGTTG CCACACTTAA TGTTGGATAT
        850        860        870        880        890        900
TTCGGCGCTG AAGTTGGAGT AAGATTTATA TTTTAA....  .........  .........
```

FIG. 11A

|    | 10         | 20         | 30         | 40         | 50         | 60         |
|----|------------|------------|------------|------------|------------|------------|
|    | MNKKNKFIIA | TALVYLLSLP | SVSFSEVTNS | SIKKHSGLYI | SGQYKPSVSV | FSSFSIKETN |
|    | 70         | 80         | 90         | 100        | 110        | 120        |
|    | TITKNLIALK | KDINSLEVNA | DASQGISHPG | NFTIPYIAAF | EDNAFNFNGA | IGYITEGLRI |
|    | 130        | 140        | 150        | 160        | 170        | 180        |
|    | EIEGSYEEFD | AKNPGGYGLN | DAFRYFALAR | DMESNKFQPK | AQSSQKVFHT | VMKSDGLSII |
|    | 190        | 200        | 210        | 220        | 230        | 240        |
|    | SIMVNGCYDF | SSDNLLVSPY | ICGGIGVDAI | EFFDALHIKL | ACQSKLGITY | QLSYNISLFA |
|    | 250        | 260        | 270        | 280        | 290        | 300        |
|    | DGYYHQVIGN | QFRNLNVQHV | AELNDAPKVT | SAVATLNVGY | FGAEVGVRFI | F.........|

*FIG. 11B*

```
        10         20         30         40         50         60
TCTAGAATAC ATGATGAAAA TTATGCTATT ACAACAAATA ATAAATTATC CATCGCATCT
        70         80         90        100        110        120
ATTATGGTTA ACACCTGCTA TGATATTTCA ATTAATAATA CATCAATAGT ACCGTATTTA
       130        140        150        160        170        180
TGCACAGGCA TTGGTGAAGA TCTTGTAGGG CTTTTTAATA CAATACATTT TAAACTTGCA
       190        200        210        220        230        240
TATCAAGGGA AAGTTGGAAT GAGTTATTTG ATAAATAACA ATATCCTATT ATTTTCTGAC
       250        260        270        280        290        300
ATATATTATC ATAAAGTCAT GGGTAACAGA TTTAAAAATT TGTACATGCA ATATGTAGCT
       310        320        330        340        350        360
GATCCTAATA TTTCTGAAGA AACTATACCT ATATTAGCAA AACTTGATAT TGGTTATTTT
       370        380        390        400        410        420
GGAAGTGAAA TTGGAATAAG GTTTATGTTT AACTAA.... .......... ..........
```

FIG. 12A

```
        10         20         30         40         50         60
SRIHDENYAI TTNNKLSIAS IMVNTCYDIS INNTSIVPYL CTGIGEDLVG LFNTIHFKLA
        70         80         90        100        110        120
YQGKVGMSYL INNNILLFSD IYYHKVMGNR FKNLYMQYVA DPNISEETIP ILAKLDIGYF
       130        140        150        160        170        180
GSEIGIRFMF N......... .......... .......... .......... ..........
```

FIG. 12B

```
         10         20         30         40         50         60
ATGACAAAGA AATTTAATTT TGTAAATGTT ATATTAACAT TTTTGTTATT TCTTTTCCCA
         70         80         90        100        110        120
CTTAAGTCAT TTACAACATA TGCAAATAAT AACACAATCA CTCAAAAAGT TGGATTGTAC
        130        140        150        160        170        180
ATAAGTGGTC AATATAAGCC AAGTATTCCT CATTTCAAGA ATTTTTCAGT AGAAGAAAAT
        190        200        210        220        230        240
GACAAAGTAG TAGATTTGAT AGGTCTTACA ACTGATGTTA CATATATCAC AGAACATATA
        250        260        270        280        290        300
TTACGAGATA ATACAAAATT CAACACTCAT TATATTGCAA AGTTCAAGAA CAATTTTATA
        310        320        330        340        350        360
AATTTCAGCA GTGCAATTGG TTATTATTCT GGGCAAGGAC CAAGGTTAGA AATAGAAAGC
        370        380        390        400        410        420
TCTTATGGGG ATTTTGATGT TGTAAATTAT AAAAATTATG CAGTACAAGA TGTTAATAGA
        430        440        450        460        470        480
TATTTTGCTT TAGTACGTGA AAAAAATGGT TCAAATTTCT CTCCAAAACC ACATGAAACT
        490        500        510        520        530        540
AGTCAACCCT CTGACAGTAA TCCTAAAAAG TCTTTTTATA CTTTAATGAA GAATAATGGG
        550        560        570        580        590        600
GTATTTGTTG CATCAGTAAT AATCAACGGT TGTTATGATT TTTCTTTTAA TAACACAACA
        610        620        630        640        650        660
ATATCACCTT ACGTATGTAT AGGAGTTGGA GGAGATTTTA TAGAGTTTTT TGAAGTAATG
        670        680        690        700        710        720
CATATCAAGT TTGCTTGCCA AAGTAAGGTT GGTATTAGCT ATCCAATATC TCCCTCTATT
        730        740        750        760        770        780
ACTATTTTTG CTGATGCAVA TTATCACAAG GTCATAAATA ATAAATTTAA CAACCTACAT
        790        800        810        820        830        840
GTTAAGTATT CATATGAACT TAAAAACTCA CCTACCATTA CCTCTGCAAC AGCCAAACTA
        850        860        870        880        890        900
AACATTGAAT ATTTTGGTGG TGAAGTTGGG ATGAGATTTA TATTTTAA..  ..........
```

FIG. 13A

```
          10         20         30         40         50         60
MTKKFNFVNV ILTFLLFLFP LKSFTTYANN NTITQKVGLY ISGQYKPSIP HFKNFSVEEN
          70         80         90        100        110        120
DKVVDLIGLT TDVTYITEHI LRDNTKFNTH YIAKFKNNFI NFSSAIGYYS GQGPRLEIES
         130        140        150        160        170        180
SYGDFDVVNY KNYAVQDVNR YFALVREKNG SNFSPKPHET SQPSDSNPKK SFYTLMKNNG
         190        200        210        220        230        240
VFVASVIING CYDFSFNNTT ISPYVCIGVG GDFIEFFEVM HIKFACQSKV GISYPISPSI
         250        260        270        280        290        300
TIFADAHYHK VINNKFNNLH VKYSYELKNS PTITSATAKL NIEYFGGEVG MRFIF.....
```

FIG. 13B

```
         10         20         30         40         50         60
ATGAGCAAAA AAAAGTTTAT TACAATAGGA ACAGTACTTG CATCTCTATT ATCATTCTTA
         70         80         90        100        110        120
TCTATTGAAT CCTTTTCAGC TATAAATCAT AATCATACAG GAAATAACAC TAGTGGTATA
        130        140        150        160        170        180
TATATTACAG GGCAGTATAG ACCAGGAGTA TCCCATTTTA GCAATTTCTC AGTAAAAGAA
        190        200        210        220        230        240
ACTAATGTTG ATACAATACA ACTAGTAGGA TATAAAAAAA GTGCGTCTTC TATCGATCCT
        250        260        270        280        290        300
AACACTTATT CAAACTTTCA AGGTCCATAT ACTGTTACAT TTCAAGATAA TGCTGCTAGT
        310        320        330        340        350        360
TTCAGTGGAG CAATTGGATA TTCTTACCCC GAAAGTCTAA GACTTGAACT TGAAGGTTCT
        370        380        390        400        410        420
TACGAAAAAT TTGATGTCAA AGATCCTAAA GACTACTCAG CAAAAGATGC TTTTAGGTTT
        430        440        450        460        470        480
TTTGCTCTAG CACGTAATAC GTCTACTACT GTTCCTGATG CTCAAAAATA TACAGTTATG
        490        500        510        520        530        540
AAGAATAATG GCTTATCTGT TGCATCAATC ATGATCAATG GTTGTTATGA TCTATCTTTT
        550        560        570        580        590        600
AATAATTTAG TCGTATCACC TTATATATGT GCAGGTATTG GTGAAGATTT CATTGAATTT
        610        620        630        640        650        660
TTTGATACTT TGCACATTAA ACTTGCTTAT CAAGGAAAAC TAGGTATTAG TTATTACTTC
        670        680        690        700        710        720
TTTCCTAAGA TTAATGTATT TGCTGGTGGG TACTATCATA GAGTTATAGG GAATAAATTT
        730        740        750        760        770        780
AAAAATTTAA ATGTTAACCA TGTTGTTACA CTTGATGAAT TCCTAAAGC AACTTCTGCA
        790        800        810        820        830        840
GTAGCTACAC TTAATGTTGC TTATTTTGGT GGTGAAGCTG GAGTAAAGTT TACATTTTAA
        850        860        870        880        890        900
.......... .......... .......... .......... .......... ..........
```

FIG. 14A

```
              10         20         30         40         50         60
       MSKKKFITIG TVLASLLSFL SIESFSAINH NHTGNNTSGI YITGQYRPGV SHFSNFSVKE
              70         80         90        100        110        120
       TNVDTIQLVG YKKSASSIDP NTYSNFQGPY TVTFQDNAAS FSGAIGYSYP ESLRLELEGS
             130        140        150        160        170        180
       YEKFDVKDPK DYSAKDAFRF FALARNTSTT VPDAQKYTVM KNNGLSVASI MINGCYDLSF
             190        200        210        220        230        240
       NNLVVSPYIC AGIGEDFIEF FDTLHIKLAY QGKLGISYYF FPKINVFAGG YYHRVIGNKF
             250        260        270        280        290        300
       KNLNVNHVVT LDEFPKATSA VATLNVAYFG GEAGVKFTF. .......... ..........
```

*FIG. 14B*

```
           10         20         30         40         50         60
      ATGAGTGCTA AAAAAAAGCT TTTTATAATA GGGTCAGTGT TAGTATGTTT AGTGTCATAC
           70         80         90        100        110        120
      TTACCTACTA AATCTTTGTC AAACTTAAAT AATATTAATA ATAACACTAA GTGCACTGGG
          130        140        150        160        170        180
      CTATATGTCA GTGGACAATA TAAACCTACT GTTTCTCACT TTAGTAATTT TTCACTTAAA
          190        200        210        220        230        240
      GAAACTTATA CTGACACTAA AGAGTTATTA GGACTAGCAA AAGATATTAA GTCTATTACA
          250        260        270        280        290        300
      GATATAACAA CAAATAAAAA ATTCAACATT CCTTATAACA CAAAATTTCA AGATAATGCT
          310        320        330        340        350        360
      GTTAGCTTCA GTGCAGCTGT TGGATATATT TCCCAAGACA GTCCAAGGGT TGAGGTAGAA
          370        380        390        400        410        420
      TGGTCTTATG AAGAATTTGA CGTTAAAAAT CCTGGTAATT ACGTAGTAAG TGAAGCCTTC
          430        440        450        460        470        480
      AGGTATATTG CTTTAGCAAG AGGAATTGAT AATCTTCAAA AATATCCTGA AACAAATAAG
          490        500        510        520        530        540
      TATGTTGTTA TAAAGAACAA TGGCTTATCT GTCGCATCCA TTATAATCAA TGGCTGTTAT
          550        560        570        580        590        600
      GATTTTTCTT TAAACAATTT AAAAGTATCA CCTTACATAT GCGTAGGGTT TGGTGGGGAC
          610        620        630        640        650        660
      ATTATAGAAT TTTTTAGTGC TGTAAGTTTT AAATTTGCTT ATCAAGGTAA GGTAGGTATC
          670        680        690        700        710        720
      AGTTATCCAT TATTCTCTAA TATGATTATA TTTGCTGACG GATATTACCA TAAGGTCATA
          730        740        750        760        770        780
      GGAAATAAAT TTAACAATTT AAATGTTCAA CACGTTGTTA GTCTTAACAG TCATCCTAAG
          790        800        810        820        830        840
      TCTACTTTTG CAGTAGCTAC TCTTAATGTT GAGTATTTCG GTAGTGAATT TGGGTTAAAA
          850        860        870        880        890        900
      TTTATATTTT AA........ .......... .......... .......... ..........
```

FIG. 15A

```
          10         20         30         40         50         60
MSAKKKLFII GSVLVCLVSY LPTKSLSNLN NINNNNTKCTG LYVSGQYKPT VSHFSNFSLK
          70         80         90        100        110        120
ETYTDTKELL GLAKDIKSIT DITTNKKFNI PYNTKFQDNA VSFSAAVGYI SQDSPRVEVE
         130        140        150        160        170        180
WSYEEFDVKN PGNYVVSEAF RYIALARGID NLQKYPETNK YVVIKNNGLS VASIIINGCY
         190        200        210        220        230        240
DFSLNNLKVS PYICVGFGGD IIEFFSAVSF KFAYQGKVGI SYPLFSNMII FADGYYHKVI
         250        260        270        280        290        300
GNKFNNLNVQ HVVSLNSHPK STFAVATLNV EYFGSEFGLK FIF....... ..........
```

FIG. 15B

```
         10         20         30         40         50         60
ATGAGTAAAA AAAATTTTAT TACAATAGGA GCAACACTTA TTCATATGTT GTTACCTAAC
         70         80         90        100        110        120
ATATCTTTTC CAGAAACTAT TAACAATAAC ACTGATAAAC TTTCTGGGTT ATATATAAGT
        130        140        150        160        170        180
GGGCAATATA AACCAGGGAT TTCTCATTTC AGCAAATTTT CAGTCAAAGA AATCTATAAT
        190        200        210        220        230        240
GATAACATTC AACTAATTGG GTTAAGACAC AACGCAATTT CTACTAGTAC CCTTAATATT
        250        260        270        280        290        300
AATACAGATT TTAATATCCC CTATAAAGTA ACATTTCAAA ATAACATTAC CAGCTTTAGT
        310        320        330        340        350        360
GGAGCTATTG GTTATTCTGA TCCCACAGGG GCAAGATTTG AGCTTGAAGG TTCTTATGAA
        370        380        390        400        410        420
GAATTTGATG TGACAGATCC TGGAGACTGC TTAATAAAAG ATACCTATAG ATATTTCGCT
        430        440        450        460        470        480
TTAGCTAGAA ACCCATCAGG TTCTAGCCCT ACCTCAAACA ACTATACTGT TATGAGAAAT
        490        500        510        520        530        540
GATGGTGTTT CCATTACTTC TGTTATATTT AATGGCTGTT ATGACATCTT TTTAAAGGAT
        550        560        570        580        590        600
TTAGAAGTAT CACCTTATGT ATGTGTTGGT GTAGGTGGAG ATTTTATAGA ATTTTTTGAC
        610        620        630        640        650        660
GCATTACACA TTAAATTAGC ATACCAAGGC AAGTTAGGTA TCAATTATCA CTTATCGACT
        670        680        690        700        710        720
CAAGCAAGCG TATTTATTGA TGGATATTAT CATAAGGTTA TAGGAAATCA ATTCAACAAT
        730        740        750        760        770        780
CTAAATGTTC AACACGTGGC TAGTACAGAT TTTGGACCTG TATACGCAGT AGCCACACTT
        790        800        810        820        830        840
AACATTGGTT ATTTTGGTGG TGAAATCGGA ATTAGACTTA CATTTTAA.. ..........
```

FIG. 16A

```
         10         20         30         40         50         60
MSKKNFITIG ATLIHMLLPN ISFPETINNN TDKLSGLYIS GQYKPGISHF SKFSVKEIYN
         70         80         90        100        110        120
DNIQLIGLRH NAISTSTLNI NTDFNIPYKV TFQNNITSFS GAIGYSDPTG ARFELEGSYE
        130        140        150        160        170        180
EFDVTDPGDC LIKDTYRYFA LARNPSGSSP TSNNYTVMRN DGVSITSVIF NGCYDIFLKD
        190        200        210        220        230        240
LEVSPYVCVG VGGDFIEFFD ALHIKLAYQG KLGINYHLST QASVFIDGYY HKVIGNQFNN
        250        260        270        280        290        300
LNVQHVASTD FGPVYAVATL NIGYFGGEIG IRLTF..... .......... ..........
```

FIG. 16B

```
            10         20         30         40         50         60
     ATGAATAATA GAAAAAGTTT TTTTATAATA GGTGCATCAT TACTAGCAAG CTTATTATTC
            70         80         90        100        110        120
     ACATCTGAGG CCTCTTCTAC AGGAAATGTA AGTAACCATA CTTATTTTAA ACCTAGGTTA
           130        140        150        160        170        180
     TATATCAGTG GACAATATAG ACCAGGAGTT TCTCATTTTA GCAAATTTTC AGTCAAAGAA
           190        200        210        220        230        240
     ACCAACTACA ATACTACTCA ACTAGTTGGG CTTAAAAAGG ACATCAGTGT CATAGGGAAC
           250        260        270        280        290        300
     AGTAATATCA CAACCTACAC AAATTTCAAC TTTCCTTACA TTGCAGAATT TCAAGACAAT
           310        320        330        340        350        360
     GCCATAAGTT TCAGTGGGGC AATTGGATAC TTGTATTCCG AGAATTTTAG AATTGAAGTA
           370        380        390        400        410        420
     GAGGCTTCTT ATGAAGAATT TGATGTTAAA AATCCAGAAG GATCTGCTAC AGACGCATAC
           430        440        450        460        470        480
     AGGTATTTTG CACTAGCACG TGCTATGGAT GGCACTAATA AATCTAGTCC TGATGACACA
           490        500        510        520        530        540
     AGAAAATTCA CTGTCATGAG AAATGACGGG TTATCAATTT CATCAGTAAT GATAAATGGG
           550        560        570        580        590        600
     TGTTACAATT TTACATTAGA TGATATACCA GTAGTACCGT ATGTATGCGC AGGAATAGGA
           610        620        630        640        650        660
     GGAGATTTCA TAGAGTTTTT TAATGATTTA CATGTTAAGT TTCGTCATCA AGGCAAGGTA
           670        680        690        700        710        720
     GGTATTAGTT ATTCTATATC CCCTGAAGTA AGTTTATTTC TTAACGGATA TTACCATAAA
           730        740        750        760        770        780
     GTAACAGGTA ACAGATTTAA AAACTTACAC GTTCAACACG TAAGTGATTT AAGTGACGCT
           790        800        810        820        830        840
     CCTAAGTTCA CATCTGCAGT TGCTACACTC AATGTTGGGT ACTTTGGTGG CGAAATTGGA
           850        860        870        880        890        900
     GTAAGATTTA TATTTTAA.. .......... .......... .......... ..........
```

FIG. 17A

```
          10         20         30         40         50         60
MNNRKSFFII GASLLASLLF TSEASSTGNV SNHTYFKPRL YISGQYRPGV SHFSKFSVKE
          70         80         90        100        110        120
TNYNTTQLVG LKKDISVIGN SNITTYTNFN FPYIAEFQDN AISFSGAIGY LYSENFRIEV
         130        140        150        160        170        180
EASYEEFDVK NPEGSATDAY RYFALARAMD GTNKSSPDDT RKFTVMRNDG LSISSVMING
         190        200        210        220        230        240
CYNFTLDDIP VVPYVCAGIG GDFIEFFNDL HVKFAHQGKV GISYSISPEV SLFLNGYYHK
         250        260        270        280        290        300
VTGNRGKNLH VQHVSDLSDA PKFTSAVATL NVGYFGGEIF VRFIF..... ..........
```

*FIG. 17B*

```
         10         20         30         40         50         60
ATGAAGAAGA AAAATCAATT TATCACAATA AGTACAATAT TAGTATGTTT ATTGTCATTA
         70         80         90        100        110        120
TCTAATGCAT CACTTTCAAA CACTACAAAT AGCAGCACTA AAAACAGTT TGGGTTATAT
        130        140        150        160        170        180
GTTAGTGGAC AATACAAGCC TAGTGTTTCT ATTTTTAGCA ATTTCTCAGT AAAGGAAACT
        190        200        210        220        230        240
AATTTTCCTA CAAAGTATCT AGCAGCTCTT AAAAAAGACA TTAATTCTGT CGAATTTGAC
        250        260        270        280        290        300
GATAGTGTTA CTGCTGGCAT TAGTTACCCA CTTAATTTCA GTACTCCTTA TATAGCTGTA
        310        320        330        340        350        360
TTTCAAGATA ATATTTCTAA TTTTAATGGC GCTATTGGGT ACACTTTTGT TGAAGGCCCA
        370        380        390        400        410        420
AGAATTGAAA TAGAAGGTTC TTATGAAGAA TTCGATGTCA AAGACCTGGA AGATATACAG
        430        440        450        460        470        480
AAATACAAGA TGCATACCGT TGACTTTGCT TTAGCACGTG ATATAGACTC TATTCCTACT
        490        500        510        520        530        540
AGCCCAAAAA ATAGAACTTC ACATGATGGC AACAGTTCAT ATAAGGTATA CCACACTGTA
        550        560        570        580        590        600
ATGAAAAATG AAGGACTATC TATAATATCC ATTATGGTCA ATGGCTGCTA TGATTTTTCT
        610        620        630        640        650        660
TCAGATAATT TATCAATATT ACCTTATGTA TGTGGTGGTA TAGGTGTAAA TGCTATAGAG
        670        680        690        700        710        720
TTTTTCGATG CATTACATGT TAAATTCGCG TGTCAGGGTA AATTAGGTAT TACTTATCCA
        730        740        750        760        770        780
TTATCTTCCA ACGTTAGTTT ATTTGCTGGT GGATATTATC ACCAAGTAAT GGGCAACCAA
        790        800        810        820        830        840
TTTAAAAATC TAAATGTTCA ACATGTAGCT GAACTTAATG ACGCACCCAA AGTTACATCT
        850        860        870        880        890        900
GCAGTAGCTA CACTTGACAT TGGGTATTTT GGTGGTGAAA TTGGAGCAAG GCTTATATTT
        910        920        930        940        950        960
TAA.......
```

FIG. 18A

```
         10         20         30         40         50         60
MKKKNQFITI STILVCLLSL SNASLSNTTN SSTKKQFGLY VSGQYKPSVS IFSNFSVKET
         70         80         90        100        110        120
NFPTKYLAAL KKDINSVEFD DSVTAGISYP LNFSTPYIAV FQDNISNFNG AIGYTFVEGP
        130        140        150        160        170        180
RIEIEGSYEE FDVKDLEDIQ KYKMHTVDFA LARDIDSIPT SPKNRTSHDG NSSYKVYHTV
        190        200        210        220        230        240
MKNEGLSIIS IMVNGCYDFS SDNLSILPYV CGGIGVNAIE FFDALHVKFA CQGKLGITYP
        250        260        270        280        290        300
LSSNVSLFAG GYYHQVMGNQ FKNLNVQHVA ELNDAPKVTS AVATLDIGYF GGEIGARLIF
        310        320        330        340        350        360
..........  .......... ..........  .......... ..........  ..........
```

FIG. 18B

```
          10         20         30         40         50         60
   ATGAATTGCA AAAGATTTTT CATAGCAAGT GCATTGATAT CACTAATGTC TTTCTTACCT
          70         80         90        100        110        120
   AGCGTATCTT TTTCTGAATC AATACATGAA GATAATATAA ATGGTAACTT TTACATTAGT
         130        140        150        160        170        180
   GCAAAGTATA TGCCAAGTGC CTCACACTTT GGCGTATTTT CAGTTAAAGA AGAGAAAAAC
         190        200        210        220        230        240
   ACAACAACTG GAGTTTTCGG ATTAAAACAA GATTGGGACG GAGCAACAAT AAAGGATGCA
         250        260        270        280        290        300
   AGCAGCAGCC ACACAATAGA CCCAAGTACA ATATTCTCCA TTTCAAATTA TTCATTTAAA
         310        320        330        340        350        360
   TATGAAAACA ATCCATTTTT AGGGTTTGCA GGAGCTATTG CTACTCAAT GGGTGGTCCA
         370        380        390        400        410        420
   AGGGTAGAGT TTGAAGTGTC TTACGAAATA TTTGATGTAA AAACCAAGG TAACAGTTAC
         430        440        450        460        470        480
   AAGAACGATG CTCACAAATA TTGCGCTTTA TCAAGACACA CCGGAGGTAT GCCACAAGCC
         490        500        510        520        530        540
   GGTCATCAAA ATAAATTTGT CTTCCTAAAA AATGAAGGAT TACTTGACAT ATCACTTATG
         550        560        570        580        590        600
   ATAAACGCAT GTTATGATAT AACAATCGAC AGCATGCCAT TTTCTCCATA TATATGTGCA
         610        620        630        640        650        660
   GGTATTGGTA GTGACTTAGT TTCGATGTTT GAAACTACAA ATCCTAAAAT TTCTTATCAA
         670        680        690        700        710        720
   GGAAAATTAG GTGTAAGTTA CTCCATAAGC CCAGAAGCAT CTGTTTTTGT TGGAGGACAC
         730        740        750        760        770        780
   TTTCACAGAG TTATAGGTAA TGAATTTAAA GACATTCCTG CAATAACTCC TGCTGGAGCA
         790        800        810        820        830        840
   ACAGAAATTA AAGGCACACA GTTTACAACA GTAACATTAA ACATATGCCA CTTCGGACTA
         850        860        870        880        890        900
   GAGCTTGGAG GCAGGTTTAC TTTTTAA...  ..........  ..........  ..........
```

FIG. 19A

```
          10         20         30         40         50         60
   MNCKRFFIAS ALISLMSFLP SVSFSESIHE DNINGNFYIS AKYMPSASHF GVFSVKEEKN
          70         80         90        100        110        120
   TTTGVFGLKQ DWDGATIKDA SSSHTIDPST IFSISNYSFK YENNPFLGFA GAIGYSMGGP
         130        140        150        160        170        180
   RVEFEVSYEI FDVKNQGNSY KNDAHKYCAL SRHTGGMPQA GHQNKFVFLK NEGLLDISLM
         190        200        210        220        230        240
   INACYDITID SMPFSPYICA GIGSDLVSMF ETTNPKISYQ GKLGVSYSIS PEASVFVGGH
         250        260        270        280        290        300
   FHRVIGNEFK DIPAITPAGA TEIKGTQFTT VTLNICHFGL ELGGRFTF.. ..........
```

FIG. 19B

```
          10          20          30          40          50          60
ATGAAATATA  AAAAAACTTT  TACAGTAACT  GCATTAGTAT  TATTAACTTC  CTTTACACAT
          70          80          90         100         110         120
TTTATACCTT  TTATAGTCC   AGCACGTGCC  AGTACAATTC  ACAACTTCTA  CATTAGTGGA
         130         140         150         160         170         180
AAATATATGC  CAACAGCGTC  ACATTTTGGA  ATTTTTTCAG  CTAAAGAAGA  ACAAAGTTTT
         190         200         210         220         230         240
ACTAAGGTAT  TAGTTGGGTT  AGATCAACGA  TTATCACATA  ATATTATAAA  CAATAATGAT
         250         260         270         280         290         300
ACAGCAAAGA  GTCTTAAGGT  TCAAAATTAT  TCATTTAAAT  ACAAAAATAA  CCCATTTCTA
         310         320         330         340         350         360
GGATTTGCAG  GAGCTATTGG  TTATTCAATA  GGCAATTCAA  GAATAGAACT  AGAAGTATCA
         370         380         390         400         410         420
CATGAAATAT  TTGATACTAA  AAACCCAGGA  ACAATTATT   TAAATGACTC  TCACAAATAT
         430         440         450         460         470         480
TGCGCTTTAT  CTCATGGAAG  TCACATATGC  AGTGATGGAA  ATAGCGGAGA  TTGGTACACT
         490         500         510         520         530         540
GCAAAAACTG  ATAAGTTTGT  ACTTCTGAAA  AATGAAGGTT  TACTTGACGT  CTCATTTATG
         550         560         570         580         590         600
TTAAACGCAT  GTTATGACAT  AACAACTGAA  AAAATGCCTT  TTTCACCTTA  TATATGTGCA
         610         620         630         640         650         660
GGTATTGGTA  CTGATCTCAT  ATCTATGTTT  GAGACAACAC  AAAACAAAAT  ATCTTATCAA
         670         680         690         700         710         720
GGAAAGTTAG  GTTTAAACTA  TACTATAAAC  TCAAGAGTTT  CTGTTTTTGC  AGGTGGGCAC
         730         740         750         760         770         780
TTTCATAAAG  TAATAGGTAA  TGAATTTAAA  GGTATTCCTA  CTCTATTACC  TGATGGATCA
         790         800         810         820         830         840
AACATTAAAG  TACAACAGTC  TGCAACAGTA  ACATTAGATG  TGTGCCATTT  CGGGTTAGAG
         850         860         870         880         890         900
ATTGGAAGTA  GATTTTTCTT  TTAA......  ..........  ..........  ..........
```

FIG. 20A

```
         10          20         30         40         50         60
MKYKKTFTVT ALVLLTSFTH FIPFYSPARA STIHNFYISG KYMPTASHFG IFSAKEEQSF
         70          80         90        100        110        120
TKVLVGLDQR LSHNIINNND TAKSLKVQNY SFKYKNNPFL GFAGAIGYSI GNSRIELEVS
        130         140        150        160        170        180
HEIFDTKNPG NNYLNDSHKY CALSHGSHIC SDGNSGDWYT AKTDKFVLLK NEGLLDVSFM
        190         200        210        220        230        240
LNACYDITTE KMPFSPYICA GIGTDLISMF ETTQNKISYQ GKLGLNYTIN SRVSVFAGGH
        250         260        270        280        290        300
FHKVIGNEFK GIPTLLPDGS NIKVQQSATV TLDVCHFGLE IGSRFFF... ..........
```

FIG. 20B

```
         10         20         30         40         50         60
ATGTTTTATA CTAATATATA TATTCTGGCT TGTATTTACT TTGCACTTCC ACTATTGTTA
         70         80         90        100        110        120
ATTTATTTTC ACTATTTTAG GTGTAATATG AATTGCAAAA AAATTCTTAT AACAACTGCA
        130        140        150        160        170        180
TTAATATCAT TAATGTACTC TATTCCAAGC ATATCTTTTT CTGATACTAT ACAAGATGGT
        190        200        210        220        230        240
AACATGGGTG GTAACTTCTA TATTAGTGGA AAGTATGTAC CAAGTGTCTC ACATTTTGGT
        250        260        270        280        290        300
AGCTTCTCAG CTAAAGAAGA AAGCAAATCA ACTGTTGGAG TTTTTGGATT AAAACATGAT
        310        320        330        340        350        360
TGGGATGGAA GTCCAATACT TAAGAATAAA CACGCTGACT TTACTGTTCC AAACTATTCG
        370        380        390        400        410        420
TTCAGATACG AGAACAATCC ATTTCTAGGG TTTGCAGGAG CTATCGGTTA CTCAATGGGT
        430        440        450        460        470        480
GGCCCAAGAA TAGAATTCGA AATATCTTAT GAAGCATTCG ACGTAAAAAG TCCTAATATC
        490        500        510        520        530        540
AATTATCAAA ATGACGCGCA CAGGTACTGC GCTCTATCTC ATCACACATC GGCAGCCATG
        550        560        570        580        590        600
GAAGCTGATA AATTTGTCTT CTTAAAAAAC GAAGGGTTAA TTGACATATC ACTTGCAATA
        610        620        630        640        650        660
AATGCATGTT ATGATATAAT AAATGACAAA GTACCTGTTT CTCCTTATAT ATGCGCAGGT
        670        680        690        700        710        720
ATTGGTACTG ATTTGATTTC TATGTTTGAA GCTACAAGTC CTAAAATTTC CTACCAAGGA
        730        740        750        760        770        780
AAACTGGGCA TTAGTTACTC TATTAATCCG GAAACCTCTG TTTTCATCGG TGGGCATTTC
        790        800        810        820        830        840
CACAGGATCA TAGGTAATGA GTTTAGAGAT ATTCCTGCAA TAGTACCTAG TAACTCAACT
        850        860        870        880        890        900
ACAATAAGTG GACCACAATT TGCAACAGTA ACACTAAATG TGTGTCACTT TGGTTTAGAA
        910        920        930        940        950        960
CTTGGAGGAA GATTTAACTT CTAA......  .........  .........  .........
```

FIG. 21A

```
          10         20         30         40         50         60
   MFYTNIYILA CIYFALPLLL IYFHYFRCNM NCKKILITTA LISLMYSIPS ISFSDTIQDG
          70         80         90        100        110        120
   NMGGNFYISG KYVPSVSHFG SFSAKEESKS TVGVFGLKHD WDGSPILKNK HADFTVPNYS
         130        140        150        160        170        180
   FRYENNPFLG FAGAIGYSMG GPRIEFEISY EAFDVKSPNI NYQNDAHRYC ALSHHTSAAM
         190        200        210        220        230        240
   EADKFVFLKN EGLIDISLAI NACYDIINDK VPVSPYICAG IGTDLISMFE ATSPKISYQG
         250        260        270        280        290        300
   KLGISYSINP ETSVFIGGHF HRIIGNEFRD IPAIVPSNST TISGPQFATV TLNVCHFGLE
         310        320        330        340        350        360
   LGGRFNF... .......... .......... .......... .......... ..........
```

FIG. 21B

```
         10         20         30         40         50         60
ATGAATTGCA AAAAAATTCT TATAACAACT GCATTAATGT CATTAATGTA CTATGCTCCA
         70         80         90        100        110        120
AGCATATCTT TTTCTGATAC TATACAAGAC GATAACACTG GTAGCTTCTA CATCAGTGGA
        130        140        150        160        170        180
AAATATGTAC CAAGTGTTTC ACATTTGGT GTTTTCTCAG CTAAAGAAGA AAGAAACTCA
        190        200        210        220        230        240
ACTGTTGGAG TTTTTGGATT AAAACATGAT TGGAATGGAG GTACAATATC TAACTCTTCT
        250        260        270        280        290        300
CCAGAAAATA TATTCACAGT TCAAAATTAT TCGTTTAAAT ACGAAAACAA CCCATTCTTA
        310        320        330        340        350        360
GGGTTTGCAG GAGCTATTGG TTATTCAATG GGTGGCCCAA GAATAGAACT TGAAGTTCTG
        370        380        390        400        410        420
TACGAGACAT TCGATGTGAA AAATCAGAAC AATAATTATA AGAACGGCGC ACACAGATAC
        430        440        450        460        470        480
TGTGCTTTAT CTCATCATAG TTCAGCAACA AACATGTCCT CCGCAAGTAA CAAATTTGTT
        490        500        510        520        530        540
TTCTTAAAAA ATGAAGGGTT AATTGACTTA TCATTTATGA TAAATGCATG CTATGACATA
        550        560        570        580        590        600
ATAATTGAAG GAATGCCTTT TTCACCTTAT ATTTGTGCAG GTGTTGGTAC TGATGTTGTT
        610        620        630        640        650        660
TCCATGTTTG AAGCTATAAA TCCTAAAATT TCTTACCAAG GAAAACTAGG ATTAGGTTAT
        670        680        690        700        710        720
AGTATAAGTT CAGAAGCCTC TGTTTTTATC GGTGGACACT TTCACAGAGT CATAGGTAAT
        730        740        750        760        770        780
GAATTTAGAG ACATCCCTGC TATGGTTCCT AGTGGATCAA ATCTTCCAGA AAACCAATTT
        790        800        810        820        830        840
GCAATAGTAA CACTAAATGT GTGTCACTTT GGTTTAGAAC TTGGAGGAAG ATTTAACTTC
        850        860        870        880        890        900
TGA.......  .........  .........  .........  .........  .........
```

FIG. 22A

```
         10         20         30         40         50         60
MNCKKILITT ALMSLMYYAP SISFSDTIQD DNTGSFYISG KYVPSVSHFG VFSAKEERNS
         70         80         90        100        110        120
TVGVFGLKHD WNGGTISNSS PENIFTVQNY SFKYENNPFL GFAGAIGYSM GGPRIELEVL
        130        140        150        160        170        180
YETFDVKNQN NNYKNGAHRY CALSHHSSAT NMSSASNKFV FLKNEGLIDL SFMINACYDI
        190        200        210        220        230        240
IIEGMPFSPY ICAGVGTDVV SMFEAINPKI SYQGKLGLGY SISSEASVFI GGHFHRVIGN
        250        260        270        280        290        300
EFRDIPAMVP SGSNLPENQF AIVTLNVCHF GLELGGRFNF .......... ..........
```

*FIG. 22B*

```
         10         20         30         40         50         60
ATGAATTGTA AAAAAGTTTT CACAATAAGT GCATTGATAT CATCCATATA CTTCCTACCT
         70         80         90        100        110        120
AATGTCTCAT ACTCTAACCC AGTATATGGT AACAGTATGT ATGGTAATTT TTACATATCA
        130        140        150        160        170        180
GGAAAGTACA TGCCAAGTGT TCCTCATTTT GGAATTTTTT CAGCTGAAGA AGAGAAAAAA
        190        200        210        220        230        240
AAGACAACTG TAGTATATGG CTTAAAAGGA AAACTGGCAG GAGATGCAAT ATCTAGTCAA
        250        260        270        280        290        300
AGTCCAGATG ATAATTTTAC CATTCGAAAT TACTCATTCA AGTATGCAAG CAACAAGTTT
        310        320        330        340        350        360
TTAGGGTTTG CAGTAGCTAT TGGTTACTCG ATAGGCAGTC CAAGAATAGA AGTTGAGATG
        370        380        390        400        410        420
TCTTATGAAG CATTTGATGT GAAAAATCCA GGTGATAATT ACAAAAACGG TGCTTACAGG
        430        440        450        460        470        480
TATTGTGCTT TATCTCATCA AGATGATGCG GATGATGACA TGACTAGTGC AACTGACAAA
        490        500        510        520        530        540
TTTGTATATT TAATTAATGA AGGATTACTT AACATATCAT TTATGACAAA CATATGTTAT
        550        560        570        580        590        600
GAAACAGCAA GCAAAAATAT ACCTCTCTCT CCTTACATAT GTGCAGGTAT TGGTACTGAT
        610        620        630        640        650        660
TTAATTCACA TGTTTGAAAC TACACATCCT AAAATTTCTT ATCAAGGAAA GCTAGGGTTG
        670        680        690        700        710        720
GCCTACTTCG TAAGTGCAGA GTCTTCGGTT TCTTTTGGTA TATATTTTCA TAAAATTATA
        730        740        750        760        770        780
AATAATAAGT TTAAAAATGT TCCAGCCATG GTACCTATTA ACTCAGACGA GATAGTAGGA
        790        800        810        820        830        840
CCACAGTTTG CAACAGTAAC ATTAAATGTA TGCTACTTTG GATTAGAACT TGGATGTAGG
        850        860        870        880        890        900
TTCAACTTCT AA........ .......... .......... .......... ..........
```

FIG. 23A

```
         10         20         30         40         50         60
MNCKKVFTIS ALISSIYFLP NVSYSNPVYG NSMYGNFYIS GKYMPSVPHF GIFSAEEEKK
         70         80         90        100        110        120
KTTVVYGLKG KLAGDAISSQ SPDDNFTIRN YSFKYASNKF LGFAVAIGYS IGSPRIEVEM
        130        140        150        160        170        180
SYEAFDVKNP GDNYKNGAYR YCALSHQDDA DDDMTSATDK FVYLINEGLL NISFMTNICY
        190        200        210        220        230        240
ETASKNIPLS PYICAGIGTD LIHMFETTHP KISYQGKLGL AYFVSAESSV SFGIYFHKII
        250        260        270        280        290        300
NNKFKNVPAM VPINSDEIVG PQFATVPLKV CYFGLELGCR FNF.......  ..........
```

FIG. 23B

```
         10         20         30         40         50         60
ATGAACTGTA AAAAAATTCT TATAACAACT ACATTGGTAT CACTAACAAT TCTTTTACCT
         70         80         90        100        110        120
GGCATATCTT TCTCCAAACC AATACATGAA AACAATACTA CAGGAAACTT TTACATTATT
        130        140        150        160        170        180
GGAAAATATG TACCAAGTAT TTCACATTTT GGGAACTTTT CAGCTAAAGA AGAAAAAAAC
        190        200        210        220        230        240
ACAACAACTG GAATTTTTGG ATTAAAAGAA TCATGGACTG GTGGTATCAT CCTTGATAAA
        250        260        270        280        290        300
GAACATGCAG CTTTTAATAT CCCAAATTAT TCATTTAAAT ATGAAAATAA TCCATTTTTA
        310        320        330        340        350        360
GGATTTGCAG GGGTAATTGG CTATTCAATA GGTAGTCCAA GAATAGAATT TGAAGTATCA
        370        380        390        400        410        420
TACGAGACAT TCGATGTACA AAATCCAGGA GATAAGTTTA ACAATGATGC ACATAAGTAT
        430        440        450        460        470        480
TGTGCTTTAT CCAATGATTC CAGTAAAACA ATGAAAAGTG GTAAATTCGT TTTTCTCAAA
        490        500        510        520        530        540
AATGAAGGAT TAAGTGACAT ATCACTCATG TTAAATGTAT GTTATGATAT AATAAACAAA
        550        560        570        580        590        600
AGAATGCCTT TTTCACCTTA CATATGTGCA GGCATTGGTA CTGACTTAAT ATTCATGTTT
        610        620        630        640        650        660
GACGCTATAA ACCATAAAGC TGCTTATCAA GGAAAATTAG GTTTTAATTA TCCAATAAGC
        670        680        690        700        710        720
CCAGAAGCTA ACATTTCTAT GGGTGTGCAC TTTCACAAAG TAACAAACAA CGAGTTTAGA
        730        740        750        760        770        780
GTTCCTGTTC TATTAACTGC TGGAGGACTC GCTCCAGATA ATCTATTTGC AATAGTAAAG
        790        800        810        820        830        840
TTGAGTATAT GTCATTTTGG GTTAGAATTT GGGTACAGGG TCAGTTTTTA A.........
```

FIG. 24A

```
         10         20         30         40         50         60
MNCKKILITT TLVSLTILLP GISFSKPIHE NNTTGNFYII GKYVPSISHF GNFSAKEEKN
         70         80         90        100        110        120
TTTGIFGLKE SWTGGIILDK EHAAFNIPNY SFKYENNPFL GFAGVIGYSI GSPRIEFEVS
        130        140        150        160        170        180
YETFDVQNPG DKFNNDAHKY CALSNDSSKT MKSGKFVFLK NEGLSDISLM LNVCYDIINK
        190        200        210        220        230        240
RMPFSPYICA GIGTDLIFMF DAINHKAAYQ GKLGFNYPIS PEANISMGVH FHKVTNNEFR
        250        260        270        280        290        300
VPVLLTAGGL APDNLFAIVK LSICHFGLEF GYRVSF....　..........　..........
```

FIG. 24B

```
          10         20         30         40         50         60
   ATGAATAATA AACTCAAATT TACTATAACA AACACAGTAT TAGTATGCTT ATTGTCATTA
          70         80         90        100        110        120
   CCTAATATAT CTTCCTCAAA GGCCATAAAC AATAACGCTA AAAAGTACTA CGGATTATAT
         130        140        150        160        170        180
   ATCAGTGGAC AATATAAACC CAGTGTTTCT GTTTTCAGTA ATTTTTCAGT TAAAGAAACC
         190        200        210        220        230        240
   AATGTCATAA CTAAAAACCT TATAGCTTTA AAAAAAGATG TTGACTCTAT TGAAACCAAG
         250        260        270        280        290        300
   ACTGATGCCA GTGTAGGTAT TAGTAACCCA TCAAATTTTA CTATCCCCTA TACAGCTGTA
         310        320        330        340        350        360
   TTTCAAGATA ATTCTGTCAA TTTCAATGGA ACTATTGGTT ACACCTTTGC TGAAGGTACA
         370        380        390        400        410        420
   AGAGTTGAAA TAGAAGGTTC TTATGAGGAA TTTGATGTTA AAAACCCTGG AGGCTATACA
         430        440        450        460        470        480
   CTAAGTGATG CCTATCGCTA TTTTGCATTA GCACGTGAAA TGAAAGGTAA TAGTTTTACA
         490        500        510        520        530        540
   CCTAAAGAAA AAGTTTCTAA TAGTATTTTT CACACTGTAA TGAGAAATGA TGGATTATCT
         550        560        570        580        590        600
   ATAATATCTG TTATAGTAAA TGTTTGCTAC GATTTCTCTT TGAACAATTT GTCAATATCG
         610        620        630        640        650        660
   CCTTACATAT GTGGAGGAGC AGGGGTAGAT GCTATAGAAT TCTTCGATGT ATTACACATT
         670        680        690        700        710        720
   AAGTTTGCAT ATCAAAGCAA GCTAGGTATT GCTTATTCTC TACCATCTAA CATTAGTCTC
         730        740        750        760        770        780
   TTTGCTAGTT TATATTACCA TAAAGTAATG GGCAATCAAT TTAAAAATTT AAATGTCCAA
         790        800        810        820        830        840
   CATGTTGCTG AACTTGCAAG TATACCTAAA ATTACATCCG CAGTTGCTAC ACTTAATATT
         850        860        870        880        890        900
   GGTTATTTTG GAGGTGAAAT TGGTGCAAGA TTGACATTTT AA........ ..........
```

FIG. 25A

```
         10         20         30         40         50         60
MNNKLKFTII NTVLVCLLSL PNISSSKAIN NNAKKYYGLY ISGQYKPSVS VFSNFSVKET
         70         80         90        100        110        120
NVITKNLIAL KKDVDSIETK TDASVGISNP SNFTIPYTAV FQDNSVNFNG TIGYTFAEGT
        130        140        150        160        170        180
RVEIEGSYEE FDVKNPGGYT LSDAYRYFAL AREMKGNSFT PKEKVSNSIF HTVMRNDGLS
        190        200        210        220        230        240
IISVIVNVCY DFSLNNLSIS PYICGGAGVD AIEFFDVLHI KFAYQSKLGI AYSLPSNISL
        250        260        270        280        290        300
FASLYYHKVM GNQFKNLNVQ HVAELASIPK ITSAVATLNI GYFGGEIGAR LTF.......
```

FIG. 25B

```
         10         20         30         40         50         60
ATGGCAAATT TTATGTACAA AAAATACAAA CTAATGACAG CAGGTGTAGT ATTATTTCAC
         70         80         90        100        110        120
ATGTTATTTC TACCTCATGT TTCTTTCGCA AAAAATACAA ACAGCAATAA ACTTGGATTA
        130        140        150        160        170        180
TACATCAGTG GACAGTATAA CCCTAGTGTT TCTGTTTTTA GCAATTTTTC AGCAAAAGAA
        190        200        210        220        230        240
ACCAATGTTC ATACAGTACA ACTCATGGCG CTTAAAAAAG ACATTGATTC TATTGAAGTT
        250        260        270        280        290        300
GATACTGGAA ATAGCGCAGG TATTAGCAAA CCACAAAATT TCACAGTTCT TTATACTCCA
        310        320        330        340        350        360
AAATTTCAAG ATAATGTTGC TGGTCTTAGC GGTGCACTTG GATTCTTTTA TTCTAAAGGA
        370        380        390        400        410        420
TTAAGGATTG AAATGGGGTT TTCTTATGAA AAATTTGATG CTAAAGACCT TGGTGAGTAC
        430        440        450        460        470        480
ACCAAAATAA AAGATGCTTA TAGATATTTT GCTCTAGTAC GTGAAATGCA TGTTAGTCTC
        490        500        510        520        530        540
ATTTATCCAA AAGATAATAA CACAGGAACA CATTATACTG TTATGAGAAA TGATGGTATA
        550        560        570        580        590        600
TCTATTTCTT CTGCTACAGT AAATGGCTGC TATGATTCTT TTTTCCAGTT TATCTTTGTC
        610        620        630        640        650        660
ACCTATATGT GTATAGGCAT CGGTATAGAT GCTATAGAAT TTCTTAATGC ATACATATTA
        670        680        690        700        710        720
AGTTTGCTTG CCAAGGTAGT TAAGTGTTTA ACTPATTCTG TATCTCCCAA TGTTAATTTA
        730        740        750        760        770        780
TTTGCAGATG GATATTATCA TAAAGTGATG GGCAATAAAT TTAAAAATTT ACCTGTTCAA
        790        800        810        820        830        840
TACGTTAATA CTTTAGAAGA GTATCCAAGA GTTACATCTG CAATTGCTAC ACTTGATATT
        850        860        870        880        890        900
GGCTACCTCG GTGGTGAAAT TGGCATAAGA TTTATATTTT AA........ ..........
```

FIG. 26A

```
         10         20         30         40         50         60
MANFMYKKYK LMTAGVVLFH MLFLPHVSFA KNTDSNKLGL YISGQYNPSV SVFSNFSAKE
         70         80         90        100        110        120
TNVHTVQLMA LKKDIDSIEV DTGNSAGISK PQNETVLYTP KFQDNVAGLS GALGFFYSKG
        130        140        150        160        170        180
LRIEMGFSYE KFDAKDLGEY TKIKDAYRYF ALVREMHVSL IYPKDNNTGT HYTVMRNDGI
        190        200        210        220        230        240
SISSATVNGC YDSFFQFIFV TYMCIGIGID AIEFLNAYIL SLLAKVVKVL TYSVSPNVNL
        250        260        270        280        290        300
FADGYYHKVM GNKFKNLPVQ YVNTIEEYPR VTSAIATLDI GYLGGEIGIR FIF.......
```

FIG. 26B

```
         10         20         30         40         50         60
ATGGGAAATT CTATGAATAA TAAAAGTCAA TTCTTAATAA GATTTATATT TTTAACATGC
         70         80         90        100        110        120
ATGCTGTCAT TACCTAATAT ATCTCCTTCA AAAGTAAATA ACGAAAAACA TTCTGGTTTG
        130        140        150        160        170        180
TATATTAGCG GGCAATACAA ACCCAGTGTT TCTGTTTTCA GTAATTTTTC AGTTAAAGAA
        190        200        210        220        230        240
ACCAACTTTC ATACAAAACA TCTCATAGCT CTTAAACAAG ATGTTGATTC TGTTGAAATT
        250        260        270        280        290        300
GATACTGGTA GTAATACAGC AGGTATTAGT AACCCATCTA ACTTTACAAT CCCTTATACT
        310        320        330        340        350        360
GCAGAATTTC AAGACAACCA TACTAACTGC AATGGCTCTA TTGGTTATGC TTTTGCTGAA
        370        380        390        400        410        420
GGTCCAAGAA TTGAAATAGA ATTATCATAT GAAAAATTTG ATGTTAAAAA TCCCACAGGG
        430        440        450        460        470        480
TATACTACAG TAAAAGATGC TTATAGATAC TTTGCTTTAG CACGTGAAAT AAATATTTCT
        490        500        510        520        530        540
CTATTCCAAC CAAAACAAAA AGAAGGTAGT GGAATTTACC ATGTCGTAAT GAAAACGAT
        550        560        570        580        590        600
GGGTTATCTA TCTTATCCAA TATAGTTAAT ATTTGCTACG ATTTTTCTTT AAATAATTTA
        610        620        630        640        650        660
CCTATATCAC CTTATTTATG CGGAGGAATG GGTATAAATG CCATAGAATT CTTTGACGCT
        670        680        690        700        710        720
TTACATGTGA AATTTGCTTA TCAAAGCAAG GCAGGAATTA GTTATCAACT ATTACGTAAA
        730        740        750        760        770        780
ATCAACTTAT TTATTGATGT ATATTACTAC GAAGTAATAA GTAATAAATT TAAAAACCTG
        790        800        810        820        830        840
AAAGTCCAAC ATGTACATGA ACTTAAAGAT AATCCAAAAG TCACATCTGC AGTTGCTACA
        850        860        870        880        890        900
CTTGATATAG CATATTTTGG TAGTGAAGCT GGCATAAGAA TTATATTTTA A.........
```

FIG. 27A

```
         10         20         30         40         50         60
MGNSMNNKSQ FLIRFIFLTC MLSLPNISLS KVNNEKHSGL YISGQYKPSV SVFSNFSVKE
         70         80         90        100        110        120
TNFHTKHLIA LKQDVDSVEI DTGSNTAGIS NPSNFTIPYT AEFQDNHTNC NGSIGYAFAE
        130        140        150        160        170        180
GPRIEIELSY EKFDVKNPTG YTTVKDAYRY FALAREINIS LFQPKQKEGS GIYHVVMKND
        190        200        210        220        230        240
GLSILSNIVN ICYDFSLNNL PISPYLCGGM GINAIEFFDA LHVKFAYQSK AGISYQLLRK
        250        260        270        280        290        300
INLFIDVYYY EVISNKFKNL KVQHVHELKD NPKVTSAVAT LDIAYFGSEA GIRIIF....
```

FIG. 27B

```
         10         20         30         40         50         60
ATGAATAGCA AGAGTAAGTT CTTTACAATA TGTACATCGT TAATATGCTT ATTATCATCA
         70         80         90        100        110        120
CCTAACACAT CTCTCTCAAA CTTCATAGGC AATAGTACAA AACATTCTGG ATTATATGTT
        130        140        150        160        170        180
AGCGGACAAT ATAAGCCCAG CGTTTCCATT TTTAGCAAAT TTTCAGTAAA AGAAACAAAT
        190        200        210        220        230        240
ACACATACAG TACAGTTAGT AGCTCTTAAA AAAGATGTTA ATTCTATTTC TATGAACATC
        250        260        270        280        290        300
AGTAATGGTG CTACAGGCAT TAGCAAAGCA ACAAATTTTA ATCTTCCTTA TGTTGCAGAA
        310        320        330        340        350        360
TTTCAAGACA ATGCCTTCAA CTTCAGTGGA GCTATTGGTT ATTCACTTTT TGAACAACTA
        370        380        390        400        410        420
AACATTGAAG TTGAAGGTTC TTATGAAGAA TTCGATGCCA AAAATCCTGG TGGTTATATT
        430        440        450        460        470        480
TTAAATGATG CATTCCGCTA TTTTGCATTG GCACGTGAAA TGGGACAAGA AAAAAATGAT
        490        500        510        520        530        540
AATAAGCATC TTAGTCCTAA GGAGGAGCAT GATATAAGTA AAACATATTA CACAGTCATG
        550        560        570        580        590        600
AGAAATAATG GGTTATCTAT ATTATCTATT ATGATAAATG GCTGCTATAA TCTACCTCTC
        610        620        630        640        650        660
AATGATTTAT CAATATCACC TTATTTTTGT ACAGGAATAG GTGTAGATGC TATAGAATTT
        670        680        690        700        710        720
TTTGATGCAC TGCATCTTAA ACTTGCTTTG CAAAGTAAAA TAGGAGCTAC TTACCAATTA
        730        740        750        760        770        780
TCAGACAACA TTAGTTTATT TACAAATGGA TATTACCATC AAGTAATAGG TGATCAATTT
        790        800        810        820        830        840
AAAAACTTAA AAGTCCAATA TATAGGTGAA CTTAAAGAGA ACCCGAAAAT TACATCTGCA
        850        860        870        880        890        900
GTTGCTACTC TCAATGTTGG ATACTTTGGA GGTGAAATTG GAGTAAGACT CACACTTTAA
        910        920        930        940        950        960
.......... .......... .......... .......... .......... ..........
```

*FIG. 28A*

```
         10         20         30         40         50         60
MNSKSKFFTI CTSLICLLSS PNTSLSNFIG NSTKHSGLYV SGQYKPSVSI FSKFSVKETN
         70         80         90        100        110        120
THTVQLVALK KDVNSISMNI SNGATGISKA TNENLPYVAE FQDNAFNFSG AIGYSLFEQL
        130        140        150        160        170        180
NIEVEGSYEE FDAKNPGGYI LNDAFRYFAL AREMGQEKND NKHLSPKEEH DISKTYYTVM
        190        200        210        220        230        240
RNNGLSILSI MINGCYNLPL NDLSISPYFC TGIGVDAIEF FDALHLKLAL QSKIGATYQL
        250        260        270        280        290        300
SDNISLFTNG YYHQVIGDQF KNLKVQYIGE LKENPKITSA VATLNVGYFG GEIGVRLTL.
```

FIG. 28B

```
        10         20         30         40         50         60
ATGAATAATA AAAGAAATTT TTTTTTAATA GGTATGTCTC TATTGATAAA TCTACTATTG
        70         80         90,       100        110        120
CCAATTGATG CCTCTTCTAT GGAAGTACAT AATTATACAC ATTTTACACC TAGGCTGTAT
       130        140        150        160        170        180
ATTAGTGGGC AATACAGGCC AGGAGTTTCC CACTTTAGCA AATTTTCAGT CAAAGAAACA
       190        200        210        220        230        240
CATTGTAATA CTGTGCAATT AGTTGGGCTA ACAAAAGATA TAAAAGTAAC TAATAACAGT
       250        260        270        280        290        300
AGTATCAACA CAAATACTAG TTTTAACTTT CCTTATGTTG CAGAATTTCA AGATAACGCA
       310        320        330        340        350        360
ATGAGCTTTA GTGGAGCAAT AGGATGCTTT TATTCAGAAC ACTTCAGAAT TGAAGTAGAA
       370        380        390        400        410        420
GCTTCTTATG AAGAATTTGA CGTTAAAAAT CCTGAAGGAT CTACTACAGA CTCCTATAGA
       430        440        450        460        470        480
TATTTCGCGT TAGCACGTGG CATGGATGGT AATAATATTC CTACAAGTCA AAAATTTACT
       490        500        510        520        530        540
GTAATGAGAA ACGACGGGTT ATTAATCTCA TCTGTTATGA TAAATGGCTG TTACAATGTC
       550        560        570        580        590        600
ATACTAAATG ATATACAAGC AGAACCTTAC ATATGTGCAG GACTAGGAGG AGATTTTATA
       610        620        630        640        650        660
GAATTCTTCA ATGGCTTTCA TGTTAAGCTA GCTTATCAAG GTAAAGTAGG CATTAGTTAT
       670        680        690        700        710        720
CAAATATTCC CTGAAGTAAG ATTATTTATT GATGGATACT ACCATAAAGT AAAAGGCAAC
       730        740        750        760        770        780
AAGTTTAAAA ATTTACACGT TCAACATGTA GGTGCACTTG CAGCACTCCC TAAAGTTACA
       790        800        810        820        830        840
TCTGCAGTTG CAACACTTAA TATTGGATAC TTTGGTTGTG AAGCTGGAGT AAGATTCATA
       850        860        870        880        890        900
TTTTAA....  .........  .........  .........  ..........  .......
```

FIG. 29A

```
         10         20         30         40         50         60
MNNKRNFFLI GMSLLINLLL PIDASSMEVH NYTHFTPRLY ISGQYRPGVS HFSKFSVKET
         70         80         90        100        110        120
HCNTVQLVGL TKDIKVTNNS SINTNTSFNF PYVAEFQDNA MSFSGAIGCF YSEHFRIEVE
        130        140        150        160        170        180
ASYEEFDVKN PEGSTTDSYR YFALARGMDG NNIPTSQKFT VMRNDGLLIS SVMINGCYNV
        190        200        210        220        230        240
ILNDIQAEPY ICAGLGGDFI EFFNGFHVKL AYQGKVGISY QIFPEVRLFI DGYYHKVKGN
        250        260        270        280        290        300
KFKNLHVQHV GALAALPKVT SAVATLNIGY FGCEAGVRFI F.......... ..........
```

FIG. 29B

```
        10         20         30         40         50         60
ATGAATTATA AGAAAATTCT AGTAAGAAGC GCGTTAATCT CATTAATGTC AATCTTACCA
        70         80         90        100        110        120
TATCAGTCTT TTGCAGATCC TGTAGGTTCA AGAACTAATG ATAACAAAGA AGGCTTCTAC
       130        140        150        160        170        180
ATTAGTGCAA AGTACAATCC AAGTATATCA CACTTTAGAA AATTCTCTGC TGAAGAAACT
       190        200        210        220        230        240
CCTATTAATG GAACAAATTC TCTCACTAAA AAAGTTTTCG GACTAAAGAA AGATGGTGAT
       250        260        270        280        290        300
ATAACAAAAA AAGACGATTT TACAAGAGTA GCTCCAGGCA TTGATTTTCA AAATAACTTA
       310        320        330        340        350        360
ATATCAGGAT TTTCAGGAAG TATTGGTTAC TCTATGGACG GACCAAGAAT AGAACTTGAA
       370        380        390        400        410        420
GCTGCATATC AACAATTTAA TCCAAAAAAC ACCGATAACA ATGATACTGA TAATGGTGAA
       430        440        450        460        470        480
TACTATAAAC ATTTTGCATT ATCTCGTAAA GATGCAATGG AAGATCAGCA ATATGTAGTA
       490        500        510        520        530        540
CTTAAAAATG ACGGCATAAC TTTTATGTCA TTGATGGTTA ATACTTGCTA TGACATTACA
       550        560        570        580        590        600
GCTGAAGGAG TATCTTTCGT ACCATATGCA TGTGCAGGTA TAGGAGCAGA TCTTATCACT
       610        620        630        640        650        660
ATTTTTAAAG ACCTCAATCT AAAATTTGCT TACCAAGGAA AAATAGGTAT TAGTTACCCT
       670        680        690        700        710        720
ATCACACCAG AAGTCTCTGC ATTTATTGGT GGATACTACC ATGGCGTTAT TGGTAATAAA
       730        740        750        760        770        780
TTTGAGAAGA TACCTGTAAT AACTCCTGTA GTATTAAATG ATGCTCCTCA AACCACATCT
       790        800        810        820        830        840
GCTTCAGTAA CTCTTGACGT TGGATACTTT GGCGGAGAAA TTGGAATGAG GTTCACCTTC
       850        860        870        880        890        900
TAA....... .......... .......... .......... .......... ..........
```

FIG. 30A

```
         10         20         30         40         50         60
MNYKKILVRS ALISLMSILP YQSFADPVGS RTNDNKEGFY ISAKYNPSIS HFRKFSAEET
         70         80         90        100        110        120
PINGTNSLTK KVFGLKKDGD ITKKDDFTRV APGIDFQNNL ISGFSGSIGY SMDGPRIELE
        130        140         50        160        170        180
AAYQQFNPKN TDNNDTDNGE YYKHFALSRK DAMEDQQYVV LKNDGITFMS LMVNTCYDIT
        190        200        210        220        230        240
AEGVSFVPYA CAGIGADLIT IFKDLNIKFA YQGKIGISYP ITPEVSAFIG GYYHGVIGNK
        250        260        270        280        290        300
FEKIPVITPV VLNDAPQTTS ASVTLDVGYF GGEIGMRFTF .......... ..........
```

FIG. 30B

```
          10         20         30         40         50         60
ATGAACAAAA AGAAAATTAT TACAGTAGGA ACAACATTAG CTTATTTATT ATTATCACCT
          70         80         90        100        110        120
AACATATCTT TTTCAGAAGT AATCAACAAT GATACTGATA AATATTCTAG ACTATATATA
         130        140        150        160        170        180
AGTGGTCAAT ATAAACCAGG ATTTTCTTAT TTTAATAAGT CTCAGTTAG AGAAACTGAT
         190        200        210        220        230        240
CATTTCACTA AAGCATTAAT AGGATTAAGA CATGACGCAA TATCTACTAA AAATTTAACA
         250        260        270        280        290        300
ACTAATACAG ATTTCAATAC TCTTTATAAA GTAACATTTC AAAACAACAT CATTAGCTTT
         310        320        330        340        350        360
AGCGGTGCTA TTGGTTATTC TGATAGCACA GGTGTAAGGT TTGAGCTAGA AGGCTCTTAT
         370        380        390        400        410        420
GAAGAGTTCG ATGTTACAGA CCCTGGAGAT TGTATAATAA AAGATACTTA CAGGTACTTT
         430        440        450        460        470        480
GCATTAGCTA GAAAAACAAG TGGTAATCAT CCCAACGATA ATGGGGAATA TACTGTCATG
         490        500        510        520        530        540
AGAAATGATG GAGTATCCAT TACCTCCGTT ATATTCAATG GTTGTTATGA TCTCTCTTTA
         550        560        570        580        590        600
AAAGAGCTAG AAATATCACC ATATGTTTGC ATTGGTATCG GAGGAGACTT TATAGAATTT
         610        620        630        640        650        660
TTTGATGCTT TACACATTAA ATTAGCATAT CAAGGTAAAC TAGGTATTAG CTATTCTTTT
         670        680        690        700        710        720
TCCACTAGAA CAAATTTATT TATCGATTGT TATTACCATA GAGTTATAGG TAATCAATTT
         730        740        750        760        770        780
AATAATTTAA ATGTTCAACA TGTAGTTGAG CTTACAGAAG CACCTAAAGC TACATCTGCA
         790        800        810        820        830        840
ATTGCTACAC TTAATGTTAG TTACTTCGGT GGAGAAGTTG GAATTAGACT TATGTTTTAA
         850        860        870        880        890        900
.......... .......... .......... .......... .......... ..........
```

*FIG. 31A*

```
         10         20         30         40         50         60
MNKKKIITVG TTLAYLLLSP NISFSEVINN DTDKYSRLYI SGQYKPGFSY FNKFSVRETD
         70         80         90        100        110        120
HFTKALIGLR HDAISTKNLT TNTDFNTLYK VTFQNNIISF SGAIGYSDST GVRFELEGSY
        130        140        150        160        170        180
EEFDVTDPGD CIIKDTYRYF ALARKTSGNH PNDNGEYTVM RNDGVSITSV IFNGCYDLSL
        190        200        210        220        230        240
KELEISPYVC IGIGGDFIEF FDALHIKLAY QGKLGISYSF STRTNLFIDC YYHRVIGNQF
        250        260        270        280        290        300
NNLNVQHVVE LTEAPKATSA IATLNVSYFG GEVGIRLMF. .......... ..........
```

*FIG. 31B*

```
          10         20         30         40         50         60
     CCCGTCGTTT CTCATTACAG TGACTTTTCA ATTAAAGAAA CTTATACTAA CACTGAGGCA
          70         80         90        100        110        120
     TTGTTTGGGC TAAAACAAGA TATTAGTTCT ATTTTACGTA ATAAAGAGAC CACACAATAT
         130        140        150        160        170        180
     AATAACAATT TTAACGTTCC CTATACTGCA AAATTTCAAG ACGACTTTGC GAGTTTCAGC
         190        200        210        220        230        240
     ATAGCTGTTG GATATATTGC TAACAATGGT CCAAGAATTG AAATAGAAGG ATCTTACGAA
         250        260        270        280        290        300
     GAATTTGATG TTAAAAACCC AGGAAATTAT ACAACAATAG ATGCTCATAG GTACATTGCT
         310        320        330        340        350        360
     TTAGCTAGAG AAAAAACTTC TTACTATCTA AGTTCTCCTA AAGAAAACAA ATATGTAATT
         370        380        390        400        410        420
     ATAAAGAATA ACGGCATATC TATTGTATCT ATTATAATTA ATGGTTGTTA TGATATTTCT
         430        440        450        460        470        480
     TTAAATGATT CTAAGGTGTC ACCTTACATA TGCACAGGGT TTGGTGGAGA TTTTATAGAG
         490        500        510        520        530        540
     TTTTTTAGTG CTATACGTTT TAACTTTGCT TATCAAGGTA AAATAGGTAT CAGTTATTCA
         550        560        570        580        590        600
     TTATCTTCTA ACATAATTTT ATTTACTGAT GGATATTACC ACAAGGTAAT AAATTCCCAA
         610        620        630        640        650        660
     TTTAAAAATT TAAATGTTGA ACATGTTGTT AATGAGTTAA CTACAGATCC TAAAGTGACT
         670        680        690        700        710        720
     TCTGCAACAG CATTTCTTAA TATTGAGTAT TTTGGTGGTG AATTTGGATT AAAATTTATA
         730        740        750        760        770        780
     TTTTAA.... .......... .......... .......... .......... ..........
```

FIG. 32A

```
         10         20         30         40         50         60
PVVSHYSDFS IKETYTNTEA LFGLKQDISS ILRNKETTQY NNNFNVPYTA KFQDDFASFS
         70         80         90        100        110        120
IAVGYIANNG PRIEIEGSYE EFDVKNPGNY TTIDAHRYIA LAREKTSYYL SSPKENKYVI
        130        140        150        160        170        180
IKNNGISIVS IIINGCYDIS LNDSKVSPYI CTGFGGDFIE FFSAIRFKFA YQGKIGISYS
        190        200        210        220        230        240
LSSNIILFTD GYYHKVINSQ FKNLNVEHVV NELTTDPKVT SATAFLNIEY FGGEFGLKFI
        250        260        270        280        290        300
F.......... .......... .......... .......... .......... ..........
```

```
         10         20         30         40         50         60
ATGAATCACA AAAGTATGCT CTTTACAATA GGTACAGCTT TGATATCCTT ATTGTCATTA
         70         80         90        100        110        120
CCTAATGTAT CATTCTCAGG AATCATAAAT AACAATGCTA ACAATTTAGG TATATACATT
        130        140        150        160        170        180
AGTGGGCAAT ATAAACCCAG TGTTTCTGTT TTTAGCAATT TCTCAGTAAA AGAAACTAAC
        190        200        210        220        230        240
TTCACTACAC AACAGTTAGT AGCACTTAAA AAAGATATTG ATTCTGTTGA CATTAGTACC
        250        260        270        280        290        300
AATGCTGATA GCGGTATTAA TAATCCGCAG AATTTCACTA TCCCTTATAT ACCAAAATTT
        310        320        330        340        350        360
CAAGACAATG CTGCTAGTTT TAGTGGAGCA CTTGGATTCT TCTACGCTAG AGGTTTAAGA
        370        380        390        400        410        420
CTTGAAATGG AAGGTTCCTA TGAAGAATTT GATGTTAAAA ACCCTGGAGG ATATACAAAA
        430        440        450        460        470        480
GTAAAAGATG CATATCGTTA CTTTGCCCTG GCACGTGAGA TGCAATCTGG TCAAACTTGC
        490        500        510        520        530        540
CCTAAACACA AAGAAACATC AGGTATTCAA CCTCACGGTA TTTATCACAC TGTTATGAGG
        550        560        570        580        590        600
AATGATGGGG TATCTATTTC ATCTGTCATA ATCAATGGTT GTTATAACTT TACTTTAAGT
        610        620        630        640        650        660
AATCTACCAA TATCACCTTA CATGTGTGTA GGTATGGGAA TAGATGCTAT ACAATTTTTT
        670        680        690        700        710        720
GATTCACTAC ATATTAAGTT TGCACATCAA AGTAAGTTAG GTATTACTTA CCCACTATCT
        730        740        750        760        770        780
TCAAATGTTC ATTTATTTGC TGATAGCTAT TATCATAAAG TAATAGGTAA TAAATTTAAA
        790        800        810        820        830        840
AATCTAAGGG TTCAACACGT TTATGAATTA CAACAGGTAC CTAAAGTTAC ATCTGCTGTT
        850        860        870        880        890        900
GCTACACTTG ATATTGGGTA TTTTGGTGGT GAAGTTGGAG TAAGGTTTAT ACTTTAA...
```

FIG. 33A

```
          10         20         30         40         50         60
   MNHKSMLFTI GTALISLLSL PNVSFSGIIN NNANNLGIYI SGQYKPSVSV FSNFSVKETN
          70         80         90        100        110        120
   FTTQQLVALK KDIDSVDIST NADSGINNPQ NFTIPYIPKF QDNAASFSGA LGFFYARGLR
         130        140        150        160        170        180
   LEMEGSYEEF DVKNPGGYTK VKDAYRYFAL AREMQSGQTC PKHKETSGIQ PHGIYHTVMR
         190        200        210        220        230        240
   NDGVSISSVI INGCYNFTLS NLPISPYMCV GMGIDAIQFF DSLHIKFAHQ SKLGITYPLS
         250        260        270        280        290        300
   SNVHLFADSY YHKVIGNKFK NLRVQHVYEL QQVPKVTSAV ATLDIGYFGG EVGVRFIL..
```

FIG. 33B

```
                                        SV
                                    ▼ ━━━━━━━
OMP-1F   MNCKKFFITT  TLVSLMSFLP  GISFSDAVQN  DNVG-GN---  -FYISGKYVP
OMP-1E   ..........  A.........  ......P..G  ..IS-..---  -..V....M.
OMP-1D   ...E......  A.TL......  ...L..P..D  ..IS-..---  -.......M.
OMP-1C   ..........  A.ALP.....  ..LL.EP..D  .S.S-..---  -.......M.
OMP-1B   ..Y..I.VSS  A.I....I..  YQ..A.P.TS  NDT.INDSRE  G....V..N.
P28      ----------  ----------  ------PA-G  SGIN-..---  -.......M.
MAP-1    .....I...S  T.I..V....  .V....VI.E  E.NPV.S---  -V...A..M.

HV1
                                                         ━━━━━━━━━━
OMP-1F   SVSHFGVFSA  KQ-----ERN  TTTGVFGLKQ  DWDGSTISKN  SPENTFNVPN
OMP-1E   .A....M...  .E-----.K.  P.VALY....  ..E.-IS.SS  HND.H..NKG
OMP-1D   .A........  .E-----...  ..V....IE.  ...RCV..RT  TLSDI.T...
OMP-1C   .A........  .E-----.K.  P.VALY....  ..N.-VSASS  HADAD..NKG
OMP-1B   .I...RK...  EEAPINGNTS  I.KK.....K  .------GDI  AQSAN..RTD
P28      .A........  .E-----...  ..V.......  N....A..NS  ..NDV.T.S.
MAP-1    TA....KM.I  .E-----DSR  D.KA.....K  ....VKTPSG  NTNSI.TEKD

OMP-1F   YSFKYENNPF  LGFAGAVGYL  MNGPRIELEM  SYETFDVKNQ  GNNYKNDAH-
OMP-1E   ..........  ......I..S  .G...V.F.V  ..........  .........-
OMP-1D   ........L.  S.....I..S  .D.......V  ...A......  ........E.-
OMP-1C   ..........  ......I..S  .G....F.V  ..........  .G.......-
OMP-1B   PALEFQ..LI  S..S.SI..A  .D.......A  AYQK..A..P  D..DT.SGDY
P28      ..........  ......I..S  .D.......V  ..........  ........E.-
MAP-1    ..........  .........S  ......F.V  ......R.P  .G.......-

HV2
         ━━━━━━━━━━
OMP-1F   -KYYALTH--  NSGGKLSNAG  DKFVFLKNEG  LLDISLMLNA  CYDVISEGIP
OMP-1E   -R.C..CQ--  -QDNSGIPKT  S.Y.L..S..  .....F....  ...I.N.S..
OMP-1D   -R....S.LL  GTETQIDG..  SAS...I...  ...K.F....  ..........
OMP-1C   -R.C..DR--  -KASSTNATA  SHY.L.....  ..........  .......V..
OMP-1B   Y..FG.SR--  ----EDAI.D  K.Y.V.....  ITFM...V.T  ...ITA..V.
P28      -R.C..SH--  ..AADM.S.S  NN........  .....F....  ....VG....
MAP-1    -M.C.----L  DTASSSTAGA  TTS.MV...N  .T........  ...IMLD.M.
```

*FIG. 34A*

```
OMP-1F  FSPYICAGVG  TDLISMFEAI  NPKISYQGKL  GLSYSISPEA  SVFVGGHFHK
OMP-1E  L.........  ........T.  ..........  ......N...  ...I......
OMP-1D  ........I.  I..V......  ..........  ....P.....  ...I......
OMP-1C  ..........  ..........  ..........  ......N...  ..........
OMP-1B  .I..A.....  A...NV.KDF  .L.F.....I  .I..P.T..V  .A.I..YY.G
P28     ........I.  ...V.M...T  ..........  ..........  ...I......
MAP-1   V...V...I.  ...V.VIN.T  ...L......  .I....N...  .I.I.....R
```

HV3

```
OMP-1F  VIGNEFRDIP  AMIPSTSTLT  GN-HF----T  IVTLSVCHFG  VELGGRFNF
OMP-1E  ..........  TLKAFVTSS-  -ATPDL---A  ..........  I........
OMP-1D  ..........  T....E.A.A  .KGNYP---A  ....D.FY..  I......QL
OMP-1C  .A.......S  TLKAFATPSS  AATPDL---A  T.........  .........
OMP-1B  ....N.NK..  VIT.VVLEGA  PQTTS----A  L..IDTGY..  G.V.V..T.
P28     ..........  TI..TG...A  .KGNYP---A  ..I.D.....  I......A.
MAP-1   ......K..A  TSKVF..SGN  ASSAVSPGFA  SAI.D.....  I.I....V.
```

*FIG. 34B*

SEQUENCE LISTING

<160> NUMBER OF SEQ ID NOS: 69

<210> SEQ ID NO 1
<211> LENGTH: 846
<212> TYPE: DNA
<213> ORGANISM: Ehrlichia chaffeensis

<400> SEQUENCE: 1

```
atgaattaca aaaagtttt cataacaagt gcattgatat cattaatatc ttctctacct      60
ggagtatcat tttccgaccc agcaggtagt ggtattaacg gtaatttcta catcagtgga    120
aaatacatgc caagtgcttc gcattttgga gtattctctg ctaaggaaga aagaaataca    180
acagttggag tgtttggact gaagcaaaat tgggacggaa gcgcaatatc caactcctcc    240
ccaaacgatg tattcactgt ctcaaattat tcatttaaat atgaaaacaa cccgttttta    300
ggttttgcag gagctattgg ttactcaatg gatggtccaa gaatagagct tgaagtatct    360
tatgaaacat ttgatgtaaa aaatcaaggt aacaattata agaatgaagc acatagatat    420
tgtgctctat cccataactc agcagcagac atgagtagtg caagtaataa ttttgtcttt    480
ctaaaaaatg aaggattact tgacatatca tttatgctga acgcatgcta tgacgtagta    540
ggcgaaggca taccttttc tccttatata tgcgcaggta tcggtactga tttagtatcc    600
atgtttgaag ctacaaatcc taaaatttct taccaaggaa agttaggttt aagctactct    660
ataagcccag aagcttctgt gtttattggt gggcactttc ataaggtaat agggaacgaa    720
tttagagata ttcctactat aatacctact ggatcaacac ttgcaggaaa aggaaactac    780
cctgcaatag taatactgga tgtatgccac tttggaatag aacttggagg aaggtttgct    840
ttctaa                                                               846
```

<210> SEQ ID NO 2
<211> LENGTH: 281
<212> TYPE: PRT
<213> ORGANISM: Ehrlichia chaffeensis

<400> SEQUENCE: 2

```
Met Asn Tyr Lys Lys Val Phe Ile Thr Ser Ala Leu Ile Ser Leu Ile
  1               5                  10                  15

Ser Ser Leu Pro Gly Val Ser Phe Ser Asp Pro Ala Gly Ser Gly Ile
              20                  25                  30

Asn Gly Asn Phe Tyr Ile Ser Gly Lys Tyr Met Pro Ser Ala Ser His
          35                  40                  45
```

```
Phe Gly Val Phe Ser Ala Lys Glu Glu Arg Asn Thr Thr Val Gly Val
        50                  55                  60
Phe Gly Leu Lys Gln Asn Trp Asp Gly Ser Ala Ile Ser Asn Ser Ser
 65                  70                  75                  80
Pro Asn Asp Val Phe Thr Val Ser Asn Tyr Ser Phe Lys Tyr Glu Asn
                85                  90                  95
Asn Pro Phe Leu Gly Phe Ala Gly Ala Ile Gly Tyr Ser Met Asp Gly
            100                 105                 110
Pro Arg Ile Glu Leu Glu Val Ser Tyr Glu Thr Phe Asp Val Lys Asn
        115                 120                 125
Gln Gly Asn Asn Tyr Lys Asn Glu Ala His Arg Tyr Cys Ala Leu Ser
    130                 135                 140
His Asn Ser Ala Ala Asp Met Ser Ser Ala Ser Asn Asn Phe Val Phe
145                 150                 155                 160
Leu Lys Asn Glu Gly Leu Leu Asp Ile Ser Phe Met Leu Asn Ala Cys
                165                 170                 175
Tyr Asp Val Val Gly Glu Gly Ile Pro Phe Ser Pro Tyr Ile Cys Ala
            180                 185                 190
Gly Ile Gly Thr Asp Leu Val Ser Met Phe Glu Ala Thr Asn Pro Lys
        195                 200                 205
Ile Ser Tyr Gln Gly Lys Leu Gly Leu Ser Tyr Ser Ile Ser Pro Glu
    210                 215                 220
Ala Ser Val Phe Ile Gly Gly His Phe His Lys Val Leu Gly Asn Glu
225                 230                 235                 240
Phe Arg Asp Ile Pro Thr Ile Ile Pro Thr Gly Ser Thr Leu Ala Gly
                245                 250                 255
Lys Gly Asn Tyr Pro Ala Ile Val Ile Leu Asp Val Cys His Phe Gly
            260                 265                 270
Ile Glu Leu Gly Gly Arg Phe Ala Phe
        275                 280

<210> SEQ ID NO 3
<211> LENGTH: 852
<212> TYPE: DNA
<213> ORGANISM: Ehrlichia chaffeensis

<400> SEQUENCE: 3
atgaattaca agaaaatttt tgtaagcagt gcattaattt cattaatgtc aatcttacct      60
taccaatctt ttgcagatcc tgtaacttca atgatacag gaatcaacga cagcagagaa     120
ggcttctaca ttagtgtaaa gtataatcca agcatatcac acttcagaaa attctcagct    180
gaagaagctc ccatcaatgg aaatacttct atcactaaaa aggttttcgg gctgaaaaaa    240
gacggagata tagcacaatc tgcgaatttt aacaggacag atccagccct cgagtttcag    300
aataacctaa tatcaggatt ctcaggaagt attggttatg ctatggatgg gccaagaata    360
gaacttgaag ctgcatacca aaaatttgat gcaaaaaatc ctgacaacaa tgacactaat    420
agcggtgact actataaata ctttggacta tctcgtgaag acgcaatagc agataagaaa    480
tatgttgtcc ttaaaaatga aggcatcact tttatgtcat taatggttaa cacttgctat    540
gacattacag ctgaaggagt accttcata ccgtatgcat gtgcaggtgt aggagcagac    600
cttataaacg tatttaagga ttttaattta aaattctcat accaagggaa ataggtatt    660
agctatccaa tcacaccaga gtttccgct tttattggag atactacca cggagttata    720
ggaaataatt ttaacaaaat acctgtaata acacctgtag tattagaagg agctcctcaa    780
```

```
acaacatctg cgctagtaac tattgacact ggatactttg gcggagaagt tggagtaagg    840
ttcaccttct ag                                                        852

<210> SEQ ID NO 4
<211> LENGTH: 283
<212> TYPE: PRT
<213> ORGANISM: Ehrlichia chaffeensis

<400> SEQUENCE: 4

Met Asn Tyr Lys Lys Ile Phe Val Ser Ser Ala Leu Ile Ser Leu Met
  1               5                  10                  15

Ser Ile Leu Pro Tyr Gln Ser Phe Ala Asp Pro Val Thr Ser Asn Asp
             20                  25                  30

Thr Gly Ile Asn Asp Ser Arg Glu Gly Phe Tyr Ile Ser Val Lys Tyr
         35                  40                  45

Asn Pro Ser Ile Ser His Phe Arg Lys Phe Ser Ala Glu Glu Ala Pro
     50                  55                  60

Ile Asn Gly Asn Thr Ser Ile Thr Lys Lys Val Phe Gly Leu Lys Lys
 65                  70                  75                  80

Asp Gly Asp Ile Ala Gln Ser Ala Asn Phe Asn Arg Thr Asp Pro Ala
                 85                  90                  95

Leu Glu Phe Gln Asn Asn Leu Ile Ser Gly Ser Gly Ser Ile Gly
            100                 105                 110

Tyr Ala Met Asp Gly Pro Arg Ile Glu Leu Glu Ala Ala Tyr Gln Lys
            115                 120                 125

Phe Asp Ala Lys Asn Pro Asp Asn Asn Asp Thr Asn Ser Gly Asp Tyr
        130                 135                 140

Tyr Lys Tyr Phe Gly Leu Ser Arg Glu Asp Ala Ile Ala Asp Lys Lys
145                 150                 155                 160

Tyr Val Val Leu Lys Asn Glu Gly Ile Thr Phe Met Ser Leu Met Val
                165                 170                 175

Asn Thr Cys Tyr Asp Ile Thr Ala Glu Gly Val Pro Phe Ile Pro Tyr
            180                 185                 190

Ala Cys Ala Gly Val Gly Ala Asp Leu Ile Asn Val Phe Lys Asp Phe
        195                 200                 205

Asn Leu Lys Phe Ser Tyr Gln Gly Lys Ile Gly Ile Ser Tyr Pro Ile
    210                 215                 220

Thr Pro Glu Val Ser Ala Phe Ile Gly Gly Tyr Tyr His Gly Val Ile
225                 230                 235                 240

Gly Asn Asn Phe Asn Lys Ile Pro Val Ile Thr Pro Val Leu Glu
                245                 250                 255

Gly Ala Pro Gln Thr Thr Ser Ala Leu Val Thr Ile Asp Thr Gly Tyr
            260                 265                 270

Phe Gly Gly Glu Val Gly Val Arg Phe Thr Phe
        275                 280

<210> SEQ ID NO 5
<211> LENGTH: 843
<212> TYPE: DNA
<213> ORGANISM: Ehrlichia chaffeensis

<400> SEQUENCE: 5
atgaactgca aaaatttttt tataacaact gcattggcat tgccaatgtc tttcttacct    60
ggaatattac tttctgaacc agtacaagat gacagtgtga gtggcaattt ctatattagt   120
```

-continued

```
ggcaagtaca tgccaagtgc ttctcatttt ggagttttct ctgccaaaga agaaaaaaat    180
cctactgtcg cgttgtatgg tttgaaacaa gattggaacg tgttagtgc ttcaagtcat     240 gctgatgcgg actttaataa caaaggttat tcttttaaat acgaaaacaa tccatttcta    300
ggttttgcag gagctattgg ttattcaatg ggtggtccaa gaatagagtt tgaagtgtcc    360
tatgaaacat ttgacgtgaa aaatcaaggt ggtaattaca aaatgatgc tcacagatac     420 tgtgccttag atcgtaaagc aagcagcact aatgccacag ctagtcacta cgtgctacta    480
aaaaatgaag gactacttga tatatcactt atgttgaatg catgctatga cgtagtaagt    540
gaaggaatac ctttctctcc ttacatatgt gcaggtgttg gtaccgattt aatatccatg    600
tttgaagcta taaaccctaa aatttcttat caaggaaagt taggtttgag ttactctata    660
aacccagaag cttctgtctt tgttggtgga cattttcata agttgcagg taatgaattc     720 agggacattt ctactcttaa agcgtttgct acaccatcat ctgcagctac tccagactta    780
gcaacagtaa cactgagtgt gtgtcacttt ggagtagaac ttggaggaag atttaacttc    840
taa                                                                  843

<210> SEQ ID NO 6
<211> LENGTH: 280
<212> TYPE: PRT
<213> ORGANISM: Ehrlichia chaffeensis

<400> SEQUENCE: 6

-continued

```
Arg Asp Ile Ser Thr Leu Lys Ala Phe Ala Thr Pro Ser Ser Ala Ala
                245                 250                 255

Thr Pro Asp Leu Ala Thr Val Thr Leu Ser Val Cys His Phe Gly Val
            260                 265                 270

Glu Leu Gly Gly Arg Phe Asn Phe
        275                 280
```

<210> SEQ ID NO 7
<211> LENGTH: 861
<212> TYPE: DNA
<213> ORGANISM: Ehrlichia chaffeensis

<400> SEQUENCE: 7

```
atgaactgcg aaaaattttt tataacaact gcattaacat tactaatgtc cttcttacct      60
ggaatatcac tttctgatcc agtacaggat gacaacatta gtggtaattt ctacatcagt     120
ggaaagtata tgccaagcgc ttcgcatttt ggagtttttt ctgccaagga agaaagaaat     180
acaacagttg gagtatttgg aatagagcaa gattgggata gatgtgtaat atctagaacc     240
actttaagcg atatattcac cgttccaaat tattcattta agtatgaaaa taatctattt     300
tcaggatttg caggagctat tggctactca atggatggcc caagaataga gcttgaagta     360
tcttatgaag cattcgatgt taaaaatcaa ggtaacaatt ataagaacga agcacataga     420
tattatgctc tgtcccatct tctcggcaca gagacacaga tagatggtgc aggcagtgcg     480
tctgtctttc taataaatga aggactactt gataaatcat ttatgctgaa cgcatgttat     540
gatgtaataa gtgaaggcat accttttttct ccttatatat gtgcaggtat tggtattgat     600
ttagtatcca tgtttgaagc tataaatcct aaaatttctt atcaaggaaa attaggctta     660
agttacccta taagcccaga agcttctgtg tttattggtg gacattttca taaggtgata     720
ggaaacgaat ttagagatat tcctactatg atacctagtg aatcagcgct tgcaggaaaa     780
ggaaactacc ctgcaatagt aacactggac gtgttctact ttggcataga acttggagga     840
aggtttaact tccaactttg a                                               861
```

<210> SEQ ID NO 8
<211> LENGTH: 286
<212> TYPE: PRT
<213> ORGANISM: Ehrlichia chaffeensis

<400> SEQUENCE: 8

```
Met Asn Cys Glu Lys Phe Phe Ile Thr Thr Ala Leu Thr Leu Leu Met
  1               5                  10                  15

Ser Phe Leu Pro Gly Ile Ser Leu Ser Asp Pro Val Gln Asp Asp Asn
             20                  25                  30

Ile Ser Gly Asn Phe Tyr Ile Ser Gly Lys Tyr Met Pro Ser Ala Ser
         35                  40                  45

His Phe Gly Val Phe Ser Ala Lys Glu Glu Arg Asn Thr Thr Val Gly
     50                  55                  60

Val Phe Gly Ile Glu Gln Asp Trp Asp Arg Cys Val Ile Ser Arg Thr
 65                  70                  75                  80

Thr Leu Ser Asp Ile Phe Thr Val Pro Asn Tyr Ser Phe Lys Tyr Glu
                 85                  90                  95

Asn Asn Leu Phe Ser Gly Phe Ala Gly Ala Ile Gly Tyr Ser Met Asp
            100                 105                 110

Gly Pro Arg Ile Glu Leu Glu Val Ser Tyr Glu Ala Phe Asp Val Lys
        115                 120                 125
```

-continued

```
Asn Gln Gly Asn Asn Tyr Lys Asn Glu Ala His Arg Tyr Tyr Ala Leu
    130                 135                 140

Ser His Leu Leu Gly Thr Glu Thr Gln Ile Asp Gly Ala Gly Ser Ala
145                 150                 155                 160

Ser Val Phe Leu Ile Asn Glu Gly Leu Leu Asp Lys Ser Phe Met Leu
                165                 170                 175

Asn Ala Cys Tyr Asp Val Ile Ser Glu Gly Ile Pro Phe Ser Pro Tyr
            180                 185                 190

Ile Cys Ala Gly Ile Gly Ile Asp Leu Val Ser Met Phe Glu Ala Ile
        195                 200                 205

Asn Pro Lys Ile Ser Tyr Gln Gly Lys Leu Gly Leu Ser Tyr Pro Ile
    210                 215                 220

Ser Pro Glu Ala Ser Val Phe Ile Gly Gly His Phe His Lys Val Ile
225                 230                 235                 240

Gly Asn Glu Phe Arg Asp Ile Pro Thr Met Ile Pro Ser Glu Ser Ala
                245                 250                 255

Leu Ala Gly Lys Gly Asn Tyr Pro Ala Ile Val Thr Leu Asp Val Phe
            260                 265                 270

Tyr Phe Gly Ile Glu Leu Gly Gly Arg Phe Asn Phe Gln Leu
        275                 280                 285

<210> SEQ ID NO 9
<211> LENGTH: 837
<212> TYPE: DNA
<213> ORGANISM: Ehrlichia chaffeensis

<400> SEQUENCE: 9
atgaattgca aaaaattttt tataacaact gcattagtat cactaatgtc ctttctacct      60
ggaatatcat tttctgatcc agtgcaaggt gacaatatta gtggtaattt ctatgttagt     120
ggcaagtata tgccaagtgc ttcgcatttt ggcatgtttt ctgccaaaga agaaaaaaat     180
cctactgttg cattgtatgg cttaaaacaa gattgggaag ggattagctc atcaagtcac     240
aatgataatc atttcaataa caagggttat tcatttaaat atgaaaataa cccattttta     300
gggtttgcag gagctattgg ttattcaatg ggtggtccaa gagtagagtt tgaagtgtcc     360
tatgaaacat ttgacgttaa aaatcagggt aataactata aaaatgatgc tcacagatac     420
tgtgctttag gtcaacaaga caacagcgga atacctaaaa ctagtaaata cgtactgtta     480
aaaagcgaag gattgcttga catatcattt atgctaaatg catgctatga tataataaac     540
gagagcatac ctttgtctcc ttacatatgt gcaggtgttg gtactgattt aatatccatg     600
tttgaagcta caaatcctaa aatttcttac caagggaagt taggtctaag ttactctata     660
aacccagaag cttctgtatt tattggtgga cattttcata aggtgatagg aaacgaattt     720
agggacattc ctactctgaa agcatttgtt acgtcatcag ctactccaga tctagcaata     780
gtaacactaa gtgtatgtca ttttggaata gaacttggag gaaggtttaa cttctaa       837

<210> SEQ ID NO 10
<211> LENGTH: 278
<212> TYPE: PRT
<213> ORGANISM: Ehrlichia chaffeensis

<400> SEQUENCE: 10

Met Asn Cys Lys Lys Phe Phe Ile Thr Thr Ala Leu Val Ser Leu Met
  1               5                  10                  15

Ser Phe Leu Pro Gly Ile Ser Phe Ser Asp Pro Val Gln Gly Asp Asn
             20                  25                  30
```

```
Ile Ser Gly Asn Phe Tyr Val Ser Gly Lys Tyr Met Pro Ser Ala Ser
         35                  40                  45

His Phe Gly Met Phe Ser Ala Lys Glu Glu Lys Asn Pro Thr Val Ala
     50                  55                  60

Leu Tyr Gly Leu Lys Gln Asp Trp Glu Gly Ile Ser Ser Ser Ser His
 65                  70                  75                  80

Asn Asp Asn His Phe Asn Asn Lys Gly Tyr Ser Phe Lys Tyr Glu Asn
                 85                  90                  95

Asn Pro Phe Leu Gly Phe Ala Gly Ile Gly Tyr Ser Met Gly Gly
             100                 105                 110

Pro Arg Val Glu Phe Glu Val Ser Tyr Glu Thr Phe Asp Val Lys Asn
             115                 120                 125

Gln Gly Asn Asn Tyr Lys Asn Asp Ala His Arg Tyr Cys Ala Leu Gly
        130                 135                 140

Gln Gln Asp Asn Ser Gly Ile Pro Lys Thr Ser Lys Tyr Val Leu Leu
145                 150                 155                 160

Lys Ser Glu Gly Leu Leu Asp Ile Ser Phe Met Leu Asn Ala Cys Tyr
                165                 170                 175

Asp Ile Ile Asn Glu Ser Ile Pro Leu Ser Pro Tyr Ile Cys Ala Gly
                180                 185                 190

Val Gly Thr Asp Leu Ile Ser Met Phe Glu Ala Thr Asn Pro Lys Ile
        195                 200                 205

Ser Tyr Gln Gly Lys Leu Gly Leu Ser Tyr Ser Ile Asn Pro Glu Ala
        210                 215                 220

Ser Val Phe Ile Gly Gly His Phe His Lys Val Ile Gly Asn Glu Phe
225                 230                 235                 240

Arg Asp Ile Pro Thr Leu Lys Ala Phe Val Thr Ser Ser Ala Thr Pro
                245                 250                 255

Asp Leu Ala Ile Val Thr Leu Ser Val Cys His Phe Gly Ile Glu Leu
            260                 265                 270

Gly Gly Arg Phe Asn Phe
        275

<210> SEQ ID NO 11
<211> LENGTH: 843
<212> TYPE: DNA
<213> ORGANISM: Ehrlichia chaffeensis

<400> SEQUENCE: 11
atgaattgca aaaatttttt tataacaact acattag

```
tccataagcc cagaagcttc tgttttttgtt ggtggacatt ttcataaggt gatagggaat      720
gaattcagag atattcctgc tatgataccc agtacctcaa ctctcacagg taatcacttt      780
actatagtaa cactaagtgt atgccacttt ggagtggaac ttggaggaag gtttaacttt      840
taa                                                                    843
```

<210> SEQ ID NO 12
<211> LENGTH: 280
<212> TYPE: PRT
<213> ORGANISM: Ehrlichia chaffeensis

<400> SEQUENCE: 12

```
Met Asn Cys Lys Lys Phe Phe Ile Thr Thr Thr Leu Val Ser Leu Met
 1               5                  10                  15

Ser Phe Leu Pro Gly Ile Ser Phe Ser Asp Ala Val Gln Asn Asp Asn
            20                  25                  30

Val Gly Gly Asn Phe Tyr Ile Ser Gly Lys Tyr Val Pro Ser Val Ser
        35                  40                  45

His Phe Gly Val Phe Ser Ala Lys Gln Glu Arg Asn Thr Thr Thr Gly
    50                  55                  60

Val Phe Gly Leu Lys Gln Asp Trp Asp Gly Ser Thr Ile Ser Lys Asn
65                  70                  75                  80

Ser Pro Glu Asn Thr Phe Asn Val Pro Asn Tyr Ser Phe Lys Tyr Glu
                85                  90                  95

Asn Asn Pro Phe Leu Gly Phe Ala Gly Ala Val Gly Tyr Leu Met Asn
            100                 105                 110

Gly Pro Arg Ile Glu Leu Glu Met Ser Tyr Glu Thr Phe Asp Val Lys
        115                 120                 125

Asn Gln Gly Asn Asn Tyr Lys Asn Asp Ala His Lys Tyr Tyr Ala Leu
    130                 135                 140

Thr His Asn Ser Gly Gly Lys Leu Ser Asn Ala Gly Asp Lys Phe Val
145                 150                 155                 160

Phe Leu Lys Asn Glu Gly Leu Leu Asp Ile Ser Leu Met Leu Asn Ala
                165                 170                 175

Cys Tyr Asp Val Ile Ser Glu Gly Ile Pro Phe Ser Pro Tyr Ile Cys
            180                 185                 190

Ala Gly Val Gly Thr Asp Leu Ile Ser Met Phe Glu Ala Ile Asn Pro
        195                 200                 205

Lys Ile Ser Tyr Gln Gly Lys Leu Gly Leu Ser Tyr Ser Ile Ser Pro
    210                 215                 220

Glu Ala Ser Val Phe Val Gly His Phe His Lys Val Ile Gly Asn
225                 230                 235                 240

Glu Phe Arg Asp Ile Pro Ala Met Ile Pro Ser Thr Ser Thr Leu Thr
                245                 250                 255

Gly Asn His Phe Thr Ile Val Thr Leu Ser Val Cys His Phe Gly Val
            260                 265                 270

Glu Leu Gly Gly Arg Phe Asn Phe
        275                 280
```

<210> SEQ ID NO 13
<211> LENGTH: 894
<212> TYPE: DNA
<213> ORGANISM: Ehrlichia chaffeensis

<400> SEQUENCE: 13

```
atggaaaatc tcatgaataa gaaaaacaaa ttctttacaa taagtacagc aatggtatgc      60
```

-continued

```
ttattgttat tacctggtat atcattttca gaaactataa acaacagtgc taaaaaacag    120
cctgggttat atatcagtgg gcagtacaaa cctagtgttt cagtttttag taatttttca    180
gtaaaagaaa ctaatgttcc cacaaagcag ttaatagcac ttaaaaaaga cattaattct    240
gttgcagttg gtagtaatgc tactacaggt attagcaatc caggtaattt cacaattcct    300
tatactgcag aatttcaaga taatgttgcc aatttcaatg gggctgttgg ttactctttt    360
cctgatagtc taagaattga aatagaggga tttcatgaaa aatttgatgt caaaaaccct    420
ggaggttaca cacaagtaaa agatgcgtac cgttatttg cactagcacg tgatttaaaa    480
gatggcttct ttgaacctaa agcggaagat acaggtgttt atcatactgt tatgaaaaat    540
gatggattat ctattttatc tactatggtt aacgtctgtt acgatttttc tgtagatgaa    600
ttaccagtct taccttatat atgtgcaggt atgggtataa acgccataga attcttcgac    660
gctttacatg taaaatttgc ttaccaaggc aaactaggta ttagctatca actatttact    720
aaagtaaatt tattccttga tgggtattac catcaagtaa taggcaatca attcaaaaac    780
ttaaacgtaa accatgttta cacacttaaa gaatctccta aagtcacatc tgcagtagct    840
acacttgaca ttgcatactt tggtggcgaa gttggaataa gattcacatt ttaa          894
```

<210> SEQ ID NO 14
<211> LENGTH: 297
<212> TYPE: PRT
<213> ORGANISM: Ehrlichia chaffeensis

<400> SEQUENCE: 14

```
Met Glu Asn Leu Met Asn Lys Lys Asn Lys Phe Phe Thr Ile Ser Thr
 1               5                   10                  15

Ala Met Val Cys Leu Leu Leu Pro Gly Ile Ser Phe Ser Glu Thr
            20                  25                  30

Ile Asn Asn Ser Ala Lys Lys Gln Pro Gly Leu Tyr Ile Ser Gly Gln
        35                  40                  45

Tyr Lys Pro Ser Val Ser Val Phe Ser Asn Phe Ser Val Lys Glu Thr
    50                  55                  60

Asn Val Pro Thr Lys Gln Leu Ile Ala Leu Lys Lys Asp Ile Asn Ser
65                  70                  75                  80

Val Ala Val Gly Ser Asn Ala Thr Thr Gly Ile Ser Asn Pro Gly Asn
                85                  90                  95

Phe Thr Ile Pro Tyr Thr Ala Glu Phe Gln Asp Asn Val Ala Asn Phe
            100                 105                 110

Asn Gly Ala Val Gly Tyr Ser Phe Pro Asp Ser Leu Arg Ile Glu Ile
        115                 120                 125

Glu Gly Phe His Glu Lys Phe Asp Val Lys Asn Pro Gly Gly Tyr Thr
    130                 135                 140

Gln Val Lys Asp Ala Tyr Arg Tyr Phe Ala Leu Ala Arg Asp Leu Lys
145                 150                 155                 160

Asp Gly Phe Phe Glu Pro Lys Ala Glu Asp Thr Gly Val Tyr His Thr
                165                 170                 175

Val Met Lys Asn Asp Gly Leu Ser Ile Leu Ser Thr Met Val Asn Val
            180                 185                 190

Cys Tyr Asp Phe Ser Val Asp Glu Leu Pro Val Leu Pro Tyr Ile Cys
        195                 200                 205

Ala Gly Met Gly Ile Asn Ala Ile Glu Phe Phe Asp Ala Leu His Val
    210                 215                 220
```

```
Lys Phe Ala Tyr Gln Gly Lys Leu Gly Ile Ser Tyr Gln Leu Phe Thr
225                 230                 235                 240

Lys Val Asn Leu Phe Leu Asp Gly Tyr Tyr His Gln Val Ile Gly Asn
            245                 250                 255

Gln Phe Lys Asn Leu Asn Val Asn His Val Tyr Thr Leu Lys Glu Ser
        260                 265                 270

Pro Lys Val Thr Ser Ala Val Ala Thr Leu Asp Ile Ala Tyr Phe Gly
    275                 280                 285

Gly Glu Val Gly Ile Arg Phe Thr Phe
290                 295
```

<210> SEQ ID NO 15
<211> LENGTH: 591
<212> TYPE: DNA
<213> ORGANISM: Ehrlichia chaffeensis

<400> SEQUENCE: 15

```
atgatatata aagaaaaact tactagagtg ggagaatata tcttagcata tttatcattt      60
attctttcta cttatatctt tctagtgctg gtaaatatta ttagatataa cagccttgct     120
atatgtgtta tcagtctact aagaactaat atctttaacg ttagcacaaa aaattaata     180
aaagataaat gtcgtgatac taagtttagt aacatgaatt gttatttgta cggtaaaccg     240
ttaaatttac aaattttta tggaatattt tcctttatta gaaactttca aaataacaca     300
ctaataattc ctaatgatag taaatgcggc ttctatacca cgttatggga taatccagca     360
ctacattata catatacact tactggcagt gagtaccgta attttttga cattctatat     420
gaaaacatta tctgtcaatg taaattactt attaactata accgttctgt attaaaccaa     480
cataataaaa atactctcgt aataatacca atacctaatg ctagagagtt cagtaatgaa     540
attcgagtaa ggaatatatc aataaataag gaaagttctt atgagtgcta a             591
```

<210> SEQ ID NO 16
<211> LENGTH: 196
<212> TYPE: PRT
<213> ORGANISM: Ehrlichia chaffeensis

<400> SEQUENCE: 16

```
Met Ile Tyr Lys Glu Lys Leu Thr Arg Val Gly Glu Tyr Ile Leu Ala
1               5                   10                  15

Tyr Leu Ser Phe Ile Leu Ser Thr Tyr Ile Phe Leu Val Leu Val Asn
            20                  25                  30

Ile Ile Arg Tyr Asn Ser Leu Ala Ile Cys Val Ile Ser Leu Leu Arg
        35                  40                  45

Thr Asn Ile Phe Asn Val Ser Thr Lys Lys Leu Ile Lys Asp Lys Cys
    50                  55                  60

Arg Asp Thr Lys Phe Ser Asn Met Asn Cys Tyr Leu Tyr Gly Lys Pro
65                  70                  75                  80

Leu Asn Leu Gln Ile Phe Tyr Gly Ile Phe Ser Phe Ile Arg Asn Phe
            85                  90                  95

Gln Asn Asn Thr Leu Ile Ile Pro Asn Asp Ser Lys Cys Gly Phe Tyr
        100                 105                 110

Thr Thr Leu Trp Asp Asn Pro Ala Leu His Tyr Thr Tyr Thr Leu Thr
    115                 120                 125

Gly Ser Glu Tyr Arg Asn Phe Phe Asp Ile Leu Tyr Glu Asn Ile Ile
130                 135                 140

Cys Gln Cys Lys Leu Leu Ile Asn Tyr Asn Arg Ser Val Leu Asn Gln
```

```
                145                 150                 155                 160
His Asn Lys Asn Thr Leu Val Ile Ile Pro Ile Pro Asn Ala Arg Glu
                    165                 170                 175

Phe Ser Asn Glu Ile Arg Val Arg Asn Ile Ser Ile Asn Lys Glu Ser
                180                 185                 190

Ser Tyr Glu Cys
        195

<210> SEQ ID NO 17
<211> LENGTH: 876
<212> TYPE: DNA
<213> ORGANISM: Ehrlichia chaffeensis

<400> SEQUENCE: 17
atgaataaaa aaaacaagtt tattatagct acagcattgg tatatttact gtcattacct      60
agtgtatcgt ttcagaggt  tacaaacagc agtattaaaa acactctgg  gttatatatt     120 agtggacaat acaaaccaag tgtttctgtt tttagtagtt ctcaattaa agaaactaac     180 actatcacaa aaaatcttat agcgttaaaa aaagatatta actctcttga agttaacgcc     240
gatgctagtc aaggtattag tcatccagga aattttacta taccttatat agcagcattt     300
gaagataatg cttttaattt caacggtgct attggttaca ttactgaagg tctaaggatt     360
gaaatagaag gttcctatga agaatttgat gctaaaaacc ctggaggtta tggtctaaat     420
gatgcctttc ggtactttgc tttagcacgt gatatggaaa gcaacaagtt ccaaccaaaa     480 gcacaaaagct cacaaaaagt atttcacact gtaatgaaga gtgatgggtt atctataata     540
tctatcatgg ttaacggctg ttatgatttt tcttcggata atttattagt atcaccttat     600
atatgtggag gtataggtgt ggatgcaata gaatttttg acgcattaca cattaaactt     660
gcgtgccaaa gcaaattagg catcacttat caattatctt ataatatcag cttatttgct     720
gatggatatt atcatcaagt aataggtaac caattcagaa atttaaacgt tcaacatgta     780
gctgaactta atgatgcacc taaagttaca tctgcagttg ccacacttaa tgttggatat     840
ttcggcgctg aagttggagt aagatttata ttttaa                               876

<210> SEQ ID NO 18
<211> LENGTH: 291
<212> TYPE: PRT
<213> ORGANISM: Ehrlichia chaffeensis

<400> SEQUENCE: 18

Met Asn Lys Lys Asn Lys Phe Ile Ile Ala Thr Ala Leu Val Tyr Leu
1               5                   10                  15

Leu Ser Leu Pro Ser Val Ser Phe Ser Glu Val Thr Asn Ser Ser Ile
                20                  25                  30

Lys Lys His Ser Gly Leu Tyr Ile Ser Gly Gln Tyr Lys Pro Ser Val
            35                  40                  45

Ser Val Phe Ser Ser Phe Ser Ile Lys Glu Thr Asn Thr Ile Thr Lys
        50                  55                  60

Asn Leu Ile Ala Leu Lys Lys Asp Ile Asn Ser Leu Glu Val Asn Ala
65                  70                  75                  80

Asp Ala Ser Gln Gly Ile Ser His Pro Gly Asn Phe Thr Ile Pro Tyr
                85                  90                  95

Ile Ala Ala Phe Glu Asp Asn Ala Phe Asn Phe Asn Gly Ala Ile Gly
            100                 105                 110

Tyr Ile Thr Glu Gly Leu Arg Ile Glu Ile Glu Gly Ser Tyr Glu Glu
```

-continued

```
        115                 120                 125

Phe Asp Ala Lys Asn Pro Gly Gly Tyr Gly Leu Asn Asp Ala Phe Arg
    130                 135                 140

Tyr Phe Ala Leu Ala Arg Asp Met Glu Ser Asn Lys Phe Gln Pro Lys
145                 150                 155                 160

Ala Gln Ser Ser Gln Lys Val Phe His Thr Val Met Lys Ser Asp Gly
                165                 170                 175

Leu Ser Ile Ile Ser Ile Met Val Asn Gly Cys Tyr Asp Phe Ser Ser
            180                 185                 190

Asp Asn Leu Leu Val Ser Pro Tyr Ile Cys Gly Gly Ile Gly Val Asp
        195                 200                 205

Ala Ile Glu Phe Phe Asp Ala Leu His Ile Lys Leu Ala Cys Gln Ser
    210                 215                 220

Lys Leu Gly Ile Thr Tyr Gln Leu Ser Tyr Asn Ile Ser Leu Phe Ala
225                 230                 235                 240

Asp Gly Tyr Tyr His Gln Val Ile Gly Asn Gln Phe Arg Asn Leu Asn
                245                 250                 255

Val Gln His Val Ala Glu Leu Asn Asp Ala Pro Lys Val Thr Ser Ala
            260                 265                 270

Val Ala Thr Leu Asn Val Gly Tyr Phe Gly Ala Glu Val Gly Val Arg
        275                 280                 285

Phe Ile Phe
    290

<210> SEQ ID NO 19
<211> LENGTH: 396
<212> TYPE: DNA
<213> ORGANISM: Ehrlichia chaffeensis

<400> SEQUENCE: 19
tctagaatac atgatgaaaa ttatgctatt acaacaaata ataaattatc catcgcatct      60
attatggtta acacctgcta tgatatttca attaataata catcaatagt accgtattta     120
tgcacaggca ttggtgaaga tcttgtaggg ctttttaata caatacattt taaacttgca     180
tatcaaggga aagttggaat gagttatttg ataaataaca atatcctatt attttctgac     240
atatattatc ataaagtcat gggtaacaga tttaaaaatt tgtacatgca atatgtagct     300
gatcctaata tttctgaaga aactatacct atattagcaa aacttgatat tggttatttt     360
ggaagtgaaa ttggaataag gtttatgttt aactaa                               396

<210> SEQ ID NO 20
<211> LENGTH: 131
<212> TYPE: PRT
<213> ORGANISM: Ehrlichia chaffeensis

<400> SEQUENCE: 20

Ser Arg Ile His Asp Glu Asn Tyr Ala Ile Thr Thr Asn Asn Lys Leu
  1               5                  10                  15

Ser Ile Ala Ser Ile Met Val Asn Thr Cys Tyr Asp Ile Ser Ile Asn
            20                  25                  30

Asn Thr Ser Ile Val Pro Tyr Leu Cys Thr Gly Ile Gly Glu Asp Leu
         35                  40                  45

Val Gly Leu Phe Asn Thr Ile His Phe Lys Leu Ala Tyr Gln Gly Lys
     50                  55                  60

Val Gly Met Ser Tyr Leu Ile Asn Asn Asn Ile Leu Leu Phe Ser Asp
 65                  70                  75                  80
```

-continued

```
Ile Tyr Tyr His Lys Val Met Gly Asn Arg Phe Lys Asn Leu Tyr Met
                85                  90                  95

Gln Tyr Val Ala Asp Pro Asn Ile Ser Glu Glu Thr Ile Pro Ile Leu
            100                 105                 110

Ala Lys Leu Asp Ile Gly Tyr Phe Gly Ser Glu Ile Gly Ile Arg Phe
        115                 120                 125

Met Phe Asn
    130

<210> SEQ ID NO 21
<211> LENGTH: 888
<212> TYPE: DNA
<213> ORGANISM: Ehrlichia chaffeensis

<400> SEQUENCE: 21
atgacaaaga aatttaattt tgtaaatgtt atattaacat ttttgttatt tcttttccca      60
cttaagtcat ttacaacata tgcaaataat aacacaatca ctcaaaaagt tggattgtac     120
ataagtggtc aatataagcc aagtattcct catttcaaga atttttcagt agaagaaaat     180
gacaaagtag tagatttgat aggtcttaca actgatgtta catatatcac agaacatata     240
ttacgagata atacaaaatt caacactcat tatattgcaa agttcaagaa caattttata     300
aatttcagca gtgcaattgg ttattattct gggcaaggac caaggttaga aatagaaagc     360
tcttatgggg attttgatgt tgtaaattat aaaaattatg cagtacaaga tgttaataga     420
tattttgctt tagtacgtga aaaaaatggt tcaaatttct ctccaaaacc acatgaaact     480
agtcaaccct ctgacagtaa tcctaaaaag tctttttata ctttaatgaa gaataatggg     540
gtatttgttg catcagtaat aatcaacggt tgttatgatt tttcttttaa taacacaaca     600
atatcacctt acgtatgtat aggagttgga ggagatttta tagagttttt tgaagtaatg     660
catatcaagt ttgcttgcca aagtaaggtt ggtattagct atccaatatc tccctctatt     720
actatttttg ctgatgcaca ttatcacaag gtcataaata ataaatttaa caacctacat     780
gttaagtatt catatgaact taaaaactca cctaccatta cctctgcaac agccaaacta     840
aacattgaat attttggtgg tgaagttggg atgagattta tattttaa                 888

<210> SEQ ID NO 22
<211> LENGTH: 295
<212> TYPE: PRT
<213> ORGANISM: Ehrlichia chaffeensis

<400> SEQUENCE: 22

Met Thr Lys Lys Phe Asn Phe Val Asn Val Ile Leu Thr Phe Leu Leu
  1               5                  10                  15

Phe Leu Phe Pro Leu Lys Ser Phe Thr Thr Tyr Ala Asn Asn Asn Thr
             20                  25                  30

Ile Thr Gln Lys Val Gly Leu Tyr Ile Ser Gly Gln Tyr Lys Pro Ser
         35                  40                  45

Ile Pro His Phe Lys Asn Phe Ser Val Glu Glu Asn Asp Lys Val Val
     50                  55                  60

Asp Leu Ile Gly Leu Thr Thr Asp Val Thr Tyr Ile Thr Glu His Ile
 65                  70                  75                  80

Leu Arg Asp Asn Thr Lys Phe Asn Thr His Tyr Ile Ala Lys Phe Lys
                 85                  90                  95

Asn Asn Phe Ile Asn Phe Ser Ser Ala Ile Gly Tyr Tyr Ser Gly Gln
            100                 105                 110
```

-continued

Gly Pro Arg Leu Glu Ile Glu Ser Ser Tyr Gly Asp Phe Asp Val Val
        115                 120                 125

Asn Tyr Lys Asn Tyr Ala Val Gln Asp Val Asn Arg Tyr Phe Ala Leu
    130                 135                 140

Val Arg Glu Lys Asn Gly Ser Asn Phe Ser Pro Lys Pro His Glu Thr
145                 150                 155                 160

Ser Gln Pro Ser Asp Ser Asn Pro Lys Lys Ser Phe Tyr Thr Leu Met
                165                 170                 175

Lys Asn Asn Gly Val Phe Val Ala Ser Val Ile Ile Asn Gly Cys Tyr
            180                 185                 190

Asp Phe Ser Phe Asn Asn Thr Thr Ile Ser Pro Tyr Val Cys Ile Gly
        195                 200                 205

Val Gly Gly Asp Phe Ile Glu Phe Phe Glu Val Met His Ile Lys Phe
    210                 215                 220

Ala Cys Gln Ser Lys Val Gly Ile Ser Tyr Pro Ile Ser Pro Ser Ile
225                 230                 235                 240

Thr Ile Phe Ala Asp Ala His Tyr His Lys Val Ile Asn Asn Lys Phe
                245                 250                 255

Asn Asn Leu His Val Lys Tyr Ser Tyr Glu Leu Lys Asn Ser Pro Thr
            260                 265                 270

Ile Thr Ser Ala Thr Ala Lys Leu Asn Ile Glu Tyr Phe Gly Gly Glu
        275                 280                 285

Val Gly Met Arg Phe Ile Phe
    290                 295

<210> SEQ ID NO 23
<211> LENGTH: 840
<212> TYPE: DNA
<213> ORGANISM: Ehrlichia chaffeensis

<400> SEQUENCE: 23
atgagcaaaa aaaagtttat tacaatagga acagtacttg catctctatt atcattctta      60
tctattgaat cctttcagc tataaatcat aatcatacag gaataacac tagtggtata      120
tatattacag ggcagtatag accaggagta tcccattta gcaatttctc agtaaaagaa      180
actaatgttg atacaataca actagtagga tataaaaaaa gtgcgtcttc tatcgatcct      240
aacacttatt caaactttca aggtccatat actgttacat tcaagataa tgctgctagt      300
ttcagtggag caattggata ttcttacccc gaaagtctaa gacttgaact tgaaggttct      360
tacgaaaaat tgatgtcaa agatcctaaa gactactcag caaagatgc ttttaggttt      420
tttgctctag cacgtaatac gtctactact gttcctgatg ctcaaaaata tacagttatg      480
aagaataatg gcttatctgt tgcatcaatc atgatcaatg gttgttatga tctatctttt      540
aataatttag tcgtatcacc ttatatatgt gcaggtattg gtgaagattt cattgaattt      600
tttgatactt tgcacattaa acttgcttat caaggaaaac taggtattag ttattacttc      660
tttcctaaga ttaatgtatt tgctggtggg tactatcata gagttatagg gaataaattt      720
aaaaattaa atgttaacca tgttgttaca cttgatgaat ttcctaaagc aacttctgca      780
gtagctacac ttaatgttgc ttattttggt ggtgaagctg gagtaaagtt tacatttaa      840

<210> SEQ ID NO 24
<211> LENGTH: 279
<212> TYPE: PRT
<213> ORGANISM: Ehrlichia chaffeensis -continued

<400> SEQUENCE: 24

Met Ser Lys Lys Lys Phe Ile Thr Ile Gly Thr Val Leu Ala Ser Leu
1 5 10 15

Leu Ser Phe Leu Ser Ile Glu Ser Phe Ser Ala Ile Asn His Asn His
20 25 30

Thr Gly Asn Asn Thr Ser Gly Ile Tyr Ile Thr Gly Gln Tyr Arg Pro
35 40 45

Gly Val Ser His Phe Ser Asn Phe Ser Val Lys Glu Thr Asn Val Asp
50 55 60

Thr Ile Gln Leu Val Gly Tyr Lys Lys Ser Ala Ser Ser Ile Asp Pro
65 70 75 80

Asn Thr Tyr Ser Asn Phe Gln Gly Pro Tyr Thr Val Thr Phe Gln Asp
85 90 95

Asn Ala Ala Ser Phe Ser Gly Ala Ile Gly Tyr Ser Tyr Pro Glu Ser
100 105 110

Leu Arg Leu Glu Leu Glu Gly Ser Tyr Glu Lys Phe Asp Val Lys Asp
115 120 125

Pro Lys Asp Tyr Ser Ala Lys Asp Ala Phe Arg Phe Phe Ala Leu Ala
130 135 140

Arg Asn Thr Ser Thr Thr Val Pro Asp Ala Gln Lys Tyr Thr Val Met
145 150 155 160

Lys Asn Asn Gly Leu Ser Val Ala Ser Ile Met Ile Asn Gly Cys Tyr
165 170 175

Asp Leu Ser Phe Asn Asn Leu Val Val Ser Pro Tyr Ile Cys Ala Gly
180 185 190

Ile Gly Glu Asp Phe Ile Glu Phe Phe Asp Thr Leu His Ile Lys Leu
195 200 205

Ala Tyr Gln Gly Lys Leu Gly Ile Ser Tyr Tyr Phe Phe Pro Lys Ile
210 215 220

Asn Val Phe Ala Gly Gly Tyr Tyr His Arg Val Ile Gly Asn Lys Phe
225 230 235 240

Lys Asn Leu Asn Val Asn His Val Val Thr Leu Asp Glu Phe Pro Lys
245 250 255

Ala Thr Ser Ala Val Ala Thr Leu Asn Val Ala Tyr Phe Gly Gly Glu
260 265 270

Ala Gly Val Lys Phe Thr Phe
275

<210> SEQ ID NO 25
<211> LENGTH: 852
<212> TYPE: DNA
<213> ORGANISM: Ehrlichia chaffeensis

<400> SEQUENCE: 25
atgagtgcta aaaaaaagct ttttataata gggtcagtgt tagtatgttt agtgtcatac 60
ttacctacta aatctttgtc aaacttaaat aatattaata ataacactaa gtgcactggg 120
ctatatgtca gtggacaata taaacctact gtttctcact ttagtaattt ttcacttaaa 180
gaaacttata ctgacactaa agagttatta ggactagcaa aagatattaa gtctattaca 240
gatataacaa caaataaaaa attcaacatt ccttataaca caaaatttca agataatgct 300
gttagcttca gtgcagctgt tggatatatt tcccaagaca gtccaagggt tgaggtagaa 360
tggtcttatg aagaatttga cgttaaaaat cctggtaatt acgtagtaag tgaagccttc 420
aggtatattg ctttagcaag aggaattgat aatcttcaaa aatatcctga aacaaataag 480

```
tatgttgtta taaagaacaa tggcttatct gtcgcatcca ttataatcaa tggctgttat    540 gattttctt taaacaattt aaaagtatca ccttacatat gcgtagggtt tggtggggac    600
attatagaat tttttagtgc tgtaagtttt aaatttgctt atcaaggtaa ggtaggtatc    660
agttatccat tattctctaa tatgattata tttgctgacg gatattacca taaggtcata    720
ggaaataaat ttaacaattt aaatgttcaa cacgttgtta gtcttaacag tcatcctaag    780 tctactttg cagtagctac tcttaatgtt gagtatttcg gtagtgaatt tgggttaaaa    840
tttatatttt aa                                                        852
```

```
<210> SEQ ID NO 26
<211> LENGTH: 283
<212> TYPE: PRT
<213> ORGANISM: Ehrlichia chaffeensis

<400> SEQUENCE: 26
```

Met Ser Ala Lys Lys Leu Phe Ile Ile Gly Ser Val Leu Val Cys
 1               5                  10                  15

Leu Val Ser Tyr Leu Pro Thr Lys Ser Leu Ser Asn Leu Asn Asn Ile
                20                  25                  30

Asn Asn Thr Lys Cys Thr Gly Leu Tyr Val Ser Gly Gln Tyr Lys
         35                  40                  45

Pro Thr Val Ser His Phe Ser Asn Phe Ser Leu Lys Glu Thr Tyr Thr
     50                  55                  60

Asp Thr Lys Glu Leu Leu Gly Leu Ala Lys Asp Ile Lys Ser Ile Thr
 65                  70                  75                  80

Asp Ile Thr Thr Asn Lys Lys Phe Asn Ile Pro Tyr Asn Thr Lys Phe
                 85                  90                  95

Gln Asp Asn Ala Val Ser Phe Ser Ala Ala Val Gly Tyr Ile Ser Gln
             100                 105                 110

Asp Ser Pro Arg Val Glu Val Glu Trp Ser Tyr Glu Gly Phe Asp Val
         115                 120                 125

Lys Asn Pro Gly Asn Tyr Val Val Ser Glu Ala Phe Arg Tyr Ile Ala
     130                 135                 140

Leu Ala Arg Gly Ile Asp Asn Leu Gln Lys Tyr Pro Glu Thr Asn Lys
145                 150                 155                 160

Tyr Val Val Ile Lys Asn Asn Gly Leu Ser Val Ala Ser Ile Ile Ile
                165                 170                 175

Asn Gly Cys Tyr Asp Phe Ser Leu Asn Asn Leu Lys Val Ser Pro Tyr
            180                 185                 190

Ile Cys Val Gly Phe Gly Gly Asp Ile Ile Glu Phe Ser Ala Val
        195                 200                 205

Ser Phe Lys Phe Ala Tyr Gln Gly Lys Val Gly Ile Ser Tyr Pro Leu
    210                 215                 220

Phe Ser Asn Met Ile Ile Phe Ala Asp Gly Tyr Tyr His Lys Val Ile
225                 230                 235                 240

Gly Asn Lys Phe Asn Asn Leu Asn Val Gln His Val Val Ser Leu Asn
                245                 250                 255

Ser His Pro Lys Ser Thr Phe Ala Val Ala Thr Leu Asn Val Glu Tyr
            260                 265                 270

Phe Gly Ser Glu Phe Gly Leu Lys Phe Ile Phe
        275                 280

```
<210> SEQ ID NO 27
```

-continued

<211> LENGTH: 828
<212> TYPE: DNA
<213> ORGANISM: Ehrlichia chaffeensis

<400> SEQUENCE: 27

```
atgagtaaaa aaaattttat tacaatagga gcaacactta ttcatatgtt gttacctaac     60
atatcttttc cagaaactat taacaataac actgataaac tttctgggtt atatataagt    120
gggcaatata aaccagggat ttctcatttc agcaaatttt cagtcaaaga aatctataat    180
gataacattc aactaattgg gttaagacac aacgcaattt ctactagtac ccttaatatt    240
aatacagatt ttaatatccc ctataaagta acatttcaaa ataacattac cagctttagt    300
ggagctattg gttattctga tcccacaggg gcaagatttg agcttgaagg ttcttatgaa    360
gaatttgatg tgacagatcc tggagactgc ttaataaaag atacctatag atatttcgct    420
ttagctagaa acccatcagg ttctagccct acctcaaaca actatactgt tatgagaaat    480
gatggtgttt ccattacttc tgttatattt aatggctgtt atgacatctt tttaaaggat    540
ttagaagtat caccttatgt atgtgttggt gtaggtggag attttataga atttttttgac    600 gcattacaca ttaaattagc ataccaaggc aagttaggta tcaattatca cttatcgact    660
caagcaagcg tatttattga tggatattat cataaggtta taggaaatca attcaacaat    720
ctaaatgttc aacacgtggc tagtacagat tttggacctg tatacgcagt agccacactt    780
aacattggtt attttggtgg tgaaatcgga attagactta cattttaa                828
```

<210> SEQ ID NO 28
<211> LENGTH: 275
<212> TYPE: PRT
<213> ORGANISM: Ehrlichia chaffeensis

<400> SEQUENCE: 28

```
Met Ser Lys Lys Asn Phe Ile Thr Ile Gly Ala Thr Leu Ile His Met
1               5                   10                  15

Leu Leu Pro Asn Ile Ser Phe Pro Glu Thr Ile Asn Asn Asn Thr Asp
            20                  25                  30

Lys Leu Ser Gly Leu Tyr Ile Ser Gly Gln Tyr Lys Pro Gly Ile Ser
        35                  40                  45

His Phe Ser Lys Phe Ser Val Lys Glu Ile Tyr Asn Asp Asn Ile Gln
    50                  55                  60

Leu Ile Gly Leu Arg His Asn Ala Ile Ser Thr Ser Thr Leu Asn Ile
65                  70                  75                  80

Asn Thr Asp Phe Asn Ile Pro Tyr Lys Val Thr Phe Gln Asn Asn Ile
                85                  90                  95

Thr Ser Phe Ser Gly Ala Ile Gly Tyr Ser Asp Pro Thr Gly Ala Arg
            100                 105                 110

Phe Glu Leu Glu Gly Ser Tyr Glu Glu Phe Asp Val Thr Asp Pro Gly
        115                 120                 125

Asp Cys Leu Ile Lys Asp Thr Tyr Arg Tyr Phe Ala Leu Ala Arg Asn
    130                 135                 140

Pro Ser Gly Ser Ser Pro Thr Ser Asn Asn Tyr Thr Val Met Arg Asn
145                 150                 155                 160

Asp Gly Val Ser Ile Thr Ser Val Ile Phe Asn Gly Cys Tyr Asp Ile
                165                 170                 175

Phe Leu Lys Asp Leu Glu Val Ser Pro Tyr Val Cys Val Gly Val Gly
            180                 185                 190

Gly Asp Phe Ile Glu Phe Phe Asp Ala Leu His Ile Lys Leu Ala Tyr
```

```
                195                 200                 205
Gln Gly Lys Leu Gly Ile Asn Tyr His Leu Ser Thr Gln Ala Ser Val
    210                 215                 220

Phe Ile Asp Gly Tyr Tyr His Lys Val Ile Gly Asn Gln Phe Asn Asn
225                 230                 235                 240

Leu Asn Val Gln His Val Ala Ser Thr Asp Phe Gly Pro Val Tyr Ala
                245                 250                 255

Val Ala Thr Leu Asn Ile Gly Tyr Phe Gly Gly Glu Ile Gly Ile Arg
                260                 265                 270

Leu Thr Phe
        275

<210> SEQ ID NO 29
<211> LENGTH: 858
<212> TYPE: DNA
<213> ORGANISM: Ehrlichia chaffeensis

<400> SEQUENCE: 29
atgaataata gaaaagtttt ttttataata ggtgcatcat tactagcaag cttattattc      60
acatctgagg cctcttctac aggaaatgta agtaaccata cttattttaa acctaggtta     120
tatatcagtg gacaatatag accaggagtt tctcatttta gcaaattttc agtcaaagaa     180
accaactaca atactactca actagttggg cttaaaaagg acatcagtgt catagggaac     240
agtaatatca caacctacac aaatttcaac tttccttaca ttgcagaatt tcaagacaat     300
gccataagtt tcagtggggc aattggatac ttgtattccg agaattttag aattgaagta     360
gaggcttctt atgaagaatt tgatgttaaa aatccagaag gatctgctac agacgcatac     420
aggtattttg cactagcacg tgctatggat ggcactaata aatctagtcc tgatgacaca     480
agaaaattca ctgtcatgag aaatgacggg ttatcaattt catcagtaat gataaatggg     540
tgttacaatt ttacattaga tgatatacca gtagtaccgt atgtatgcgc aggaatagga     600
ggagatttca tagagttttt taatgattta catgttaagt ttcgtcatca aggcaaggta     660
ggtattagtt attctatatc ccctgaagta agtttatttc ttaacggata ttaccataaa     720
gtaacaggta acagatttaa aaacttacac gttcaacacg taagtgattt aagtgacgct     780
cctaagttca catctgcagt tgctacactc aatgttgggt actttggtgg cgaaattgga     840
gtaagattta tattttaa                                                   858

<210> SEQ ID NO 30
<211> LENGTH: 285
<212> TYPE: PRT
<213> ORGANISM: Ehrlichia chaffeensis

<400> SEQUENCE: 30

Met Asn Asn Arg Lys Ser Phe Phe Ile Ile Gly Ala Ser Leu Leu Ala
1               5                  10                  15

Ser Leu Leu Phe Thr Ser Glu Ala Ser Ser Thr Gly Asn Val Ser Asn
                20                  25                  30

His Thr Tyr Phe Lys Pro Arg Leu Tyr Ile Ser Gly Gln Tyr Arg Pro
            35                  40                  45

Gly Val Ser His Phe Ser Lys Phe Ser Val Lys Glu Thr Asn Tyr Asn
        50                  55                  60

Thr Thr Gln Leu Val Gly Leu Lys Lys Asp Ile Ser Val Ile Gly Asn
65                  70                  75                  80

Ser Asn Ile Thr Thr Tyr Thr Asn Phe Asn Phe Pro Tyr Ile Ala Glu
```

```
                    85                  90                  95
Phe Gln Asp Asn Ala Ile Ser Phe Ser Gly Ala Ile Gly Tyr Leu Tyr
            100                 105                 110
Ser Glu Asn Phe Arg Ile Glu Val Glu Ala Ser Tyr Glu Glu Phe Asp
            115                 120                 125
Val Lys Asn Pro Glu Gly Ser Ala Thr Asp Ala Tyr Arg Tyr Phe Ala
            130                 135                 140
Leu Ala Arg Ala Met Asp Gly Thr Asn Lys Ser Ser Pro Asp Asp Thr
145                 150                 155                 160
Arg Lys Phe Thr Val Met Arg Asn Asp Gly Leu Ser Ile Ser Ser Val
                165                 170                 175
Met Ile Asn Gly Cys Tyr Asn Phe Thr Leu Asp Asp Ile Pro Val Val
            180                 185                 190
Pro Tyr Val Cys Ala Gly Ile Gly Gly Asp Phe Ile Glu Phe Phe Asn
            195                 200                 205
Asp Leu His Val Lys Phe Arg His Gln Gly Lys Val Gly Ile Ser Tyr
            210                 215                 220
Ser Ile Ser Pro Glu Val Ser Leu Phe Leu Asn Gly Tyr Tyr His Lys
225                 230                 235                 240
Val Thr Gly Asn Arg Phe Lys Asn Leu His Val Gln His Val Ser Asp
                245                 250                 255
Leu Ser Asp Ala Pro Lys Phe Thr Ser Ala Val Ala Thr Leu Asn Val
            260                 265                 270
Gly Tyr Phe Gly Gly Glu Ile Gly Val Arg Phe Ile Phe
            275                 280                 285

<210> SEQ ID NO 31
<211> LENGTH: 867
<212> TYPE: DNA
<213> ORGANISM: Ehrlichia canis

<400> SEQUENCE: 31
atgaattgca aaagattttt catagcaagt gcattgatat cactaatgtc tttcttacct      60
agcgtatctt tttctgaatc aatacatgaa gataatataa atggtaactt ttacattagt     120
gcaaagtata tgccaagtgc ctcacacttt ggcgtatttt cagttaaaga agagaaaaac     180
acaacaactg gagttttcgg attaaaacaa gattgggacg gagcaacaat aaaggatgca     240
agcagcagcc acacaataga cccaagtaca atattctcca tttcaaatta ttcatttaaa     300
tatgaaaaca atccatttttt agggtttgca ggagctattg ctactcaat gggtggtcca     360
agggtagagt ttgaagtgtc ttacgaaata tttgatgtaa aaaccaagg taacagttac     420
aagaacgatg ctcacaaata ttgcgcttta tcaagacaca ccggaggtat gccacaagcc     480
ggtcatcaaa ataaatttgt cttcctaaaa aatgaaggat tacttgacat atcacttatg     540
ataaacgcat gttatgatat aacaatcgac agcatgccat tttctccata tatatgtgca     600
ggtattggta gtgacttagt ttcgatgttt gaaactacaa atcctaaaat ttcttatcaa     660
ggaaaattag gtgtaagtta ctccataagc ccagaagcat ctgttttgt tggaggacac     720
tttcacagag ttataggtaa tgaatttaaa gacattcctg caataactcc tgctggagca     780
acagaaatta aaggcacaca gtttacaaca gtaacattaa acatatgcca cttcggacta     840
gagcttggag gcaggtttac tttttaa                                           867

<210> SEQ ID NO 32
<211> LENGTH: 288
```

<210> TYPE: PRT
<213> ORGANISM: Ehrlichia canis

<400> SEQUENCE: 32

Met Asn Cys Lys Arg Phe Phe Ile Ala Ser Ala Leu Ile Ser Leu Met
1               5                   10                  15

Ser Phe Leu Pro Ser Val Ser Phe Ser Glu Ser Ile His Glu Asp Asn
            20                  25                  30

Ile Asn Gly Asn Phe Tyr Ile Ser Ala Lys Tyr Met Pro Ser Ala Ser
        35                  40                  45

His Phe Gly Val Phe Ser Val Lys Glu Glu Lys Asn Thr Thr Thr Gly
    50                  55                  60

Val Phe Gly Leu Lys Gln Asp Trp Asp Gly Ala Thr Ile Lys Asp Ala
65                  70                  75                  80

Ser Ser Ser His Thr Ile Asp Pro Ser Thr Ile Phe Ser Ile Ser Asn
                85                  90                  95

Tyr Ser Phe Lys Tyr Glu Asn Asn Pro Phe Leu Gly Phe Ala Gly Ala
            100                 105                 110

Ile Gly Tyr Ser Met Gly Gly Pro Arg Val Glu Phe Glu Val Ser Tyr
        115                 120                 125

Glu Ile Phe Asp Val Lys Asn Gln Gly Asn Ser Tyr Lys Asn Asp Ala
130                 135                 140

His Lys Tyr Cys Ala Leu Ser Arg His Thr Gly Gly Met Pro Gln Ala
145                 150                 155                 160

Gly His Gln Asn Lys Phe Val Phe Leu Lys Asn Glu Gly Leu Leu Asp
                165                 170                 175

Ile Ser Leu Met Ile Asn Ala Cys Tyr Asp Ile Thr Ile Asp Ser Met
            180                 185                 190

Pro Phe Ser Pro Tyr Ile Cys Ala Gly Ile Gly Ser Asp Leu Val Ser
        195                 200                 205

Met Phe Glu Thr Thr Asn Pro Lys Ile Ser Tyr Gln Gly Lys Leu Gly
    210                 215                 220

Val Ser Tyr Ser Ile Ser Pro Glu Ala Ser Val Phe Val Gly Gly His
225                 230                 235                 240

Phe His Arg Val Ile Gly Asn Glu Phe Lys Asp Ile Pro Ala Ile Thr
                245                 250                 255

Pro Ala Gly Ala Thr Glu Ile Lys Gly Thr Gln Phe Thr Thr Val Thr
            260                 265                 270

Leu Asn Ile Cys His Phe Gly Leu Glu Leu Gly Gly Arg Phe Thr Phe
        275                 280                 285

<210> SEQ ID NO 33
<211> LENGTH: 864
<212> TYPE: DNA
<213> ORGANISM: Ehrlichia chaffeensis

<400> SEQUENCE: 33
atgaaatata aaaaaacttt tacagtaact gcattagtat tattaacttc ctttacacat      60
tttatacctt tttatagtcc agcacgtgcc agtacaattc acaacttcta cattagtgga     120
aaatatatgc caacagcgtc acattttgga attttttcag ctaaagaaga caaagttttt     180
actaaggtat tagttgggtt agatcaacga ttatcacata atattataaa caataatgat     240
acagcaaaga gtcttaaggt tcaaaattat tcatttaaat acaaaaataa cccatttcta     300
ggatttgcaa gagctattgg ttattcaata ggcaattcaa gaatagaact agaagtatca     360

```
catgaaatat tgatactaa aaacccagga acaattatt taaatgactc tcacaaatat      420
tgcgctttat ctcatggaag tcacatatgc agtgatggaa atagcggaga ttggtacact      480
gcaaaaactg ataagtttgt acttctgaaa atgaaggtt tacttgacgt ctcatttatg      540
ttaaacgcat gttatgacat aacaactgaa aaaatgcctt tttcacctta tatatgtgca      600
ggtattggta ctgatctcat atctatgttt gagacaacac aaaacaaaat atcttatcaa      660
ggaaagttag gtttaaacta tactataaac tcaagagttt ctgttttttgc aggtgggcac      720 tttcataaag taataggtaa tgaatttaaa ggtattccta ctctattacc tgatggatca      780
aacattaaag tacaacagtc tgcaacagta acattagatg tgtgccattt cgggttagag      840
attggaagta gatttttctt ttaa                                             864
```

<210> SEQ ID NO 34
<211> LENGTH: 287
<212> TYPE: PRT
<213> ORGANISM: Ehrlichia chaffeensis

<400> SEQUENCE: 34

```
Met Lys Tyr Lys Lys Thr Phe Thr Val Thr Ala Leu Val Leu Leu Thr
  1               5                  10                  15

Ser Phe Thr His Phe Ile Pro Phe Tyr Ser Pro Ala Arg Ala Ser Thr
             20                  25                  30

Ile His Asn Phe Tyr Ile Ser Gly Lys Tyr Met Pro Thr Ala Ser His
         35                  40                  45

Phe Gly Ile Phe Ser Ala Lys Glu Glu Gln Ser Phe Thr Lys Val Leu
     50                  55                  60

Val Gly Leu Asp Gln Arg Leu Ser His Asn Ile Ile Asn Asn Asn Asp
 65                  70                  75                  80

Thr Ala Lys Ser Leu Lys Val Gln Asn Tyr Ser Phe Lys Tyr Lys Asn
                 85                  90                  95

Asn Pro Phe Leu Gly Phe Ala Arg Ala Ile Gly Tyr Ser Ile Gly Asn
            100                 105                 110

Ser Arg Ile Glu Leu Glu Val Ser His Glu Ile Phe Asp Thr Lys Asn
        115                 120                 125

Pro Gly Asn Asn Tyr Leu Asn Asp Ser His Lys Tyr Cys Ala Leu Ser
    130                 135                 140

His Gly Ser His Ile Cys Ser Asp Gly Asn Ser Gly Asp Trp Tyr Thr
145                 150                 155                 160

Ala Lys Thr Asp Lys Phe Val Leu Leu Lys Asn Glu Gly Leu Leu Asp
                165                 170                 175

Val Ser Phe Met Leu Asn Ala Cys Tyr Asp Ile Thr Thr Glu Lys Met
            180                 185                 190

Pro Phe Ser Pro Tyr Ile Cys Ala Gly Ile Gly Thr Asp Leu Ile Ser
        195                 200                 205

Met Phe Glu Thr Thr Gln Asn Lys Ile Ser Tyr Gln Gly Lys Leu Gly
    210                 215                 220

Leu Asn Tyr Thr Ile Asn Ser Arg Val Ser Val Phe Ala Gly Gly His
225                 230                 235                 240

Phe His Lys Val Ile Gly Asn Glu Phe Lys Gly Ile Pro Thr Leu Leu
                245                 250                 255

Pro Asp Gly Ser Asn Ile Lys Val Gln Gln Ser Ala Thr Val Thr Leu
            260                 265                 270

Asp Val Cys His Phe Gly Leu Glu Ile Gly Ser Arg Phe Phe Phe
        275                 280                 285
```

<210> SEQ ID NO 35
<211> LENGTH: 924
<212> TYPE: DNA
<213> ORGANISM: Ehrlichia canis

<400> SEQUENCE: 35

```
atgttttata ctaatatata tattctggct tgtatttact ttgcacttcc actattgtta      60
atttattttc actattttag gtgtaatatg aattgcaaaa aaattcttat aacaactgca     120
ttaatatcat taatgtactc tattccaagc atatcttttt ctgatactat acaagatggt     180
aacatgggtg gtaacttcta tattagtgga agtatgtac caagtgtctc acattttggt      240
agcttctcag ctaaagaaga aagcaaatca actgttggag ttttggatt aaaacatgat      300
tgggatggaa gtccaatact taagaataaa cacgctgact tactgttcc aaactattcg      360
ttcagatacg agaacaatcc atttctaggg tttgcaggag ctatcggtta ctcaatgggt     420
ggcccaagaa tagaattcga aatatcttat gaagcattcg acgtaaaaag tcctaatatc     480
aattatcaaa atgacgcgca caggtactgc gctctatctc atcacacatc ggcagccatg     540
gaagctgata aatttgtctt cttaaaaaac gaagggttaa ttgacatatc acttgcaata     600
aatgcatgtt atgatataat aaatgacaaa gtacctgttt ctccttatat atgcgcaggt     660
attggtactg atttgatttc tatgtttgaa gctacaagtc ctaaaattc ctaccaagga      720
aaactgggca ttagttactc tattaatccg gaaacctctg ttttcatcgg tgggcatttc     780
cacaggatca taggtaatga gtttagagat attcctgcaa tagtacctag taactcaact     840
acaataagtg gaccacaatt tgcaacagta acactaaatg tgtgtcactt tggtttagaa     900
cttggaggaa gatttaactt ctaa                                            924
```

<210> SEQ ID NO 36
<211> LENGTH: 307
<212> TYPE: PRT
<213> ORGANISM: Ehrlichia canis

<400> SEQUENCE: 36

```
Met Phe Tyr Thr Asn Ile Tyr Ile Leu Ala Cys Ile Tyr Phe Ala Leu
  1               5                  10                  15

Pro Leu Leu Leu Ile Tyr Phe His Tyr Phe Arg Cys Asn Met Asn Cys
             20                  25                  30

Lys Lys Ile Leu Ile Thr Thr Ala Leu Ile Ser Leu Met Tyr Ser Ile
         35                  40                  45

Pro Ser Ile Ser Phe Ser Asp Thr Ile Gln Asp Gly Asn Met Gly Gly
     50                  55                  60

Asn Phe Tyr Ile Ser Gly Lys Tyr Val Pro Ser Val Ser His Phe Gly
 65                  70                  75                  80

Ser Phe Ser Ala Lys Glu Glu Ser Lys Ser Thr Val Gly Val Phe Gly
                 85                  90                  95

Leu Lys His Asp Trp Asp Gly Ser Pro Ile Leu Lys Asn Lys His Ala
            100                 105                 110

Asp Phe Thr Val Pro Asn Tyr Ser Phe Arg Tyr Glu Asn Asn Pro Phe
        115                 120                 125

Leu Gly Phe Ala Gly Ala Ile Gly Tyr Ser Met Gly Gly Pro Arg Ile
    130                 135                 140

Glu Phe Glu Ile Ser Tyr Glu Ala Phe Asp Val Lys Ser Pro Asn Ile
145                 150                 155                 160
```

```
Asn Tyr Gln Asn Asp Ala His Arg Tyr Cys Ala Leu Ser His His Thr
                165                 170                 175

Ser Ala Ala Met Glu Ala Asp Lys Phe Val Phe Leu Lys Asn Glu Gly
            180                 185                 190

Leu Ile Asp Ile Ser Leu Ala Ile Asn Ala Cys Tyr Asp Ile Ile Asn
        195                 200                 205

Asp Lys Val Pro Val Ser Pro Tyr Ile Cys Ala Gly Ile Gly Thr Asp
    210                 215                 220

Leu Ile Ser Met Phe Glu Ala Thr Ser Pro Lys Ile Ser Tyr Gln Gly
225                 230                 235                 240

Lys Leu Gly Ile Ser Tyr Ser Ile Asn Pro Glu Thr Ser Val Phe Ile
                245                 250                 255

Gly Gly His Phe His Arg Ile Ile Gly Asn Glu Phe Arg Asp Ile Pro
            260                 265                 270

Ala Ile Val Pro Ser Asn Ser Thr Thr Ile Ser Gly Pro Gln Phe Ala
        275                 280                 285

Thr Val Thr Leu Asn Val Cys His Phe Gly Leu Glu Leu Gly Gly Arg
    290                 295                 300

Phe Asn Phe
305
```

<210> SEQ ID NO 37
<211> LENGTH: 843
<212> TYPE: DNA
<213> ORGANISM: Ehrlichia canis

<400> SEQUENCE: 37

| | | | | | |
|---|---|---|---|---|---|
| atgaattgca | aaaaaattct | ataacaact | gcattaatgt | cattaatgta | ctatgctcca | 60 |
| agcatatctt | tttctgatac | tatacaagac | gataacactg | gtagcttcta | catcagtgga | 120 |
| aaatatgtac | caagtgtttc | acattttggt | gttttctcag | ctaaagaaga | agaaactca | 180 |
| actgttggag | tttttggatt | aaaacatgat | tggaatggag | gtacaatatc | taactcttct | 240 |
| ccagaaaata | tattcacagt | tcaaaattat | tcgtttaaat | acgaaaacaa | cccattctta | 300 |
| gggtttgcag | gagctattgg | ttattcaatg | ggtggcccaa | gaatagaact | tgaagttctg | 360 |
| tacgagacat | tcgatgtgaa | aaatcagaac | aataattata | gaacggcgc | acacagatac | 420 |
| tgtgctttat | ctcatcatag | ttcagcaaca | acatgtcct | ccgcaagtaa | caaatttgtt | 480 |
| ttcttaaaaa | atgaagggtt | aattgactta | tcatttatga | taaatgcatg | ctatgacata | 540 |
| ataattgaag | gaatgccttt | ttcacccttat | atttgtgcag | gtgttggtac | tgatgttgtt | 600 |
| tccatgtttg | aagctataaa | tcctaaaatt | tcttaccaag | gaaaactagg | attaggttat | 660 |
| agtataagtt | cagaagcctc | tgtttttatc | ggtggacact | tcacagagt | cataggtaat | 720 |
| gaatttagag | acatccctgc | tatggttcct | agtggatcaa | atcttccaga | aaaccaattt | 780 |
| gcaatagtaa | cactaaatgt | gtgtcacttt | ggtttagaac | ttggaggaag | atttaacttc | 840 |
| tga | | | | | | 843 |

<210> SEQ ID NO 38
<211> LENGTH: 280
<212> TYPE: PRT
<213> ORGANISM: Ehrlichia canis

<400> SEQUENCE: 38

```
Met Asn Cys Lys Lys Ile Leu Ile Thr Thr Ala Leu Met Ser Leu Met
  1               5                  10                  15
```

Tyr Tyr Ala Pro Ser Ile Ser Phe Ser Asp Thr Ile Gln Asp Asp Asn
            20                  25                  30
Thr Gly Ser Phe Tyr Ile Ser Gly Lys Tyr Val Pro Ser Val Ser His
        35                  40                  45
Phe Gly Val Phe Ser Ala Lys Glu Glu Arg Asn Ser Thr Val Gly Val
    50                  55                  60
Phe Gly Leu Lys His Asp Trp Asn Gly Thr Ile Ser Asn Ser Ser
65                  70                  75                  80
Pro Glu Asn Ile Phe Thr Val Gln Asn Tyr Ser Phe Lys Tyr Glu Asn
                85                  90                  95
Asn Pro Phe Leu Gly Phe Ala Gly Ala Ile Gly Tyr Ser Met Gly Gly
            100                 105                 110
Pro Arg Ile Glu Leu Glu Val Leu Tyr Glu Thr Phe Asp Val Lys Asn
        115                 120                 125
Gln Asn Asn Asn Tyr Lys Asn Gly Ala His Arg Tyr Cys Ala Leu Ser
    130                 135                 140
His His Ser Ser Ala Thr Asn Met Ser Ser Ala Ser Asn Lys Phe Val
145                 150                 155                 160
Phe Leu Lys Asn Glu Gly Leu Ile Asp Leu Ser Phe Met Ile Asn Ala
                165                 170                 175
Cys Tyr Asp Ile Ile Ile Glu Gly Met Pro Phe Ser Pro Tyr Ile Cys
            180                 185                 190
Ala Gly Val Gly Thr Asp Val Val Ser Met Phe Glu Ala Ile Asn Pro
        195                 200                 205
Lys Ile Ser Tyr Gln Gly Lys Leu Gly Leu Gly Tyr Ser Ile Ser Ser
    210                 215                 220
Glu Ala Ser Val Phe Ile Gly Gly His Phe His Arg Val Ile Gly Asn
225                 230                 235                 240
Glu Phe Arg Asp Ile Pro Ala Met Val Pro Ser Gly Ser Asn Leu Pro
                245                 250                 255
Glu Asn Gln Phe Ala Ile Val Thr Leu Asn Val Cys His Phe Gly Leu
            260                 265                 270
Glu Leu Gly Gly Arg Phe Asn Phe
        275                 280

<210> SEQ ID NO 39
<211> LENGTH: 852
<212> TYPE: DNA
<213> ORGANISM: Ehrlichia canis

<400> SEQUENCE: 39
atgaattgta aaaagttttt cacaataagt gcattgatat catccatata cttcctacct    60
aatgtctcat actctaaccc agtatatggt aacagtatgt atggtaattt ttacatatca   120
ggaaagtaca tgccaagtgt tcctcatttt ggaattttt cagctgaaga agagaaaaaa   180
aagacaactg tagtatatgg cttaaaagga aaactggcag agatgcaat atctagtcaa   240
agtccagatg ataattttac cattcgaaat tactcattca gtatgcaag caacaagttt   300
ttagggtttg cagtagctat tggttactcg ataggcagtc aagaataga agttgagatg   360
tcttatgaag catttgatgt gaaaaatcca ggtgataatt acaaaaacgg tgcttacagg   420
tattgtgctt tatctcatca agatgatgcg gatgatgaca tgactagtgc aactgacaaa   480
tttgtatatt taattaatga aggattactt aacatatcat ttatgacaaa catatgttat   540
gaaacagcaa gcaaaaatat acctctctct ccttacatat gtgcaggtat tggtactgat   600

```
ttaattcaca tgtttgaaac tacacatcct aaaatttctt atcaaggaaa gctagggttg    660
gcctacttcg taagtgcaga gtcttcggtt tcttttggta tatattttca taaaattata    720
aataataagt ttaaaaatgt tccagccatg gtacctatta actcagacga gatagtagga    780
ccacagtttg caacagtaac attaaatgta tgctactttg gattagaact tggatgtagg    840
ttcaacttct aa                                                         852
```

<210> SEQ ID NO 40
<211> LENGTH: 283
<212> TYPE: PRT
<213> ORGANISM: Ehrlichia canis

<400> SEQUENCE: 40

```
Met Asn Cys Lys Lys Val Phe Thr Ile Ser Ala Leu Ile Ser Ser Ile
  1               5                  10                  15

Tyr Phe Leu Pro Asn Val Ser Tyr Ser Asn Pro Val Tyr Gly Asn Ser
                 20                  25                  30

Met Tyr Gly Asn Phe Tyr Ile Ser Gly Lys Tyr Met Pro Ser Val Pro
             35                  40                  45

His Phe Gly Ile Phe Ser Ala Glu Glu Lys Lys Lys Thr Thr Val
 50                  55                  60

Val Tyr Gly Leu Lys Gly Lys Leu Ala Gly Asp Ala Ile Ser Ser Gln
 65                  70                  75                  80

Ser Pro Asp Asp Asn Phe Thr Ile Arg Asn Tyr Ser Phe Lys Tyr Ala
                 85                  90                  95

Ser Asn Lys Phe Leu Gly Phe Ala Val Ala Ile Gly Tyr Ser Ile Gly
            100                 105                 110

Ser Pro Arg Ile Glu Val Glu Met Ser Tyr Glu Ala Phe Asp Val Lys
            115                 120                 125

Asn Pro Gly Asp Asn Tyr Lys Asn Gly Ala Tyr Arg Tyr Cys Ala Leu
        130                 135                 140

Ser His Gln Asp Asp Ala Asp Asp Met Thr Ser Ala Thr Asp Lys
145                 150                 155                 160

Phe Val Tyr Leu Ile Asn Glu Gly Leu Leu Asn Ile Ser Phe Met Thr
                165                 170                 175

Asn Ile Cys Tyr Glu Thr Ala Ser Lys Asn Ile Pro Leu Ser Pro Tyr
            180                 185                 190

Ile Cys Ala Gly Ile Gly Thr Asp Leu Ile His Met Phe Glu Thr Thr
        195                 200                 205

His Pro Lys Ile Ser Tyr Gln Gly Lys Leu Gly Leu Ala Tyr Phe Val
    210                 215                 220

Ser Ala Glu Ser Ser Val Ser Phe Gly Ile Tyr Phe His Lys Ile Ile
225                 230                 235                 240

Asn Asn Lys Phe Lys Asn Val Pro Ala Met Val Pro Ile Asn Ser Asp
                245                 250                 255

Glu Ile Val Gly Pro Gln Phe Ala Thr Val Thr Leu Asn Val Cys Tyr
            260                 265                 270

Phe Gly Leu Glu Leu Gly Cys Arg Phe Asn Phe
        275                 280
```

<210> SEQ ID NO 41
<211> LENGTH: 831
<212> TYPE: DNA
<213> ORGANISM: Ehrlichia canis

<400> SEQUENCE: 41

-continued

```
atgaactgta aaaaatttct tataacaact acattggtat cactaacaat tcttttacct      60
ggcatatctt tctccaaacc aatacatgaa acaatacta caggaaactt ttacattatt     120
ggaaaatatg taccaagtat ttcacatttt gggaactttt cagctaaaga agaaaaaaac    180
acaactactg gattttttgg attaaaagaa tcatggactg gtggtatcat ccttgataaa    240
gaacatgcag cttttaatat cccaaattat tcatttaaat atgaaaataa tccattttta    300
ggatttgcag gggtaattgg ctattcaata ggtagtccaa gaatagaatt tgaagtatca    360
tacgagacat tcgatgtaca aaatccagga gataagttta acaatgatgc acataagtat    420
tgtgctttat ccaatgattc cagtaaaaca atgaaaagtg gtaaattcgt ttttctcaaa    480
aatgaaggat taagtgacat atcactcatg ttaaatgtat gttatgatat aataaacaaa    540
agaatgcctt tttcaccta catatgtgca ggcattggta ctgacttaat attcatgttt    600
gacgctataa accataaagc tgcttatcaa ggaaaattag ttttaattta tccaataagc    660
ccagaagcta acatttctat gggtgtgcac tttcacaaag taacaaacaa cgagtttaga    720
gttcctgttc tattaactgc tggaggactc gctccagata atctatttgc aatagtaaag    780
ttgagtatat gtcattttgg gttagaattt gggtacaggg tcagttttta a             831
```

<210> SEQ ID NO 42
<211> LENGTH: 276
<212> TYPE: PRT
<213> ORGANISM: Ehrlichia canis

<400> SEQUENCE: 42

```
Met Asn Cys Lys Lys Phe Leu Ile Thr Thr Thr Leu Val Ser Leu Thr
  1               5                  10                  15

Ile Leu Leu Pro Gly Ile Ser Phe Ser Lys Pro Ile His Glu Asn Asn
             20                  25                  30

Thr Thr Gly Asn Phe Tyr Ile Ile Gly Lys Tyr Val Pro Ser Ile Ser
         35                  40                  45

His Phe Gly Asn Phe Ser Ala Lys Glu Glu Lys Asn Thr Thr Thr Gly
     50                  55                  60

Ile Phe Gly Leu Lys Glu Ser Trp Thr Gly Gly Ile Ile Leu Asp Lys
 65                  70                  75                  80

Glu His Ala Ala Phe Asn Ile Pro Asn Tyr Ser Phe Lys Tyr Glu Asn
                 85                  90                  95

Asn Pro Phe Leu Gly Phe Ala Gly Val Ile Gly Tyr Ser Ile Gly Ser
            100                 105                 110

Pro Arg Ile Glu Phe Glu Val Ser Tyr Glu Thr Phe Asp Val Gln Asn
        115                 120                 125

Pro Gly Asp Lys Phe Asn Asn Asp Ala His Lys Tyr Cys Ala Leu Ser
    130                 135                 140

Asn Asp Ser Ser Lys Thr Met Lys Ser Gly Lys Phe Val Phe Leu Lys
145                 150                 155                 160

Asn Glu Gly Leu Ser Asp Ile Ser Leu Met Leu Asn Val Cys Tyr Asp
                165                 170                 175

Ile Ile Asn Lys Arg Met Pro Phe Ser Pro Tyr Ile Cys Ala Gly Ile
            180                 185                 190

Gly Thr Asp Leu Ile Phe Met Phe Asp Ala Ile Asn His Lys Ala Ala
        195                 200                 205

Tyr Gln Gly Lys Leu Gly Phe Asn Tyr Pro Ile Ser Pro Glu Ala Asn
    210                 215                 220
```

-continued

```
Ile Ser Met Gly Val His Phe His Lys Val Thr Asn Asn Glu Phe Arg
225                 230                 235                 240

Val Pro Val Leu Leu Thr Ala Gly Gly Leu Ala Pro Asp Asn Leu Phe
                245                 250                 255

Ala Ile Val Lys Leu Ser Ile Cys His Phe Gly Leu Glu Phe Gly Tyr
            260                 265                 270

Arg Val Ser Phe
        275

<210> SEQ ID NO 43
<211> LENGTH: 882
<212> TYPE: DNA
<213> ORGANISM: Ehrlichia canis

<400> SEQUENCE: 43
atgaataata aactcaaatt tactataata aacacagtat tagtatgctt attgtcatta     60
cctaatatat cttcctcaaa ggccataaac aataacgcta aaaagtacta cggattatat    120
atcagtggac aatataaacc cagtgtttct gttttcagta atttttcagt taaagaaacc    180
aatgtcataa ctaaaaacct tatagcttta aaaaaagatg ttgactctat tgaaaccaag    240
actgatgcca gtgtaggtat tagtaaccca tcaaatttta ctatccccta tacagctgta    300
tttcaagata attctgtcaa tttcaatgga actattggtt acacctttgc tgaaggtaca    360
agagttgaaa tagaaggttc ttatgaggaa tttgatgtta aaaaccctgg aggctataca    420
ctaagtgatg cctatcgcta ttttgcatta gcacgtgaaa tgaaaggtaa tagttttaca    480
cctaaagaaa aagtttctaa tagttttttt cacactgtaa tgagaaatga tggattatct    540
ataatatctg ttatagtaaa tgtttgctac gatttctctt tgaacaattt gtcaatatcg    600
ccttacatat gtggaggagc aggggtagat gctatagaat tcttcgatgt attacacatt    660
aagtttgcat atcaaagcaa gctaggtatt gcttattctc taccatctaa cattagtctc    720
tttgctagtt tatattacca taaagtaatg ggcaatcaat ttaaaaattt aaatgtccaa    780
gatgttgctg aacttgcaag tatacctaaa attacatccg cagttgctac acttaatatt    840
ggttattttg gaggtgaaat tggtgcaaga ttgacatttt aa                       882

<210> SEQ ID NO 44
<211> LENGTH: 293
<212> TYPE: PRT
<213> ORGANISM: Ehrlichia canis

<400> SEQUENCE: 44

Met Asn Asn Lys Leu Lys Phe Thr Ile Ile Asn Thr Val Leu Val Cys
  1               5                  10                  15

Leu Leu Ser Leu Pro Asn Ile Ser Ser Ser Lys Ala Ile Asn Asn Asn
             20                  25                  30

Ala Lys Lys Tyr Tyr Gly Leu Tyr Ile Ser Gly Gln Tyr Lys Pro Ser
         35                  40                  45

Val Ser Val Phe Ser Asn Phe Ser Val Lys Glu Thr Asn Val Ile Thr
     50                  55                  60

Lys Asn Leu Ile Ala Leu Lys Lys Asp Val Asp Ser Ile Glu Thr Lys
 65                  70                  75                  80

Thr Asp Ala Ser Val Gly Ile Ser Asn Pro Ser Asn Phe Thr Ile Pro
                 85                  90                  95

Tyr Thr Ala Val Phe Gln Asp Asn Ser Val Asn Phe Asn Gly Thr Ile
            100                 105                 110
```

```
Gly Tyr Thr Phe Ala Glu Gly Thr Arg Val Glu Ile Glu Gly Ser Tyr
        115                 120                 125

Glu Glu Phe Asp Val Lys Asn Pro Gly Gly Tyr Thr Leu Ser Asp Ala
        130                 135                 140

Tyr Arg Tyr Phe Ala Leu Ala Arg Glu Met Lys Gly Asn Ser Phe Thr
145                 150                 155                 160

Pro Lys Glu Lys Val Ser Asn Ser Phe Phe His Thr Val Met Arg Asn
                165                 170                 175

Asp Gly Leu Ser Ile Ile Ser Val Ile Val Asn Val Cys Tyr Asp Phe
            180                 185                 190

Ser Leu Asn Asn Leu Ser Ile Ser Pro Tyr Ile Cys Gly Gly Ala Gly
        195                 200                 205

Val Asp Ala Ile Glu Phe Phe Asp Val Leu His Ile Lys Phe Ala Tyr
    210                 215                 220

Gln Ser Lys Leu Gly Ile Ala Tyr Ser Leu Pro Ser Asn Ile Ser Leu
225                 230                 235                 240

Phe Ala Ser Leu Tyr Tyr His Lys Val Met Gly Asn Gln Phe Lys Asn
                245                 250                 255

Leu Asn Val Gln Asp Val Ala Glu Leu Ala Ser Ile Pro Lys Ile Thr
            260                 265                 270

Ser Ala Val Ala Thr Leu Asn Ile Gly Tyr Phe Gly Gly Glu Ile Gly
        275                 280                 285

Ala Arg Leu Thr Phe
    290

<210> SEQ ID NO 45
<211> LENGTH: 900
<212> TYPE: DNA
<213> ORGANISM: Ehrlichia canis

<400> SEQUENCE: 45
atgaatagca agagtaagtt ctttacaata tgtacatcgt taatatgctt attatcatca      60
cctaacacat ctctctcaaa cttcataggc aatagtacaa acattctgg attatatgtt     120 agcggacatt ataagcccag cgtttccatt tttagcaaat tttcagtaaa agaaacaaat     180
acacatacag tacagttagt agctcttaaa aaagatgtta attctatttc tatgaacatc     240
agtaatggtg ctacaggcat tagcaaagca acaaatttta atcttcctta tgttgcagaa     300
tttcaagaca atgccttcaa cttcagtgga gctattggtt attcactttt tgaacaacta     360
aacattgaag ttgaaggttc ttatgaagaa ttcgatgcca aaaatcctgg tggttatatt     420
ttaaatgatg cattccgcta ttttgcattg gcacgtgaaa tgggacaaga aaaaaatgat     480
aataagcatc ttagtcctaa ggaggagcat gatataagta aaacatatta cacagtcatg     540
agaaataatg ggttatctat attatctatt atgataaatg ctgctataa tctacctctc     600 aatgatttat caatatcacc ttattttgt acaggaatag tgtagatgc tatagaattt     660 tttgatgcac tgcatcttaa acttgctttg caaagtaaaa taggagctac ttaccaatta     720
tcagacaaca ttagtttatt tacaaatgga tattaccatc aagtaatagg tgatcaattt     780
aaaaacttaa agtccaata taggtgaa cttaagaga acccgaaaat tacatctgca     840
gttgctactc tcaatgttgg atactttgga ggtgaaattg gagtaagact cacactttaa     900

<210> SEQ ID NO 46
<211> LENGTH: 299
<212> TYPE: PRT
<213> ORGANISM: Ehrlichia canis
```

<400> SEQUENCE: 46

```
Met Asn Ser Lys Ser Lys Phe Phe Thr Ile Cys Thr Ser Leu Ile Cys
 1               5                  10                  15
Leu Leu Ser Ser Pro Asn Thr Ser Leu Ser Asn Phe Ile Gly Asn Ser
            20                  25                  30
Thr Lys His Ser Gly Leu Tyr Val Ser Gly His Tyr Lys Pro Ser Val
        35                  40                  45
Ser Ile Phe Ser Lys Phe Ser Val Lys Glu Thr Asn Thr His Thr Val
    50                  55                  60
Gln Leu Val Ala Leu Lys Lys Asp Val Asn Ser Ile Ser Met Asn Ile
65                  70                  75                  80
Ser Asn Gly Ala Thr Gly Ile Ser Lys Ala Thr Asn Phe Asn Leu Pro
                85                  90                  95
Tyr Val Ala Glu Phe Gln Asp Asn Ala Phe Asn Phe Ser Gly Ala Ile
            100                 105                 110
Gly Tyr Ser Leu Phe Glu Gln Leu Asn Ile Glu Val Glu Gly Ser Tyr
        115                 120                 125
Glu Glu Phe Asp Ala Lys Asn Pro Gly Gly Tyr Ile Leu Asn Asp Ala
    130                 135                 140
Phe Arg Tyr Phe Ala Leu Ala Arg Glu Met Gly Gln Glu Lys Asn Asp
145                 150                 155                 160
Asn Lys His Leu Ser Pro Lys Glu Glu His Asp Ile Ser Lys Thr Tyr
                165                 170                 175
Tyr Thr Val Met Arg Asn Asn Gly Leu Ser Ile Leu Ser Ile Met Ile
            180                 185                 190
Asn Gly Cys Tyr Asn Leu Pro Leu Asn Asp Leu Ser Ile Ser Pro Tyr
        195                 200                 205
Phe Cys Thr Gly Ile Gly Val Asp Ala Ile Glu Phe Phe Asp Ala Leu
    210                 215                 220
His Leu Lys Leu Ala Leu Gln Ser Lys Ile Gly Ala Thr Tyr Gln Leu
225                 230                 235                 240
Ser Asp Asn Ile Ser Leu Phe Thr Asn Gly Tyr Tyr His Gln Val Ile
                245                 250                 255
Gly Asp Gln Phe Lys Asn Leu Lys Val Gln Tyr Ile Gly Glu Leu Lys
            260                 265                 270
Glu Asn Pro Lys Ile Thr Ser Ala Val Ala Thr Leu Asn Val Gly Tyr
        275                 280                 285
Phe Gly Gly Glu Ile Gly Val Arg Leu Thr Leu
    290                 295
```

<210> SEQ ID NO 47
<211> LENGTH: 843
<212> TYPE: DNA
<213> ORGANISM: Ehrlichia canis

<400> SEQUENCE: 47

```
atgaattata agaaaattct agtaagaagc gcgttaatct cattaatgtc aatcttacca      60
tatcagtctt ttgcagatcc tgtaggttca agaactaatg ataacaaaga aggcttctac     120
attagtgcaa agtacaatcc aagtatatca cactttagaa aattctctgc tgaagaaact     180
cctattaatg aacaaattc tctcactaaa aaagttttcg gactaaagaa agatggtgat     240
ataacaaaaa aagacgattt tacaagagta gctccaggca ttgattttca aaataactta     300
atatcaggat tttcaggaag tattggttac tctatggacg gaccaagaat agaacttgaa     360
```

```
gctgcatatc aacaatttaa tccaaaaaac accgataaca atgatactga taatggtgaa    420
tactataaac attttgcatt atctcgtaaa gatgcaatgg aagatcagca atatgtagta    480
cttaaaaatg acggcataac ttttatgtca ttgatggtta atacttgcta tgacattaca    540
gctgaaggag tatctttcgt accatatgca tgtgcaggta taggagcaga tcttatcact    600 attttaaag acctcaatct aaaatttgct taccaaggaa aaataggtat tagttaccct     660
atcacaccag aagtctctgc atttattggt ggatactacc atggcgttat tggtaataaa    720
tttgagaaga tacctgtaat aactcctgta gtattaaatg atgctcctca aaccacatct    780
gcttcagtaa ctcttgacgt tggatacttt ggcggagaaa ttggaatgag gttcaccttc    840
taa                                                                  843
```

<210> SEQ ID NO 48
<211> LENGTH: 280
<212> TYPE: PRT
<213> ORGANISM: Ehrlichia canis
<400> SEQUENCE: 48

```
Met Asn Tyr Lys Lys Ile Leu Val Arg Ser Ala Leu Ile Ser Leu Met
 1               5                  10                  15

Ser Ile Leu Pro Tyr Gln Ser Phe Ala Asp Pro Val Gly Ser Arg Thr
            20                  25                  30

Asn Asp Asn Lys Glu Gly Phe Tyr Ile Ser Ala Lys Tyr Asn Pro Ser
        35                  40                  45

Ile Ser His Phe Arg Lys Phe Ser Ala Glu Glu Thr Pro Ile Asn Gly
    50                  55                  60

Thr Asn Ser Leu Thr Lys Lys Val Phe Gly Leu Lys Lys Asp Gly Asp
65                  70                  75                  80

Ile Thr Lys Lys Asp Asp Phe Thr Arg Val Ala Pro Gly Ile Asp Phe
                85                  90                  95

Gln Asn Asn Leu Ile Ser Gly Phe Ser Gly Ser Ile Gly Tyr Ser Met
            100                 105                 110

Asp Gly Pro Arg Ile Glu Leu Glu Ala Ala Tyr Gln Gln Phe Asn Pro
        115                 120                 125

Lys Asn Thr Asp Asn Asn Asp Thr Asp Asn Gly Glu Tyr Tyr Lys His
    130                 135                 140

Phe Ala Leu Ser Arg Lys Asp Ala Met Glu Asp Gln Gln Tyr Val Val
145                 150                 155                 160

Leu Lys Asn Asp Gly Ile Thr Phe Met Ser Leu Met Val Asn Thr Cys
                165                 170                 175

Tyr Asp Ile Thr Ala Glu Gly Val Ser Phe Val Pro Tyr Ala Cys Ala
            180                 185                 190

Gly Ile Gly Ala Asp Leu Ile Thr Ile Phe Lys Asp Leu Asn Leu Lys
        195                 200                 205

Phe Ala Tyr Gln Gly Lys Ile Gly Ile Ser Tyr Pro Ile Thr Pro Glu
    210                 215                 220

Val Ser Ala Phe Ile Gly Gly Tyr Tyr His Gly Val Ile Gly Asn Lys
225                 230                 235                 240

Phe Glu Lys Ile Pro Val Ile Thr Pro Val Val Leu Asn Asp Ala Pro
                245                 250                 255

Gln Thr Thr Ser Ala Ser Val Thr Leu Asp Val Gly Tyr Phe Gly Gly
            260                 265                 270

Glu Ile Gly Met Arg Phe Thr Phe
        275                 280
```

-continued

```
275 280

<210> SEQ ID NO 49
<211> LENGTH: 903
<212> TYPE: DNA
<213> ORGANISM: Ehrlichia chaffeensis
<400> SEQUENCE: 49
atgaagaaga aaaatcaatt tatcacaata agtacaatat tagtatgttt attgtcatta 60
tctaatgcat cactttcaaa cactacaaat agcagcacta aaaaacagtt tgggttatat 120
gttagtggac aatacaagcc tagtgtttct atttttagca atttctcagt aaaggaaact 180
aattttccta caaagtatct agcagctctt aaaaaagaca ttaattctgt cgaatttgac 240
gatagtgtta ctgctggcat tagttaccca cttaatttca gtactcctta tatagctgta 300
tttcaagata atatttctaa ttttaatggc gctattgggt acacttttgt tgaaggccca 360
agaattgaaa tagaaggttc ttatgaagaa ttcgatgtca aagacctgga agatatacag 420
aaatacaaga tgcataccgt tgactttgct ttagcacgtg atatagactc tattcctact 480
agcccaaaaa atagaacttc acatgatggc aacagttcat ataaggtata ccacactgta 540
atgaaaaatg aaggactatc tataatatcc attatggtca atggctgcta tgatttttct 600
tcagataatt tatcaatatt accttatgta tgtggtggta taggtgtaaa tgctatagag 660
tttttcgatg cattacatgt taaattcgcg tgtcagggta aattaggtat tacttatcca 720
ttatcttcca acgttagttt atttgctggt ggatattatc accaagtaat gggcaaccaa 780
tttaaaaatc taaatgttca acatgtagct gaacttaatg acgcacccaa agttacatct 840
gcagtagcta cacttgacat tgggtatttt ggtggtgaaa ttggagcaag gcttatattt 900
taa 903

<210> SEQ ID NO 50
<211> LENGTH: 300
<212> TYPE: PRT
<213> ORGANISM: Ehrlichia chaffeensis

<400> SEQUENCE: 50

Met Lys Lys Lys Asn Gln Phe Ile Thr Ile Ser Thr Ile Leu Val Cys
1 5 10 15

Leu Leu Ser Leu Ser Asn Ala Ser Leu Ser Asn Thr Thr Asn Ser Ser
20 25 30

Thr Lys Lys Gln Phe Gly Leu Tyr Val Ser Gly Gln Tyr Lys Pro Ser
35 40 45

Val Ser Ile Phe Ser Asn Phe Ser Val Lys Glu Thr Asn Phe Pro Thr
50 55 60

Lys Tyr Leu Ala Ala Leu Lys Lys Asp Ile Asn Ser Val Glu Phe Asp
65 70 75 80

Asp Ser Val Thr Ala Gly Ile Ser Tyr Pro Leu Asn Phe Ser Thr Pro
85 90 95

Tyr Ile Ala Val Phe Gln Asp Asn Ile Ser Asn Phe Asn Gly Ala Ile
100 105 110

Gly Tyr Thr Phe Val Glu Gly Pro Arg Ile Glu Ile Glu Gly Ser Tyr
115 120 125

Glu Glu Phe Asp Val Lys Asp Leu Glu Asp Ile Gln Lys Tyr Lys Met
130 135 140

His Thr Val Asp Phe Ala Leu Ala Arg Asp Ile Asp Ser Ile Pro Thr
145 150 155 160
```

Ser Pro Lys Asn Arg Thr Ser His Asp Gly Asn Ser Ser Tyr Lys Val
            165                 170                 175

Tyr His Thr Val Met Lys Asn Glu Gly Leu Ser Ile Ile Ser Ile Met
            180                 185                 190

Val Asn Gly Cys Tyr Asp Phe Ser Ser Asp Asn Leu Ser Ile Leu Pro
            195                 200                 205

Tyr Val Cys Gly Gly Ile Gly Val Asn Ala Ile Glu Phe Phe Asp Ala
        210                 215                 220

Leu His Val Lys Phe Ala Cys Gln Gly Lys Leu Gly Ile Thr Tyr Pro
225                 230                 235                 240

Leu Ser Ser Asn Val Ser Leu Phe Ala Gly Gly Tyr Tyr His Gln Val
            245                 250                 255

Met Gly Asn Gln Phe Lys Asn Leu Asn Val Gln His Val Ala Glu Leu
            260                 265                 270

Asn Asp Ala Pro Lys Val Thr Ser Ala Val Ala Thr Leu Asp Ile Gly
            275                 280                 285

Tyr Phe Gly Gly Glu Ile Gly Ala Arg Leu Ile Phe
        290                 295                 300

<210> SEQ ID NO 51
<211> LENGTH: 897
<212> TYPE: DNA
<213> ORGANISM: Ehrlichia chaffeensis

<400> SEQUENCE: 51
atgaatcaca aaagtatgct ctttacaata ggtacagctt tgatatcctt attgtcatta      60
cctaatgtat cattctcagg aatcataaat aacaatgcta acaatttagg tatatacatt     120
agtgggcaat ataaacccag tgtttctgtt tttagcaatt tctcagtaaa agaaactaac     180
ttcactacac aacagttagt agcacttaaa aaagatattg attctgttga cattagtacc     240
aatgctgata gcggtattaa taatccgcag aatttcacta tcccttatat accaaaattt     300
caagacaatg ctgctagttt tagtggagca cttggattct tctacgctag aggtttaaga     360
cttgaaatgg aaggttccta tgaagaattt gatgttaaaa accctggagg atatacaaaa     420
gtaaaagatg catatcgtta ctttgccctg gcacgtgaga tgcaatctgg tcaaacttgc     480
cctaaacaca agaaacatc aggtattcaa cctcacggta tttatcacac tgttatgagg      540
aatgatgggg tatctatttc atctgtcata atcaatggtt gttataactt tactttaagt     600
aatctaccaa tatcaccttta catgtgtgta ggtatgggaa tagatgctat acaattttttt    660 gattcactac atattaagtt tgcacatcaa agtaagttag gtattactta cccactatct     720
tcaaatgttc atttatttgc tgatagctat tatcataaag taataggtaa taaatttaaa     780
aatctaaggg ttcaacacgt ttatgaatta caacaggtac ctaaagttac atctgctgtt     840
gctacacttg atattgggta ttttggtggt gaagttggag taaggtttat actttaa       897

<210> SEQ ID NO 52
<211> LENGTH: 298
<212> TYPE: PRT
<213> ORGANISM: Ehrlichia chaffeensis

<400> SEQUENCE: 52

Met Asn His Lys Ser Met Leu Phe Thr Ile Gly Thr Ala Leu Ile Ser
  1               5                  10                  15

Leu Leu Ser Leu Pro Asn Val Ser Phe Ser Gly Ile Ile Asn Asn Asn
            20                  25                  30

Ala Asn Asn Leu Gly Ile Tyr Ile Ser Gly Gln Tyr Lys Pro Ser Val
            35                  40                  45

Ser Val Phe Ser Asn Phe Ser Val Lys Glu Thr Asn Phe Thr Thr Gln
        50                  55                  60

Gln Leu Val Ala Leu Lys Lys Asp Ile Asp Ser Val Asp Ile Ser Thr
65                  70                  75                  80

Asn Ala Asp Ser Gly Ile Asn Asn Pro Gln Asn Phe Thr Ile Pro Tyr
                85                  90                  95

Ile Pro Lys Phe Gln Asp Asn Ala Ala Ser Phe Ser Gly Ala Leu Gly
            100                 105                 110

Phe Phe Tyr Ala Arg Gly Leu Arg Leu Glu Met Glu Gly Ser Tyr Glu
        115                 120                 125

Glu Phe Asp Val Lys Asn Pro Gly Gly Tyr Thr Lys Val Lys Asp Ala
    130                 135                 140

Tyr Arg Tyr Phe Ala Leu Ala Arg Glu Met Gln Ser Gly Gln Thr Cys
145                 150                 155                 160

Pro Lys His Lys Glu Thr Ser Gly Ile Gln Pro His Gly Ile Tyr His
                165                 170                 175

Thr Val Met Arg Asn Asp Gly Val Ser Ile Ser Ser Val Ile Ile Asn
            180                 185                 190

Gly Cys Tyr Asn Phe Thr Leu Ser Asn Leu Pro Ile Ser Pro Tyr Met
        195                 200                 205

Cys Val Gly Met Gly Ile Asp Ala Ile Gln Phe Phe Asp Ser Leu His
    210                 215                 220

Ile Lys Phe Ala His Gln Ser Lys Leu Gly Ile Thr Tyr Pro Leu Ser
225                 230                 235                 240

Ser Asn Val His Leu Phe Ala Asp Ser Tyr Tyr His Lys Val Ile Gly
                245                 250                 255

Asn Lys Phe Lys Asn Leu Arg Val Gln His Val Tyr Glu Leu Gln Gln
            260                 265                 270

Val Pro Lys Val Thr Ser Ala Val Ala Thr Leu Asp Ile Gly Tyr Phe
        275                 280                 285

Gly Gly Glu Val Gly Val Arg Phe Ile Leu
    290                 295

<210> SEQ ID NO 53
<211> LENGTH: 882
<212> TYPE: DNA
<213> ORGANISM: Ehrlichia canis

<400> SEQUENCE: 53
atggcaaatt ttatgtacaa aaaatacaaa ctaatgacag caggtgtagt attatttcac      60
atgttatttc tacctcatgt ttctttcgca aaaaatacaa acagcaataa acttggatta     120
tacatcagtg gacagtataa ccctagtgtt tctgttttta gcaattttte agcaaaagaa     180 accaatgttc atacagtaca actcatggcg cttaaaaaag acattgattc tattgaagtt     240
gatactggaa atagcgcagg tattagcaaa ccacaaaatt tcacagttct ttatactcca     300
aaatttcaag ataatgttgc tggtcttagc ggtgcacttg gattctttta ttctaaagga     360
ttaaggattg aaatgggggt ttcttatgaa aaatttgatg ctaaagacct tggtgagtac     420
accaaaataa aagatgctta gatatttt gctctagtac gtgaaatgca tgttagtctc     480
atttatccaa aagataataa cacaggaaca cattatactg ttatgagaaa tgatggtata     540
tctatttctt ctgctacagt aaatggctgc tatgattctt ttttccagtt tatctttgtc     600

```
acctatatgt gtataggcat cggtatagat gctatagaat ttcttaatgc atacatatta    660
agtttgcttg ccaaggtagt taaggtgtta acttattctg tatctcccaa tgttaattta    720
tttgcagatg gatattatca taaagtgatg ggcaataaat ttaaaaattt acctgttcaa    780
tacgttaata ctttagaaga gtatccaaga gttacatctg caattgctac acttgatatt    840
ggctacctcg gtggtgaaat tggcataaga tttatatttt aa                      882
```

<210> SEQ ID NO 54
<211> LENGTH: 293
<212> TYPE: PRT
<213> ORGANISM: Ehrlichia canis

<400> SEQUENCE: 54

```
Met Ala Asn Phe Met Tyr Lys Lys Tyr Lys Leu Met Thr Ala Gly Val
 1               5                  10                  15

Val Leu Phe His Met Leu Phe Leu Pro His Val Ser Phe Ala Lys Asn
                20                  25                  30

Thr Asn Ser Asn Lys Leu Gly Leu Tyr Ile Ser Gly Gln Tyr Asn Pro
            35                  40                  45

Ser Val Ser Val Phe Ser Asn Phe Ser Ala Lys Glu Thr Asn Val His
        50                  55                  60

Thr Val Gln Leu Met Ala Leu Lys Lys Asp Ile Asp Ser Ile Glu Val
 65                  70                  75                  80

Asp Thr Gly Asn Ser Ala Gly Ile Ser Lys Pro Gln Asn Phe Thr Val
                85                  90                  95

Leu Tyr Thr Pro Lys Phe Gln Asp Asn Val Ala Gly Leu Ser Gly Ala
            100                 105                 110

Leu Gly Phe Phe Tyr Ser Lys Gly Leu Arg Ile Glu Met Gly Phe Ser
        115                 120                 125

Tyr Glu Lys Phe Asp Ala Lys Asp Leu Gly Glu Tyr Thr Lys Ile Lys
    130                 135                 140

Asp Ala Tyr Arg Tyr Phe Ala Leu Val Arg Glu Met His Val Ser Leu
145                 150                 155                 160

Ile Tyr Pro Lys Asp Asn Asn Thr Gly Thr His Tyr Thr Val Met Arg
                165                 170                 175

Asn Asp Gly Ile Ser Ile Ser Ser Ala Thr Val Asn Gly Cys Tyr Asp
            180                 185                 190

Ser Phe Phe Gln Phe Ile Phe Val Thr Tyr Met Cys Ile Gly Ile Gly
        195                 200                 205

Ile Asp Ala Ile Glu Phe Leu Asn Ala Tyr Ile Leu Ser Leu Leu Ala
    210                 215                 220

Lys Val Lys Val Leu Thr Tyr Ser Val Ser Pro Asn Val Asn Leu
225                 230                 235                 240

Phe Ala Asp Gly Tyr Tyr His Lys Val Met Gly Asn Lys Phe Lys Asn
                245                 250                 255

Leu Pro Val Gln Tyr Val Asn Thr Leu Glu Glu Tyr Pro Arg Val Thr
            260                 265                 270

Ser Ala Ile Ala Thr Leu Asp Ile Gly Tyr Leu Gly Gly Glu Ile Gly
        275                 280                 285

Ile Arg Phe Ile Phe
    290
```

<210> SEQ ID NO 55
<211> LENGTH: 891

<212> TYPE: DNA
<213> ORGANISM: Ehrlichia canis

<400> SEQUENCE: 55

```
atgggaaatt ctatgaataa taaaagtcaa ttcttaataa gatttatatt tttaacatgc      60
atgctgtcat tacctaatat atctctttca aaagtaaata cgaaaaaaca ttctggtttg     120
tatattagcg ggcaatacaa acccagtgtt tctgttttca gtaattttc agttaaagaa      180
accaactttc atacaaaaca tctcatagct cttaaacaag atgttgattc tgttgaaatt     240
gatactggta gtaatacagc aggtattagt aacccatcta actttacaat cccttatact     300
gcagaatttc aagacaacca tactaactgc aatggctcta ttggttatgc ttttgctgaa     360
ggtccaagaa ttgaaataga attatcatat gaaaaatttg atgttaaaaa tcccacaggg     420
tatactacag taaaagatgc ttatagatac tttgctttag cacgtgaaat aaatatttct     480
ctattccaac aaaacaaaa agaaggtagt ggaatttacc atgtcgtaat gaaaaacgat      540
gggttatcta tcttatccaa tatagttaat atttgctacg attttctttt aaataattta     600
cctatatcac cttatttatg cggaggaatg ggtataaatg ccatagaatt ctttgacgct     660
ttacatgtga aatttgctta tcaaagcaag gcaggaatta gttatcaact attacgtaaa     720
atcaacttat ttattgatgt atattactac gaagtaataa gtaataaatt taaaaacctg     780
aaagtccaac atgtacatga acttaaagat aatccaaaag tcacatctgc agttgctaca     840
cttgatatag catattttgg tagtgaagct ggcataagaa ttatatttta a               891
```

<210> SEQ ID NO 56
<211> LENGTH: 296
<212> TYPE: PRT
<213> ORGANISM: Ehrlichia canis

<400> SEQUENCE: 56

```
Met Gly Asn Ser Met Asn Asn Lys Ser Gln Phe Leu Ile Arg Phe Ile
  1               5                  10                  15

Phe Leu Thr Cys Met Leu Ser Leu Pro Asn Ile Ser Leu Ser Lys Val
             20                  25                  30

Asn Asn Glu Lys His Ser Gly Leu Tyr Ile Ser Gly Gln Tyr Lys Pro
         35                  40                  45

Ser Val Ser Val Phe Ser Asn Phe Ser Val Lys Glu Thr Asn Phe His
     50                  55                  60

Thr Lys His Leu Ile Ala Leu Lys Gln Asp Val Asp Ser Val Glu Ile
 65                  70                  75                  80

Asp Thr Gly Ser Asn Thr Ala Gly Ile Ser Asn Pro Ser Asn Phe Thr
                 85                  90                  95

Ile Pro Tyr Thr Ala Glu Phe Gln Asp Asn His Thr Asn Cys Asn Gly
            100                 105                 110

Ser Ile Gly Tyr Ala Phe Ala Glu Gly Pro Arg Ile Glu Ile Glu Leu
        115                 120                 125

Ser Tyr Glu Lys Phe Asp Val Lys Asn Pro Thr Gly Tyr Thr Thr Val
    130                 135                 140

Lys Asp Ala Tyr Arg Tyr Phe Ala Leu Ala Arg Glu Ile Asn Ile Ser
145                 150                 155                 160

Leu Phe Gln Pro Lys Gln Lys Glu Gly Ser Gly Ile Tyr His Val Val
                165                 170                 175

Met Lys Asn Asp Gly Leu Ser Ile Leu Ser Asn Ile Val Asn Ile Cys
            180                 185                 190
```

Tyr Asp Phe Ser Leu Asn Asn Leu Pro Ile Ser Pro Tyr Leu Cys Gly
        195                 200                 205

Gly Met Gly Ile Asn Ala Ile Glu Phe Phe Asp Ala Leu His Val Lys
    210                 215                 220

Phe Ala Tyr Gln Ser Lys Ala Gly Ile Ser Tyr Gln Leu Leu Arg Lys
225                 230                 235                 240

Ile Asn Leu Phe Ile Asp Val Tyr Tyr Glu Val Ile Ser Asn Lys
                245                 250                 255

Phe Lys Asn Leu Lys Val Gln His Val His Glu Leu Lys Asp Asn Pro
                260                 265                 270

Lys Val Thr Ser Ala Val Ala Thr Leu Asp Ile Ala Tyr Phe Gly Ser
        275                 280                 285

Glu Ala Gly Ile Arg Ile Ile Phe
        290                 295

<210> SEQ ID NO 57
<211> LENGTH: 846
<212> TYPE: DNA
<213> ORGANISM: Ehrlichia canis

<400> SEQUENCE: 57
atgaataata aaagaaattt ttttttaata ggtatgtctc tattgataaa tctactattg      60
ccaattgatg cctcttctat ggaagtacat aattatacac attttacacc taggctgtat     120
attagtgggc aatacaggcc aggagtttcc cactttagca aattttcagt caaagaaaca     180
cattgtaata ctgtgcaatt agttgggcta acaaaagata taaagtaac taataacagt      240 agtatcaaca caaatactag ttttaacttt ccttatgttg cagaatttca agataacgca     300
atgagcttta gtggagcaat aggatgcttt tattcagaac acttcagaat tgaagtagaa     360
gcttcttatg aagaatttga cgttaaaaat cctgaaggat ctactacaga ctcctataga     420
tatttcgcgt tagcacgtgg catggatggt aataatattc ctacaagtca aaaatttact     480
gtaatgagaa acgacgggtt attaatctca tctgttatga taaatggctg ttacaatgtc     540
atactaaatg atatacaagc agaaccttac atatgtgcag actaggagg agattttata     600 gaattcttca atggctttca tgttaagcta gcttatcaag gtaaagtagg cattagttat     660
caaatattcc ctgaagtaag attatttatt gatggatact accataaagt aaaaggcaac     720
aagtttaaaa atttacacgt tcaacatgta ggtgcacttg cagcactccc taagttaca      780 tctgcagttg caacacttaa tattggatac tttggttgtg aagctggagt aagattcata     840
tttttaa                                                              846

<210> SEQ ID NO 58
<211> LENGTH: 281
<212> TYPE: PRT
<213> ORGANISM: Ehrlichia canis

<400> SEQUENCE: 58

Met Asn Asn Lys Arg Asn Phe Phe Leu Ile Gly Met Ser Leu Leu Ile
1               5                   10                  15

Asn Leu Leu Leu Pro Ile Asp Ala Ser Ser Met Glu Val His Asn Tyr
                20                  25                  30

Thr His Phe Thr Pro Arg Leu Tyr Ile Ser Gly Gln Tyr Arg Pro Gly
            35                  40                  45

Val Ser His Phe Ser Lys Phe Ser Val Lys Glu Thr His Cys Asn Thr
        50                  55                  60

```
Val Gln Leu Val Gly Leu Thr Lys Asp Ile Lys Val Thr Asn Asn Ser
 65                  70                  75                  80

Ser Ile Asn Thr Asn Thr Ser Phe Asn Phe Pro Tyr Val Ala Glu Phe
                 85                  90                  95

Gln Asp Asn Ala Met Ser Phe Ser Gly Ala Ile Gly Cys Phe Tyr Ser
            100                 105                 110

Glu His Phe Arg Ile Glu Val Glu Ala Ser Tyr Glu Glu Phe Asp Val
        115                 120                 125

Lys Asn Pro Glu Gly Ser Thr Thr Asp Ser Tyr Arg Tyr Phe Ala Leu
    130                 135                 140

Ala Arg Gly Met Asp Gly Asn Asn Ile Pro Thr Ser Gln Lys Phe Thr
145                 150                 155                 160

Val Met Arg Asn Asp Gly Leu Leu Ile Ser Ser Val Met Ile Asn Gly
                165                 170                 175

Cys Tyr Asn Val Ile Leu Asn Asp Ile Gln Ala Glu Pro Tyr Ile Cys
            180                 185                 190

Ala Gly Leu Gly Gly Asp Phe Ile Glu Phe Phe Asn Gly Phe His Val
        195                 200                 205

Lys Leu Ala Tyr Gln Gly Lys Val Gly Ile Ser Tyr Gln Ile Phe Pro
    210                 215                 220

Glu Val Arg Leu Phe Ile Asp Gly Tyr Tyr His Lys Val Lys Gly Asn
225                 230                 235                 240

Lys Phe Lys Asn Leu His Val Gln His Val Gly Ala Leu Ala Ala Leu
                245                 250                 255

Pro Lys Val Thr Ser Ala Val Ala Thr Leu Asn Ile Gly Tyr Phe Gly
            260                 265                 270

Cys Glu Ala Gly Val Arg Phe Ile Phe
        275                 280

<210> SEQ ID NO 59
<211> LENGTH: 840
<212> TYPE: DNA
<213> ORGANISM: Ehrlichia canis

<400> SEQUENCE: 59
atgaacaaaa agaaaattat tacagtagga acaacattag cttatttatt attatcacct      60
aacatatctt tttcagaagt aatcaacaat gatactgata atattctag actatatata     120 agtggtcaat ataaccagg  attttcttat tttaataagt tctcagttag agaaactgat     180
catttcacta aagcattaat aggattaaga catgacgcaa tatctactaa aaatttaaca     240
actaatacag atttcaatac tctttataaa gtaacatttc aaaacaacat cattagcttt     300
agcggtgcta ttggttattc tgatagcaca ggtgtaaggt tgagctaga aggctcttat      360 gaagagttcg atgttacaga ccctggagat tgtataataa agatactta caggtacttt     420 gcattagcta gaaaaacaag tggtaatcat cccaacgata tggggaata tactgtcatg     480 agaaatgatg gagtatccat tacctccgtt atattcaatg gttgttatga tctctcttta     540
aaagagctag aaatatcacc atatgtttgc attggtatcg gaggagactt tatagaattt     600
tttgatgctt tacacattaa attagcatat caaggtaaac taggtattag ctattctttt     660
tccactagaa caaattttatt tatcgattgt tattaccata gagttatagg taatcaattt     720
aataatttaa atgttcaaca tgtagttgag cttacagaag cacctaaagc tacatctgca     780
attgctacac ttaatgttag ttacttcggt ggagaagttg gaattagact tatgtttaa      840
```

<210> SEQ ID NO 60
<211> LENGTH: 279
<212> TYPE: PRT
<213> ORGANISM: Ehrlichia canis

<400> SEQUENCE: 60

Met Asn Lys Lys Ile Ile Thr Val Gly Thr Thr Leu Ala Tyr Leu
1               5                   10                  15

Leu Leu Ser Pro Asn Ile Ser Phe Ser Glu Val Ile Asn Asn Asp Thr
            20                  25                  30

Asp Lys Tyr Ser Arg Leu Tyr Ile Ser Gly Gln Tyr Lys Pro Gly Phe
        35                  40                  45

Ser Tyr Phe Asn Lys Phe Ser Val Arg Glu Thr Asp His Phe Thr Lys
    50                  55                  60

Ala Leu Ile Gly Leu Arg His Asp Ala Ile Ser Thr Lys Asn Leu Thr
65                  70                  75                  80

Thr Asn Thr Asp Phe Asn Thr Leu Tyr Lys Val Thr Phe Gln Asn Asn
                85                  90                  95

Ile Ile Ser Phe Ser Gly Ala Ile Gly Tyr Ser Asp Ser Thr Gly Val
            100                 105                 110

Arg Phe Glu Leu Glu Gly Ser Tyr Glu Glu Phe Asp Val Thr Asp Pro
        115                 120                 125

Gly Asp Cys Ile Ile Lys Asp Thr Tyr Arg Tyr Phe Ala Leu Ala Arg
    130                 135                 140

Lys Thr Ser Gly Asn His Pro Asn Asp Asn Gly Glu Tyr Thr Val Met
145                 150                 155                 160

Arg Asn Asp Gly Val Ser Ile Thr Ser Val Ile Phe Asn Gly Cys Tyr
                165                 170                 175

Asp Leu Ser Leu Lys Glu Leu Glu Ile Ser Pro Tyr Val Cys Ile Gly
            180                 185                 190

Ile Gly Gly Asp Phe Ile Glu Phe Phe Asp Ala Leu His Ile Lys Leu
        195                 200                 205

Ala Tyr Gln Gly Lys Leu Gly Ile Ser Tyr Ser Phe Ser Thr Arg Thr
    210                 215                 220

Asn Leu Phe Ile Asp Cys Tyr Tyr His Arg Val Ile Gly Asn Gln Phe
225                 230                 235                 240

Asn Asn Leu Asn Val Gln His Val Val Glu Leu Thr Glu Ala Pro Lys
                245                 250                 255

Ala Thr Ser Ala Ile Ala Thr Leu Asn Val Ser Tyr Phe Gly Gly Glu
            260                 265                 270

Val Gly Ile Arg Leu Met Phe
        275

<210> SEQ ID NO 61
<211> LENGTH: 726
<212> TYPE: DNA
<213> ORGANISM: Ehrlichia canis

<400> SEQUENCE: 61
cccgtcgttt ctcattacag tgactttca attaaagaaa cttatactaa cactgaggca      60
ttgtttgggc taaaacaaga tattagttct attttacgta ataaagagac cacacaatat    120
aataacaatt ttaacgttcc ctatactgca aaatttcaag acgactttgc gagtttcagc    180
atagctgttg gatatattgc taacaatggt ccaagaattg aaatagaagg atcttacgaa    240
gaatttgatg ttaaaaaccc aggaaattat acaacaatag atgctcatag gtacattgct    300

```
ttagctagag aaaaaacttc ttactatcta agttctccta aagaaaacaa atatgtaatt      360
ataaagaata acggcatatc tattgtatct attataatta atggttgtta tgatatttct      420
ttaaatgatt ctaaggtgtc accttacata tgcacagggt ttggtggaga ttttatagag      480 tttttagtg ctatacgttt taagtttgct tatcaaggta aaataggtat cagttattca       540
ttatcttcta acataatttt atttactgat ggatattacc acaaggtaat aaattcccaa      600
tttaaaaatt taaatgttga acatgttgtt aatgagttaa ctacagatcc taaagtgact      660
tctgcaacag catttcttaa tattgagtat tttggtggtg aatttggatt aaaatttata      720
ttttaa                                                                 726
```

<210> SEQ ID NO 62
<211> LENGTH: 241
<212> TYPE: PRT
<213> ORGANISM: Ehrlichia canis

<400> SEQUENCE: 62

```
Pro Val Val Ser His Tyr Ser Asp Phe Ser Ile Lys Glu Thr Tyr Thr
 1               5                  10                  15

Asn Thr Glu Ala Leu Phe Gly Leu Lys Gln Asp Ile Ser Ser Ile Leu
             20                  25                  30

Arg Asn Lys Glu Thr Thr Gln Tyr Asn Asn Asn Phe Asn Val Pro Tyr
         35                  40                  45

Thr Ala Lys Phe Gln Asp Asp Phe Ala Ser Phe Ser Ile Ala Val Gly
     50                  55                  60

Tyr Ile Ala Asn Asn Gly Pro Arg Ile Glu Ile Gly Ser Tyr Glu
 65                  70                  75                  80

Glu Phe Asp Val Lys Asn Pro Gly Asn Tyr Thr Thr Ile Asp Ala His
                 85                  90                  95

Arg Tyr Ile Ala Leu Ala Arg Glu Lys Thr Ser Tyr Tyr Leu Ser Ser
            100                 105                 110

Pro Lys Glu Asn Lys Tyr Val Ile Ile Lys Asn Asn Gly Ile Ser Ile
        115                 120                 125

Val Ser Ile Ile Ile Asn Gly Cys Tyr Asp Ile Ser Leu Asn Asp Ser
130                 135                 140

Lys Val Ser Pro Tyr Ile Cys Thr Gly Phe Gly Gly Asp Phe Ile Glu
145                 150                 155                 160

Phe Phe Ser Ala Ile Arg Phe Lys Phe Ala Tyr Gln Gly Lys Ile Gly
                165                 170                 175

Ile Ser Tyr Ser Leu Ser Ser Asn Ile Ile Leu Phe Thr Asp Gly Tyr
            180                 185                 190

Tyr His Lys Val Ile Asn Ser Gln Phe Lys Asn Leu Asn Val Glu His
        195                 200                 205

Val Val Asn Glu Leu Thr Thr Asp Pro Lys Val Thr Ser Ala Thr Ala
    210                 215                 220

Phe Leu Asn Ile Glu Tyr Phe Gly Gly Glu Phe Gly Leu Lys Phe Ile
225                 230                 235                 240

Phe
```

<210> SEQ ID NO 63
<211> LENGTH: 19
<212> TYPE: PRT
<213> ORGANISM: Ehrlichia chaffeensis

<400> SEQUENCE: 63

-continued

```
Asp Pro Ala Gly Ser Gly Ile Asn Gly Asn Phe Tyr Ile Ser Gly Lys
  1               5                  10                  15

Tyr Met Pro

<210> SEQ ID NO 64
<211> LENGTH: 34
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (17)
<223> OTHER INFORMATION: a, c, g or t
<220> FEATURE:
<221> NAME/KEY: modified_base
<222> LOCATION: (26)
<223> OTHER INFORMATION: a, c, g or t

<400> SEQUENCE: 64
cgggatccga attcggnath aayggnaayt tyta                                   34

<210> SEQ ID NO 65
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 65
agcggccgct taraayasra ayctttsctcc                                       30

<210> SEQ ID NO 66
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 66
acctaacttt ccttggtaag                                                   20

<210> SEQ ID NO 67
<211> LENGTH: 281
<212> TYPE: PRT
<213> ORGANISM: Ehrlichia chaffeensis

<400> SEQUENCE: 67

Met Asn Tyr Lys Lys Val Phe Ile Thr Ser Ala Leu Ile Ser Leu Ile
  1               5                  10                  15

Ser Ser Leu Pro Gly Val Ser Phe Ser Asp Pro Ala Gly Ser Gly Ile
             20                  25                  30

Asn Gly Asn Phe Tyr Ile Ser Gly Lys Tyr Met Pro Ser Ala Ser His
         35                  40                  45

Phe Gly Val Phe Ser Ala Lys Glu Glu Arg Asn Thr Thr Val Gly Val
     50                  55                  60

Phe Gly Leu Lys Gln Asn Trp Asp Gly Ser Ala Ile Ser Asn Ser Ser
 65                  70                  75                  80

Pro Asn Asp Val Phe Thr Val Ser Asn Tyr Ser Phe Lys Tyr Glu Asn
                 85                  90                  95

Asn Pro Phe Leu Gly Phe Ala Gly Ala Ile Gly Tyr Ser Met Asp Gly
```

```
                    100                 105                 110
Pro Arg Ile Glu Leu Glu Val Ser Tyr Glu Thr Phe Asp Val Lys Asn
            115                 120                 125
Gln Gly Asn Asn Tyr Lys Asn Glu Ala His Arg Tyr Cys Ala Leu Ser
        130                 135                 140
His Asn Ser Ala Ala Asp Met Ser Ser Ala Ser Asn Asn Phe Val Phe
145                 150                 155                 160
Leu Lys Asn Glu Gly Leu Leu Asp Ile Ser Phe Met Leu Asn Ala Cys
                165                 170                 175
Tyr Asp Val Val Gly Glu Gly Ile Pro Phe Ser Pro Tyr Ile Cys Ala
            180                 185                 190
Gly Ile Gly Thr Asp Leu Val Ser Met Phe Glu Ala Thr Asn Pro Lys
        195                 200                 205
Ile Ser Tyr Gln Gly Lys Leu Gly Leu Ser Tyr Ser Ile Ser Pro Glu
    210                 215                 220
Ala Ser Val Phe Ile Gly Gly His Phe His Lys Val Leu Gly Asn Glu
225                 230                 235                 240
Phe Arg Asp Ile Pro Thr Ile Ile Pro Thr Gly Ser Thr Leu Ala Gly
                245                 250                 255
Lys Gly Asn Tyr Pro Ala Ile Val Ile Leu Asp Val Cys His Phe Gly
            260                 265                 270
Ile Glu Leu Gly Gly Arg Phe Val Phe
        275                 280

<210> SEQ ID NO 68
<211> LENGTH: 756
<212> TYPE: DNA
<213> ORGANISM: Ehrlichia chaffeensis

<400> SEQUENCE: 68
ggcataaatg ggaatttcta catcagtgga aaatacatgc caagtgcttc gcattttgga      60
gtattctctg ctaaggaaga agaaatacaa acagttggag tgtttggact gaagcaaaat    120
tgggacggaa gcgcaatatc caactcctcc ccaaacgatg tattcactgt ctcaaattat    180
tcatttaaat atgaaaacaa cccgttttta ggttttgcag gagctattgg ttactcaatg    240
gatggtccaa gaatagagct tgaagtatct tatgaaacat tgatgtaaa aaatcaaggt     300
aacaattata gaatgaagc acatagatat tgtgctctat cccataactc agcagcagac    360
atgagtagtg caagtaataa ttttgtcttt ctaaaaaatg aaggattact tgacatatca    420
tttatgctga acgcatgcta tgacgtagta ggcgaaggca tacctttttc tccttatata    480
tgcgcaggta tcggtactga tttagtatcc atgtttgaag ctacaaatcc taaaatttct    540
taccaaggaa agttaggttt aagctactct ataagcccag aagcttctgt gtttattggt    600
gggcactttc ataaggtaat agggaacgaa tttagagata ttcctactat aatacctact    660
ggatcaacac ttgcaggaaa aggaaactac cctgcaatag taatactgga tgtatgccac    720
tttggaatag aacttggagg aaggtttgct ttctaa                             756

<210> SEQ ID NO 69
<211> LENGTH: 283
<212> TYPE: PRT
<213> ORGANISM: Cowdria ruminantium

<400> SEQUENCE: 69

Met Asn Cys Lys Lys Ile Phe Ile Thr Ser Thr Leu Ile Ser Leu Val
1               5                   10                  15
```

-continued

```
Ser Phe Leu Pro Gly Val Ser Phe Ser Asp Val Ile Gln Glu Glu Asn
            20                  25                  30

Asn Pro Val Gly Ser Val Tyr Ile Ser Ala Lys Tyr Met Pro Thr Ala
        35                  40                  45

Ser His Phe Gly Lys Met Ser Ile Lys Glu Asp Ser Arg Asp Thr Lys
    50                  55                  60

Ala Val Phe Gly Leu Lys Lys Asp Trp Asp Gly Val Lys Thr Pro Ser
65                  70                  75                  80

Gly Asn Thr Asn Ser Ile Phe Thr Glu Lys Asp Tyr Ser Phe Lys Tyr
                85                  90                  95

Glu Asn Asn Pro Phe Leu Gly Phe Ala Gly Ala Val Gly Tyr Ser Met
            100                 105                 110

Asn Gly Pro Arg Ile Glu Phe Glu Val Ser Tyr Glu Thr Phe Asp Val
            115                 120                 125

Arg Asn Pro Gly Gly Asn Tyr Lys Asn Asp Ala His Met Tyr Cys Ala
        130                 135                 140

Leu Asp Thr Ala Ser Ser Thr Ala Gly Ala Thr Thr Ser Val Met
145                 150                 155                 160

Val Lys Asn Glu Asn Leu Thr Asp Ile Ser Leu Met Leu Asn Ala Cys
                165                 170                 175

Tyr Asp Ile Met Leu Asp Gly Met Pro Val Ser Pro Tyr Val Cys Ala
            180                 185                 190

Gly Ile Gly Thr Asp Leu Val Ser Val Ile Asn Ala Thr Asn Pro Lys
            195                 200                 205

Leu Ser Tyr Gln Gly Lys Leu Gly Ile Ser Tyr Ser Ile Asn Pro Glu
    210                 215                 220

Ala Ser Ile Phe Ile Gly Gly His Phe His Arg Val Ile Gly Asn Glu
225                 230                 235                 240

Phe Lys Asp Ile Ala Thr Ser Lys Val Phe Thr Ser Ser Gly Asn Ala
            245                 250                 255

Ser Ser Ala Val Ser Pro Gly Phe Ala Ser Ala Ile Leu Asp Val Cys
            260                 265                 270

His Phe Gly Ile Glu Ile Gly Arg Phe Val Phe
    275                 280
```

OUTER MEMBRANE PROTEIN OF *EHRLICHIA CANIS* AND *EHRLICHIA CHAFFEENSIS*

This application is a divisional of U.S. application Ser. No. 10/314,639, filed Dec. 9, 2002, now U.S. Pat. No. 6,893,640, which is a divisional of U.S. application Ser. No. 09/314,701, filed on May 19, 1999, and issued Apr. 8, 2003 as U.S. Pat. No. 6,544,517, which further claims priority from U.S. Provisional Application No. 60/100,843, filed on Sep. 18, 1998. The disclosures of each of these applications is incorporated herein by reference.

This work was supported by grant RO1 AI33123 and RO1 AI40934 from National Institutes of Health. The government has certain rights in this invention.

BACKGROUND OF THE INVENTION

The ehrlichiae are obligate intracellular bacteria that infect circulating leucocytes. *Ehrlichia chaffeensis* infects the monocytes and macrophages in humans and causes human monocytic ehrlichiosis. The clinical manifestations of ehrlichiosis in humans are nonspecific and similar to Rocky Mountain spotted fever. The clinical manifestations include fever, chills, headache, myalgia or vomiting, and weight loss. Most patients have a history of tick exposure.

*Ehrlichia canis* infects and causes ehrlichiosis in animals belonging to the family Canidae. Canine ehrlichiosis consists of an acute and a chronic phase. The acute phase is characterized by fever, serous nasal and ocular discharges, anorexia, depression, and loss of weight. The chronic phase is characterized by severe pancytopenia, epistaxis, hematuria, blood in feces in addition to more severe clinical signs of the acute disease. If treated early during the course of the disease, dogs respond well to doxycycline. However, chronically infected dogs do not respond well to the antibiotic. Therefore, early diagnosis is very important for treating canine ehrlichiosis.

The primary diagnostic test for diagnosing canine ehrlichiosis and human ehrlichiosis is the indirect fluorescent antibody (IFA) test. This test uses the etiologic agent *Ehrlichia canis* to diagnose canine ehrlichiosis. The IFA test uses *Ehrlichia chaffeensis* as antigen for diagnosing human ehrlichiosis. The IFA test has, however, serious limitations. The IFA test is subject to false positives because the antigens are made of whole infected cells which comprise many nonspecific proteins which will cross-react with sera from some patients. The IFA test is also subject to false negatives because IFA antigens are unstable and may become inactivated during storage. In addition the IFA test requires a special equipment to perform the test. For example, the IFA test requires a tissue culture system for growing the bacterium that are used to prepare the antigen slides, a fluorescent microscope, and trained persons to evaluate the serum reactivity to the bacterial antigen on the slide.

Tools which permit simpler, more rapid, and objective serodiagnosis of canine ehrlichiosis or human ehrlichiosis are desirable.

SUMMARY OF THE INVENTION

The present invention relates to improved diagnostic tools for veterinary and human use which are used for serodiagnosing ehrlichiosis in mammals, particularly in members of the Canidae family and in humans. The diagnostic tools are a group of outer membrane proteins of *E. chaffeensis* and variants thereof, referred to hereinafter as the "OMP proteins", a group of outer membrane proteins of *E. canis* and variants thereof referred to hereinafter as the "P30F proteins", and antibodies to the OMP proteins and the P30F proteins.

The OMP proteins of *E. chaffeensis* encompass OMP-1, OMP-1A, OMP1-B, OMP-1C, OMP1-D, OMP1-E, OMP1-F, OMP1-H, OMP-1R, OMP-1S, OMP-1T, OMP-1U, OMP-1V, OMP-1W, OMP-1X, OMP-1Y and OMP-1Z. The mature OMP-1 protein of *E. chaffeensis* has a molecular weight of about 27.7 kDa and comprises amino acid 26 through amino acid 281 of the sequence shown in FIG. 3B, SEQ ID NO: 2. The mature OMP-1B protein of *E. chaffeensis* has a molecular weight of about 28.2 kDa and comprises amino acid 26 through amino acid 283 of the sequence shown in FIG. 4B, SEQ ID NO: 4. The mature OMP-1C protein of *E. chaffeensis* has a molecular weight of about 27.6 kDa and comprises amino acid 26 through amino acid 280 of the sequence shown in FIG. 5B, SEQ ID NO: 6. The mature OMP-1D protein of *E. chaffeensis* has a molecular weight of about 28.7 and comprises amino acid 26 through amino acid 286 of the sequence shown in FIG. 6B, SEQ ID NO: 8. The mature OMP-1E protein of *E. chaffeensis* has a molecular weight of about 27.8 kDa and comprises amino acid 26 through amino acid 278 of the sequence shown in FIG. 7B, SEQ ID NO: 10. The mature OMP-1F protein of *E. chaffeensis* has a molecular weight of about 27.9 kDa and comprises amino acid 26 through amino acid 280 of the sequence shown in FIG. 8B, SEQ ID NO: 12. The mature OMP-LA protein of *E. chaffeensis* has a molecular weight of about 29.6 kDa and comprises amino acid 31 through amino acid 297 of the sequence shown in FIG. 9B, SEQ ID NO: 14. The mature OMP-IR protein of *E. chaffeensis* has a molecular weight of about 19.7 kDa and comprises amino acid 29 through amino acid 196 of the sequence shown in FIG. 10B, SEQ ID NO: 16. The mature OMP-1S protein of *E. chaffeensis* has a molecular weight of about 29.2 kDa and comprises amino acid 26 through amino acid 291 of the sequence shown in FIG. 11B, SEQ ID NO: 18. The OMP-1T protein of *E. chaffeensis* comprises the amino acid sequence shown in FIG. 12B, SEQ ID NO: 20. The mature OMP-1U protein of *E. chaffeensis* has a molecular weight of about 30.6 kDa and comprises amino acid 26 through amino acid 295 of the sequence shown in FIG. 13B, SEQ ID NO: 22. The mature OMP-1V protein of *E. chaffeensis* has a molecular weight of about 28.0 kD and comprises amino acid 27 through amino acid 279 shown in FIG. 14B, SEQ ID NO: 24. The mature OMP-1W protein of *E. chaffeensis* has a molecular weight of about 28.8 kDa and comprises amino acid 30 through amino acid 283 of the sequence shown in FIG. 15B, SEQ ID NO: 26. The mature OMP-1X protein of *E. chaffeensis* has a molecular weight of about 27.8 kDa and comprises amino acid 25 through amino acid 275 of the sequence shown in FIG. 16B, SEQ ID NO: 28. The mature OMP-1Y protein of *E. chaffeensis* has a molecular weight about 28.8 kDa and comprises amino acid 28 through amino acid 285 of the sequence shown in FIG. 17B, SEQ ID. NO: 30. The mature OMP-1Z protein of *E. chaffeensis* has a molecular weight of about 30.2 kDa and comprises amino acid 27 through amino acid 300 of the sequence shown in FIG. 18B, SEQ ID NO: 50. The mature OMP-1H protein has a molecular weight of about 30.2 kDa and comprises the amino acid 27 through amino acid 298 of sequence shown in FIG. 33B, SEQ ID NO: 52.

The outer membrane proteins from *E. chaffeensis*, particularly a recombinant form of OMP-1, are immunogenic and, thus are useful for preparing antibodies. Such antibodies are useful for immunolabeling isolates of *E. chaffeensis* and for detecting the presence of *E. chaffeensis* in body fluids, tissues, and particularly in monocytes and macrophages. The OMP proteins, particularly OMP-1, are also useful for detecting antibodies to *E. chaffeensis* in the blood of patients with clinical signs of ehrlichiosis. The OMP protein, particularly OMP-1, are also useful immunogens for raising antibodies that are capable of reducing the level of infection in an immunized mammal that has been infected with *E. chaffeensis*. The proteins are also useful in a vaccine for protecting against infection with *E. chaffeensis*.

The P30F proteins of *E. canis* encompass P30, P30a, P30-1, P30-2, P30-3, P304, P30-5, P30-6, P30-7, P30-8, P30-9, P30-10, P30-1 1, and P30-12. The mature P30 protein of *E. canis* has a molecular weight of about 28.8 kDa and comprises amino acid 26 through amino acid 288 of the sequence shown in FIG. 19B, SEQ ID NO: 32. The mature P30a protein of *E. canis* has a molecular weight of about 29.0 kDa and comprises amino acid 26 through amino acid 287 of the sequence shown in FIG. 20B, SEQ ID NO: 34. The mature P30-1 protein of *E. canis* has a molecular weight of about 27.7 kDa and comprises amino acid 55 through amino acid 307 of the sequence shown in FIG. 21B, SEQ ID NO: 36. The mature P30-2 protein of *E. canis* has a molecular weight of about 28.0 kDa and comprises amino acid 26 through amino acid 280 of the sequence shown in FIG. 22B, SEQ ID NO: 38. The mature P30-3 protein of *E. canis* has a molecular weight of about 28.7 kDa and comprises amino acid 26 through amino acid 283 of the sequence shown in FIG. 23B, SEQ ID NO: 40. The mature P30-4 protein of *E. canis* has a molecular weight of about 28.0 kDa and comprises amino acid 26 through amino acid 276 of the sequence shown in FIG. 24B, SEQ ID NO: 42. The mature P30-5 protein of *E. canis* has a molecular weight of about 29.4 kDa and comprises amino acid 27 through amino acid 293 of the sequence shown in FIG. 25B, SEQ ID NO: 44. The mature P30-6 protein of *E. canis* has a molecular weight of about 29.4 kDa and comprises amino acid 31 through amino acid 293 of the sequence shown in FIG. 26B, SEQ ID NO: 54. The mature P30-7 protein of *E. canis* has a molecular weight of about 29.9 kDa and comprises amino acid 31 through amino acid 296 of the sequence shown in FIG. 27B, SEQ ID NO: 56. The mature P30-8 protein of *E. canis* has a molecular weight of about 30.3 kDa and comprises amino acid 27 through amino acid 299 of the sequence shown in FIG. 28B, SEQ ID NO: 46. The mature P30-9 protein of *E. canis* has a molecular weight of about 28.6 kDa and comprises amino acid 27 through amino acid 281 of the sequence shown in FIG. 29B, SEQ ID NO: 58. The mature P30-10 protein of *E. canis* has a molecular weight of about 28.1 kDa and comprises amino acid 26 through amino acid 280 of the sequence shown in FIG. 30B, SEQ ID NO: 48. The mature P30-11 protein of *E. canis* has a molecular weight of about 28.6 kDa and comprises the amino acid 26 through amino acid 279 of sequence shown in FIG. 31B, SEQ ID NO: 60. The P30-12 protein of *E. canis* has a molecular weight of at least 27.3 kDa and comprises the amino acid sequence shown in FIG. 32B, SEQ ID NO: 62.

The P30F proteins, particularly P30, are immunogenic and are, thus, useful for preparing antibodies that are useful for immunolabeling isolates of *E. canis*. The P30 protein is also useful for diagnosing canine ehrlichiosis in mammals, particularly in members of the family Canidae, most particularly in dogs and for diagnosing infections with *E. chaffeensis* in humans. The P30F proteins are also useful immunogens for raising antibodies that reduce the level of infection in an immunized mammal that has been infected with *E. canis*. The P30F protein are also useful in a vaccine for protecting animals against infection with *E. canis*.

The present invention also provides isolated polynucleotides that encode the *E. chaffeensis* OMP proteins and isolated polynucleotides that encode the *E. canis* P30F proteins. The present invention also relates to antibodies which are immunospecific for and bind to the OMP proteins and the P30F proteins. Such antibodies are useful for immunolabeling isolates of *E. chaffeensis* and *E. canis*. The present invention also relates to Icits containing reagents for diagnosing human ehrlichiosis and canine ehrlichiosis and to immunogenic compositions containing one or more OMP proteins or P30F proteins.

BRIEF DESCRIPTION OF THE FIGURES

FIG. 1. shows the DNA sequence (SEQ ID NO: 68) and the amino acid sequence (residues 26-281 of SEQ ID NO: 2) encoded by the *E. chaffeensis* (p28) gene cloned in pCRIIp28. The N-terminal amino acid sequence of native OMP-1 protein (P28) determined chemically is underlined. Five amino acid residues at the N terminus of P28 which were not included in the p28 gene, are indicated by boldface. Arrows indicate annealing positions of the primer pair designed for PCR.

FIG. 2. shows the restriction map of 6.3-kb genomic DNA including the omp-1 gene copies in *E. chaffeensis*. The four DNA fragments were cloned from the genomic DNA (pPS2.6, pPS3.6, pEC2.6, and pEC3.6). A recombinant plasmid pPS2.6 has an overlapping sequence with that of pEC3.6. The closed boxes at the bottom show PCR-amplified fragments from the genomic DNA for confirmation of the overlapping area. Open boxes at the top indicate open reading frames (ORF) of omp-1 gene copies with direction by arrows. Open boxes at the bottom show DNA fragments subcloned for DNA sequencing.

FIG. 3B shows one embodiment of the OMP-1 protein (SEQ ID NO: 2); FIG. 3A shows one embodiment of the OMP-1 polynucleotide (SEQ ID NO: 1).

FIG. 4B shows one embodiment of the OMP-1B protein (SEQ ID NO: 4); FIG. 4A shows one embodiment of the OMP-1B polynucleotide (SEQ ID NO: 3).

FIG. 5A shows one embodiment of the OMP-1C polynucleotide (SEQ ID NO: 5); FIG. 5B shows one embodiment of the OMP-1C protein (SEQ ID NO: 6).

FIG. 6B shows one embodiment of the OMP-1D protein (SEQ ID NO: 8); FIG. 6A shows one embodiment of the OMP-1D polynucleotide (SEQ ID NO: 7).

FIG. 7B shows one embodiment of the OMP-1E protein (SEQ ID NO: 10); FIG. 7A shows one embodiment of the OMP-1E polynucleotide (SEQ ID NO: 9).

FIG. 8B shows one embodiment of the OMP-1F protein (SEQ ID NO: 12); FIG. 8A shows one embodiment of the OMP-1F polynucleotide (SEQ ID NO: 11).

FIG. 9B shows one embodiment of the OMP-1A protein (SEQ ID NO: 14); FIG. 9A shows one embodiment of the OMP-1A polynucleotide (SEQ ID NO: 13).

FIG. 10B shows one embodiment of a portion of the OMP-1R protein (SEQ ID NO: 16); FIG. 10A shows one embodiment of an OMP-1R polynucleotide (SEQ ID NO: 15) encoding such polypeptide.

FIG. 11B shows one embodiment of a portion of the OMP-1S protein (SEQ ID NO: 18); FIG. 11A shows one embodiment of the OMP-1S polynucleotide (SEQ ID NO: 17) encoding such polypeptide.

FIG. 12B shows one embodiment of a portion of the OMP-1T protein (SEQ ID NO: 20); FIG. 12A shows one embodiment of the OMP-1T polynucleotide (SEQ ID NO: 19) encoding such polypeptide.

FIG. 13B shows one embodiment of the OMP-1U protein (SEQ ID NO: 22); FIG. 13A shows one embodiment of the OMP-1U polynucleotide (SEQ ID NO:21).

FIG. 14B shows one embodiment of the OMP-1V protein (SEQ ID NO: 24); FIG. 14A shows one embodiment of the OMP-1V polynucleotide (SEQ ID NO: 23).

FIG. 15B shows one embodiment of the OMP-1W protein (SEQ ID NO: 26); FIG. 15A shows one embodiment of the OMP-1W polynucleotide (SEQ ID NO: 25).

FIG. 16B shows one embodiment of the OMP-1X protein (SEQ ID NO: 28); FIG. 16A shows one embodiment of the OMP-1X polynucleotide (SEQ ID NO: 27).

FIG. 17B shows one embodiment of the OMP-1Y protein (SEQ ID NO: 30); FIG. 17A shows one embodiment of the OMP-1Y polynucleotide (SEQ ID NO: 29).

FIG. 18B shows one embodiment of the OMP-1Z protein (SEQ ID NO: 50); FIG. 18A shows one embodiment of the OMP-1Z polynucleotide (SEQ ID NO: 49).

FIG. 19B shows one embodiment of the P30 protein (SEQ ID NO: 32); FIG. 19A shows one embodiment of the P30 polynucleotide (SEQ ID NO: 31).

FIG. 20B shows one embodiment of the P30a protein (SEQ ID NO: 34); FIG. 20A shows one embodiment of the p30a polynucleotide (SEQ ID NO: 33).

FIG. 21B shows one embodiment of the P30-1 protein (SEQ ID NO: 36); FIG. 21A shows one embodiment of the p30-11 polynucleotide (SEQ ID NO: 35).

FIG. 22B shows one embodiment of the P30-2 protein (SEQ ID NO: 38); FIG. 22A shows one embodiment of the p30-12 polynucleotide (SEQ ID NO: 37).

FIG. 23B shows one embodiment of the P30-3 protein (SEQ ID NO: 40); FIG. 23A shows one embodiment of the p30-3 polynucleotide (SEQ ID NO: 39).

FIG. 24B shows one embodiment of the P30-4 protein (SEQ ID NO: 42); FIG. 24A shows one embodiment of the p30-4 polynucleotide (SEQ ID NO: 41).

FIG. 25B shows one embodiment of the P30-5 protein (SEQ ID NO: 44); FIG. 25A shows one embodiment of the p30-5 polynucleotide (SEQ ID NO: 43).

FIG. 26B shows one embodiment of the P30-6 protein (SEQ ID NO: 54); FIG. 26A shows one embodiment of the p30-6 polynucleotide (SEQ ID NO: 53).

FIG. 27B shows one embodiment of the P30-7 protein (SEQ ID NO: 56); FIG. 27A shows one embodiment of the p30-7 polynucleotide (SEQ ID NO: 55).

FIG. 28B shows one embodiment of the P30-8 protein (SEQ ID NO: 46); FIG. 28A shows one embodiment of the p30-8 polynucleotide (SEQ ID NO: 45).

FIG. 29B shows one embodiment of a portion of the P30-9 protein (SEQ ID NO: 58); FIG. 29A shows one embodiment of the p30-9 polynucleotide (SEQ ID NO: 57).

FIG. 30B shows one embodiment of a portion of the P30-10 protein (SEQ ID NO: 48); FIG. 30A shows one embodiment of the p30-10 polynucleotide (SEQ ID NO: 47) encoding such protein.

FIG. 31B shows one embodiment of a portion of the P30-11 protein (SEQ ID NO: 60); FIG. 31 A shows one embodiment of the p30-11 polynucleotide (SEQ ID NO: 59).

FIG. 32B shows one embodiment of a portion of the P30-12 protein (SEQ ID NO: 62); FIG. 32A shows one embodiment of the p30-12 polynucleotide (SEQ ID NO: 61).

FIG. 33B shows one embodiment of a portion of the OMP-1H protein (SEQ ID NO: 52) FIG. 33A shows one embodiment of the OMP-1H polynucleotide (SEQ ID NO: 51).

Figure 1:
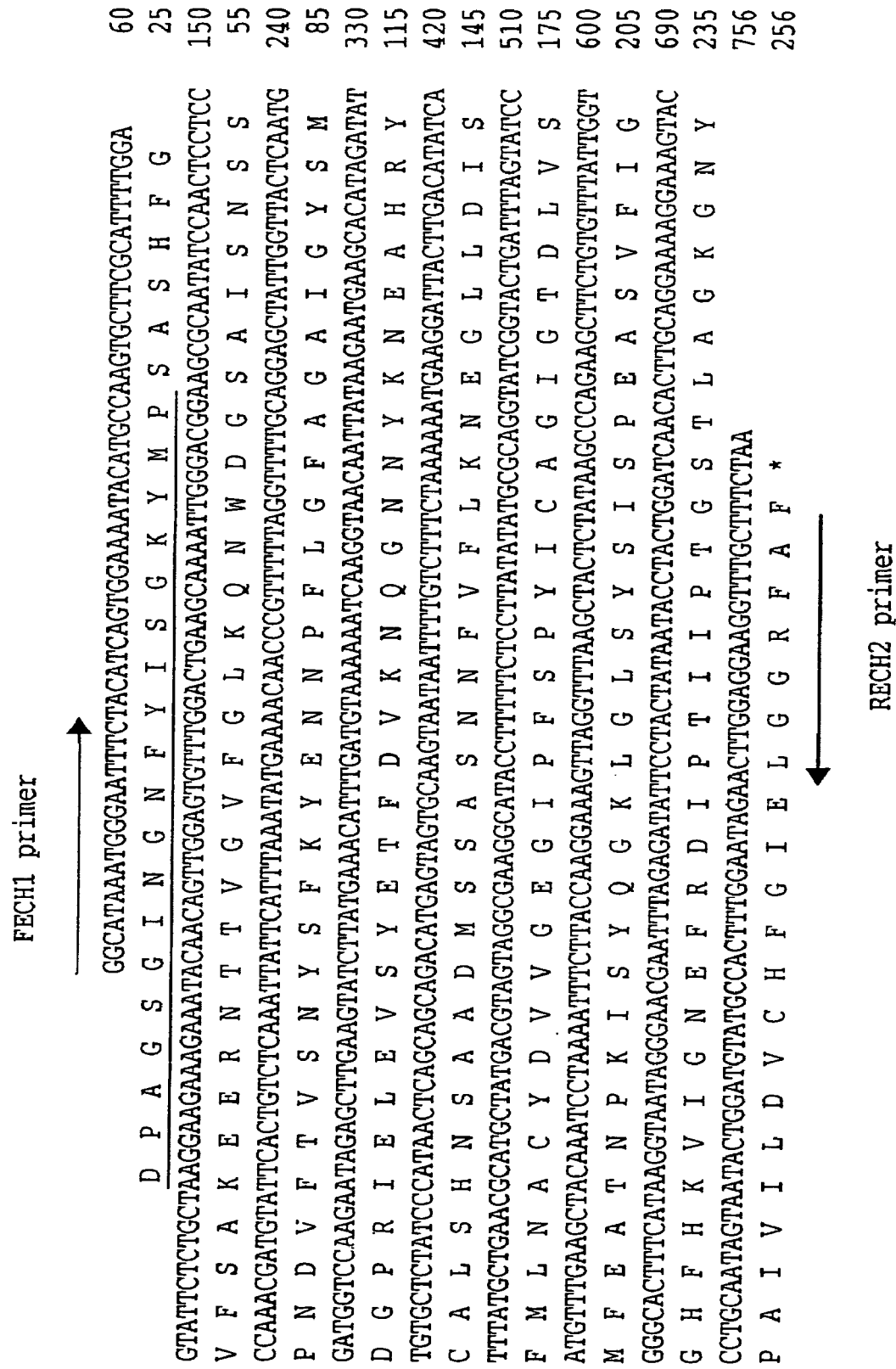

FIG. 34 depicts the amino acid sequences alignment of six *E. chaffeensis* OMP-1s (SEQ ID NOS 12, 10, 8, 6, 4, and residues 26-281 of SEQ ID NO: 2, respectively in order of appearance) and *Cowdria ruminantium* MAP-1 (SEQ ID NO: 69). Aligned positions of identical amino acids with OMP-1F are shown with dots. The sequence of *C. ruminantium* MAP-1 is from the report of Van Vliet et al (1994) Molecular cloning, sequence analysis, and expression of the gene encoding the immunodominant 32-kilodalton protein of *Cowdria ruminantium*. Infect. Immun. 62:1451-1456. Gaps indicated by dashes were introduced for optimal alignment of all proteins. Bars indicate semivariable region (SV) and three hypervariable regions (HV1, HV2, and HV3).

DETAILED DESCRIPTION OF THE INVENTION

The present invention provides a group of outer membrane proteins of *E. chaffeensis*, OMP proteins, and a group of outer membrane proteins of *E. canis*, the P30F proteins. The mature OMP-1 protein of *E. chaffeensis* has a molecular weight of about 27.7 kDa and comprises amino acid 26 through amino acid 281 of the sequence shown in FIG. 3B, SEQ ID NO: 2. The mature OMP-1B protein of *E. chaffeensis* has a molecular weight of about 28.2 kDa and comprises amino acid 26 through amino acid 283 of the sequence shown in FIG. 4B, SEQ ID NO: 4. The mature OMP-1C protein of *E. chaffeensis* has a molecular weight of about 27.6 kDa and comprises amino acid 26 through amino acid 280 of the sequence shown in FIG. 5B, SEQ ID NO: 6. The mature OMP-1D protein of *E. chaffeensis* has a molecular weight of about 28.7 and comprises amino acid 26 through amino acid 286 of the sequence shown in FIG. 6B, SEQ ID NO: 8. The mature OMP-1E protein of *E. chaffeensis* has a molecular weight of about 27.8 kDa and comprises amino acid 26 through amino acid 278 of the sequence shown in FIG. 7B, SEQ ID NO: 10. The mature OMP-1F protein of *E. chaffeensis* has a molecular weight of about 27.9 kDa and comprises amino acid 26 through amino acid 280 of the sequence shown in FIG. 8B, SEQ ID NO: 12. The mature OMP-1 A protein of *E. chaffeensis* has a molecular weight of about 29.6 kDa and comprises amino acid 31 through amino acid 279 of the sequence shown in FIG. 9B, SEQ ID NO: 14. The mature OMP-1R protein of *E. chaffeensis* has a molecular weight of about 19.7 kDa and comprises the amino acid 29 through amino acid 196 of the sequence shown in FIG. 10B, SEQ ID NO: 16. The mature OMP-1S protein of *E. chaffeensis* has a molecular weight of about 29.2 kDa and comprises amino acid 26 through amino acid 291 of the sequence shown in FIG. 11B, SEQ ID NO: 18. The OMP-1T protein of *E. chaffeensis* comprises the amino acid sequence shown in FIG. 12B, SEQ ID NO: 20. The mature OMP-1U protein of *E. chaffeensis* has a molecular weight of about 30.6 kDa and comprises amino acid 26 through amino acid 295 of the sequence shown in FIG. 13B, SEQ ID NO: 22. The mature OMP-1V protein of *E. chaffeensis* has a molecular weight of about 28.0 kD and comprises amino acid 27 through amino acid 279 shown in FIG. 14B, SEQ ID NO: 24. The mature OMP-1W protein of *E. chaffeensis* has a molecular weight of about 28.8 kDa and comprises amino acid 30 through amino acid 283 of the sequence shown in FIG. 15B, SEQ ID NO: 26. The mature OMP-1X protein of *E. chaffeensis* has a molecular weight of about 27.8 kDa and comprises amino acid 25 through amino acid 275 of the sequence shown in FIG. 16B, SEQ ID NO: 28. The mature OMP-1Y protein of *E. chaffeensis* has a molecular weight about 28.8 kDa and comprises amino acid 28 through amino acid 285 of the sequence shown in FIG. 17B, SEQ ID NO: 30. The mature OMP-1Z protein of *E. chaffeensis* has a molecular weight of about 30.2 kDa and comprises amino acid 27 through amino acid 300 of the sequence shown in FIG. 18B, SEQ ID NO: 50. The mature OMP-1H protein has a molecular weight of about 30.2 kDa and comprises the amino acid 27 through amino acid 298 of sequence shown in FIG. 33B, SEQ ID NO: 52.

The mature P30 protein of *E. canis* has a molecular weight of about 28.8 kDa and comprises amino acid 26 through amino acid 288 of the sequence shown in FIG. 19B, SEQ ID NO: 32. The mature P30a protein of *E. canis* has a molecular weight of about 29.0 kDa and comprises amino acid 26 through amino acid 287 of the sequence shown in FIG. 20B, SEQ ID NO: 34. The mature P30-1 protein of *E. canis* has a molecular weight of about 27.7 kDa and comprises amino acid 55 through amino acid 307 of the sequence shown in FIG. 21B, SEQ ID NO: 36. The mature P30-2 protein of *E. canis* has a molecular weight of about 28.0 kDa and comprises amino acid 26 through amino acid 280 of the sequence shown in FIG. 22B, SEQ ID NO: 38. The mature P30-3 protein of *E. canis* has a molecular weight of about 28.7 kDa and comprises amino acid 26 through amino acid 283 of the sequence shown in FIG. 23B, SEQ ID NO: 40. The mature P30-4 protein of *E. canis* has a molecular weight of about 28.0 kDa and comprises amino acid 26 through amino acid 276 of the sequence shown in FIG. 24B, SEQ ID NO: 42. The mature P30-5 protein of *E. canis* has a molecular weight of about 29.4 kDa and comprises amino acid 27 through amino acid 293 of the sequence shown in FIG. 25B, SEQ ID NO: 44. The mature P30-6 protein of *E. canis* has a molecular weight of about 29.4 kDa and comprises amino acid 31 through amino acid 293 of the sequence shown in FIG. 26B, SEQ ID NO: 54. The mature P30-7 protein of *E. canis* has a molecular weight of about 29.9 kDa and comprises amino acid 31 through amino acid 296 of the sequence shown in FIG. 27B, SEQ ID NO: 56. The mature P30-8 protein of *E. canis* has a molecular weight of about 30.3 kDa and comprises amino acid 27 through amino acid 299 of the sequence shown in FIG. 28B, SEQ ID NO: 46. The mature P30-9 protein of *E. canis* has a molecular weight of about 28.6 kDa and comprises amino acid 27 through amino acid 281 of the sequence shown in FIG. 29B, SEQ ID NO: 58. The mature P30-10 protein of *E. canis* has a molecular weight of about 28.1 kDa and comprises amino acid 26 through amino acid 280 of the sequence shown in FIG. 30B, SEQ ID NO: 48. The mature P30-11 protein of *E. canis* has a molecular weight of about 28.6 kDa and comprises the amino acid 26 through amino acid 279 of sequence shown in FIG. 31B, SEQ ID NO: 60. The P30-12 protein of *E. canis* has a molecular weight of at least 27.3 kDa and comprises the amino acid sequence shown in FIG. 32B, SEQ ID NO: 62.

The present invention also encompasses variants of the OMP proteins shown in FIGS. 3-18 and 33 and variants of the P30F proteins shown in FIGS. 19-32. A "variant" as used herein, refers to a protein whose amino acid sequence is similar to one of the amino acid sequences shown in FIGS. 3-33, hereinafter referred to as the reference amino acid sequence, but does not have 100% identity with the respective reference sequence. The variant protein has an altered sequence in which one or more of the amino acids in the reference sequence is deleted or substituted, or one or more amino acids are inserted into the sequence of the reference amino acid sequence. As a result of the alterations, the variant protein has an amino acid sequence which is at least 95% identical to the reference sequence, preferably, at least 97% identical, more preferably at least 98% identical, most preferably at least 99% identical to the reference sequence. Variant sequences which are at least 95% identical have no more than 5 alterations, i.e. any combination of deletions, insertions or substitutions, per 100 amino acids of the reference sequence. Percent identity is determined by comparing the amino acid sequence of the variant with the reference sequence using MEGALIGN project in the DNA STAR program. Sequences are aligned for identity calculations using the method of the software basic local alignment search tool in the BLAST network service (the National Center for Biotechnology Information, Bethesda, Md.) which employs the method of Altschul, S. F., Gish, W., Miller, W., Myers, E. W. & Lipman, D. J. (1990) J. Mol. Biol. 215, 403-410. Identities are calculated by the Align program (DNAstar, Inc.) In all cases, internal gaps and amino acid insertions in the candidate sequence as aligned are not ignored when making the identity calculation.

While it is possible to have nonconservative amino acid substitutions, it is preferred that the substitutions be conservative amino acid substitutions, in which the substituted amino acid has similar structural or chemical properties with the corresponding amino acid in the reference sequence. By way of example, conservative amino acid substitutions involve substitution of one aliphatic or hydrophobic amino acids, e.g. alanine, valine, leucine and isoleucine, with another; substitution of one hydroxyl-containing amino acid, e.g. serine and threonine, with another; substitution of one acidic residue, e.g. glutamic acid or aspartic acid, with another; replacement of one amide-containing residue, e.g. asparagine and glutamine, with another; replacement of one aromatic residue, e.g. phenylalanine and tyrosine, with another; replacement of one basic residue, e.g. lysine, arginine and histidine, with another; and replacement of one small amino acid, e.g., alanine, serine, threonine, methionine, and glycine, with another.

The alterations are designed not to abolish the immunoreactivity of the variant protein with antibodies that bind to the reference protein. Guidance in determining which amino acid residues may be substituted, inserted or deleted without abolishing such immunoreactivity of the variant protein are found using computer programs well known in the art, for example, DNASTAR software. A variant of the OMP-1 protein is set forth in SEQ ID NO: 67 where the alanine at position 280 is replaced with a valine.

The present invention also encompasses fusion proteins in which a tag or one or more amino acids, preferably from about 2 to 65 amino acids, more preferably from about 34 to about 62 amino acids are added to the amino or carboxy terminus of the amino acid sequence of an OMP protein, a P30F protein, or a variant of such protein. Typically, such additions are made to stabilize the resulting fusion protein or to simplify purification of an expressed recombinant form of the corresponding OMP protein, P30F protein or variant of such protein. Such tags are known in the art. Representative examples of such tags include sequences which encode a series of histidine residues, the Herpes simplex glycoprotein D, or glutathione S-transferase.

The present invention also encompasses OMP proteins and P30F proteins in which one or more amino acids, preferably no more than 10 amino acids, in the respective OMP protein or P30F are altered by posttranslation processes or synthetic methods. Examples of such modifications include, but are not limited to, acetylation, amidation, ADP-ribosylation, covalent attachment of flavin, covalent attachment of a heme moiety, covalent attachment of a nucleotide or a lipid, cross-linking ganma-carboxylation, glycosylation, hydroxylation, iodination, methylation, myristoylation, oxidation, pegylation, proteolytic processing, phosphorylation, prenylation, racemization, sulfation, and transfer-RNA mediated additions of amino acids to proteins such as arginylation and ubiquitination.

The OMP proteins, particularly a recombinant form of OMP-1, are immunogenic and, thus are useful for preparing antibodies. Such antibodies are useful for immunolabeling isolates of *E. chaffeensis* and for detecting the presence of *E. chaffeensis* in body fluids, tissues, and particularly in monocytes and macrophages. The OMP proteins, particularly OMP-1, are also useful for detecting antibodies to *E. chaffeensis* in the blood of patients with clinical signs of ehrlichiosis. The OMP proteins, particularly OMP-1, are also useful immunogens for raising antibodies that are capable of reducing the level of infection in an immunized mammal that has been infected with *E. chaffeensis*. The OMP proteins are also useful in a vaccine for protecting against infection with *E. chaffeensis*.

The P30F proteins, particularly recombinant forms of P30, are immunogenic and are, thus, useful for preparing antibodies that are useful for immunolabeling isolates of *E. canis*. The P30 protein is also useful for diagnosing canine ehrlichiosis in mammals, particularly in members of the family Canidae, most particularly in dogs and for diagnosing infections with *E. chaffeensis* in humans. The P30F proteins are also useful immunogens for raising antibodies that reduce the level of infection in an immunized mammal that has been infected with *E. canis*. The P30F proteins are also useful in a vaccine for protecting animals against infection with *E. canis*.

In another aspect, the present invention provides a polypeptide, which comprises a fragment of the OMP1 protein, hereinafter referred to as "rOMP-1". The rOMP-1 polypeptide weighs approximately 31 kDa and comprises all but the first 5 amino acids of mature OMP-1 protein. The rOMP-1 polypeptide comprises the amino acid sequence extending from amino acid 6 through amino acid 251 of the amino acid sequence shown in FIG.1, (residues 26-281 of SEQ ID NO: 2). The present invention also embraces polypeptides where one or more of the amino acids in the sequence extending from amino acid 1 or 6 through amino acid 251 FIG. 1 are replaced by conservative amino acid residues. The present invention also relates to variant of rOMP-1 that have an amino acid sequence identity of at least 95%, more preferably at least 97%, and most preferably of at least 99% with the amino acid sequence extending from amino acid 6 through amino acid 251 of the OMP-1 protein and which derivative binds to antibodies in sera from humans infected with *E. chaffeensis*.

Polynucleotides

The present invention also provides isolated polynucleotides which encode the OMP proteins and the P30F proteins. The OMP-1 polynucleotide encodes the OMP-1 protein of *E. chaffeensis*, FIG. 3A shows one embodiment of the OMP-1 polynucleotide, SEQ ID NO: 1. The OMP-1B polynucleotide encodes the OMP-1B protein of *E. chaffeensis*; FIG. 4A shows one embodiment of the OMP-1B polynucleotide, SEQ ID NO: 3. The OMP-1C polynucleotide encodes the OMP-1C protein of *E. chaffeensis*, FIG. 5A shows one embodiment of the OMP-1C polynucleotide; SEQ ID NO: 5. The OMP-1D polynucleotide encodes the OMP-1D protein of *E. chaffeensis*; FIG. 6A shows one embodiment of the OMP-1D polynucleotide, SEQ ID NO: 7. The OMP-1E polynucleotide encodes the OMP-1E protein of *E. chaffeensis*; FIG. 7A shows one embodiment of the OMP-1E polynucleotide, SEQ ID NO: 9. The OMP-1F polynucleotide encodes the OMP-1F protein of *E. chaffeensis*; FIG. 8A shows one embodiment of the OMP-1F polynucleotide, SEQ ID NO: 11. The OMP-1A polynucleotide encodes the OMP-1A protein of *E. chaffeensis*; FIG. 9A shows one embodiment of the OMP-1A polynucleotide, SEQ ID NO: 13. The OMP-1R polynucleotide encodes the OMP-1R protein, FIG. 10A shows one embodiment of a portion of the OMP-1R polynucleotide, SEQ ID NO: 15. The OMP-1S polynucleotide encodes the OMP-1S protein of *E. chaffeensis*; FIG. 1A shows one embodiment of a portion of the OMP-1S polynucleotide, SEQ ID NO: 17. The OMP-1T polynucleotide encodes the OMP-1T protein of *E. chaffeensis*; FIG. 12A shows one embodiment of a portion of the OMP-1T polynucleotide, SEQ ID NO: 19. The OMP-1U polynucleotide encodes the OMP-1U protein of *E. chaffeensis*; FIG. 13A shows one embodiment of the OMP-1U polynucleotide, SEQ ID NO: 21. The OMP-1V polynucleotide encodes the OMP-1V protein of *E. chaffeensis*; FIG. 14A shows one embodiment of the OMP-1V polynucleotide, SEQ ID NO: 23. The OMP-1W polynucleotide encodes the OMP-1W protein of *E. chaffeensis*; FIG. 15A shows one embodiment of the OMP-1W polynucleotide, SEQ ID NO: 25. The OMP-1X polynucleotide encodes an OMP-1× protein of *E. chaffeensis*; FIG. 16A shows one embodiment of the OMP-1X polynucleotide, SEQ ID NO 27. The OMP-1Y polynucleotide encodes the OMP-1Y protein of *E. chaffeensis*; FIG. 17A shows one embodiment of the OMP-1Y polynucleotide, SEQ ID NO 29. The OMP-1Z polynucleotide encodes the OMP-1Z protein of *E. chaffeensis*; FIG. 18A shows one embodiment of an OMP-1Z polynucleotide encoding such polypeptide, SEQ ID NO: 49. The OMP-1H polynucleotide encodes the OMP-1H protein of *E. chaffeensis*; FIG. 33A shows one embodiment of a portion of the OMP-1H polynucleotide, SEQ ID NO: 51.

The p30 polynucleotide encodes the P30 protein of *E. canis*, FIG. 19A shows one embodiment of the p30 polynucleotide, SEQ ID NO: 31. The p30a polynucleotide encodes the P30a protein of *E. canis*, FIG. 20A shows one embodiment of the p30a polynucleotide, SEQ ID NO: 33. The p30-1 polynucleotide encodes the P30-1 protein of *E. canis*; FIG. 21A shows one embodiment of the p30-1 polynucleotide, SEQ ID NO: 35. The p30-2 polynucleotide encodes the P30-2 protein of *E. canis*; FIG. 22A shows one embodiment of the p30-2 polynucleotide, SEQ ID NO: 37. The p30-3 polynucleotide encodes the P30-3 protein of *E. canis*; FIG. 23A shows one embodiment of the p30-3 polynucleotide, SEQ ID NO: 39. The p30-4 polynucleotide encodes the P30-4 protein of *E. canis*, FIG. 24A shows one embodiment of the p30-4 polynucleotide, SEQ ID NO: 41. The p30-5 polynucleotide encodes the P30-5 protein of *E. canis*, FIG. 25A shows one embodiment of the $p3^{0-5}$ polynucleotide, SEQ ID NO: 43. The p30-6 polynucleotide encodes the P30-6 protein, FIG. 26A shows one embodiment of the p30-6 polynucleotide, SEQ ID NO: 53. The p30-7 polynucleotide encodes the P30-7 protein of *E. canis*; FIG. 27A shows one embodiment of the p30-7 polynucleotide, SEQ ID NO: 55. The p30-8 polynucleotide encodes the P30-8 protein of *E. canis*; FIG. 28A shows one embodiment of the p30-8 polynucleotide, SEQ ID NO: 45. The p30-9 polynucleotide encodes the P30-9 protein of *E. canis*; FIG. 29A shows one embodiment of a portion of the p30-9 polynucleotide, SEQ ID NO: 57. The p30-10 polynucleotide encodes the P30-10 protein of *E. canis*, FIG. 30A shows one embodiment of a portion of the p30-10 polynucleotide, SEQ ID NO: 47. The p30-11 polynucleotide encodes the P30-11 protein of *E. canis*; FIG. 31A shows one embodiment of a portion of the p30-11 polynucleotide, SEQ ID NO: 59. The p30-12 polynucleotide encodes the P30-12 protein of *E. canis*; FIG. 32A shows one embodiment of a portion of the p30-12 polynucleotide, SEQ ID NO: 61.

The polynucleotides are useful for producing the outer membrane proteins of *E. chaffeensis* and *E. canis*. For example, an RNA molecule encoding the outer membrane protein OMP-1 is used in a cell-free translation systems to prepare OMP-1. Alternatively, a DNA molecule encoding the outer membrane protein is introduced into an expression vector and used to transform cells. Suitable expression vectors include for example chromosomal, nonchromosomal and synthetic DNA sequences, e.g., derivatives of SV40, bacterial plasmids, phage DNAs; yeast plasmids, vectors derived from combinations of plasmids and phage DNAs, viral DNA such as vaccinia, adenovirus, fowl pox virus, and pseudorabies. The DNA sequence is introduced into the expression vector by conventional procedures.

Accordingly, the present invention also relates to recombinant constructs comprising one or more of the polynucleotide sequences. Suitable constructs include, for example, vectors, such as a plasmid, phagemid, or viral vector, into which a sequence that encodes the outer membrane protein has been inserted. In the expression vector, the DNA sequence which encodes the outer membrane protein is operatively linked to an expression control sequence, i.e., a promoter, which directs mRNA synthesis. Representative examples of such promoters, include the LTR or SV40 promoter, the *E. coli* lac or trp, the phage lambda PL promoter and other promoters known to control expression of genes in prokaryotic or eukaryotic cells or in viruses. The promoter may also be the natural promoter of the outer membrane protein coding sequence. The expression vector also contains a ribosome binding site for translation initiation and a transcription terminator. Preferably, the recombinant expression vectors also include an origin of replication and a selectable marker, such as for example, the ampicillin resistance gene of *E. coli* to permit selection of transformed cells, i.e. cells that are expressing the heterologous DNA sequences. The polynucleotide sequence encoding the outer membrane protein is incorporated into the vector in frame with translation initiation and termination sequences. Optionally, the sequence encodes a fusion outer membrane protein which includes an N-terminal or C-terminal peptide or tag that stabilizes or simplifies purification of the expressed recombinant product. Representative examples of such tags include sequences which encode a series of histidine residues, the Herpes simplex glycoprotein D, or glutathione S-transferase.

Polynucleotides encoding the OMP proteins and the P30F proteins are also useful for designing hybridization probes for isolating and identifying cDNA clones and genomic clones encoding the OMP proteins, the P30F proteins or allelic forms thereof. Such hybridization techniques are known to those of skill in the art. The sequences that encode the OMP proteins and the P30F proteins are also useful for designing primers for polymerase chain reaction (PCR), a technique useful for obtaining large quantities of cDNA molecules that encode the OMP proteins and the P30F proteins.

Also encompassed by the present invention, are single stranded polynucleotides, hereinafter referred to as antisense polynucleotides, having sequences which are complementary to the DNA and RNA sequences which encode the OMP proteins and the P30F proteins. The term complementary as used herein refers to the natural binding of the polynucleotides under permissive salt and temperature conditions by base pairing, The present invention also encompasses oligonucleotides that are used as primers in polymerase chain reaction (PCR) technologies to amplify transcripts of the genes which encode the OMP proteins, the P30F proteins or portions of such transcripts. Preferably, the primers comprise 18-30 nucleotides, more preferably 19-25 nucleotides. Preferably, the primers have a G+C content of 40% or greater. Such oligonucleotides are at least 98% complementary with a portion of the DNA strand, i.e., the sense strand, which encodes the OMP protein or the P30F protein, or a portion of its corresponding antisense strand. Preferably, the primer has at least 99% complementarity, more preferably 100% complementarity, with such sense strand or its corresponding antisense strand. Primers which are which have 100% complementarity with the antisense strand of a double-stranded DNA molecule which encodes an OMP protein or a P30F protein have a sequence which is identical to a sequence contained within the sense strand. The identity of primers which are 15 nucleotides in length and have full complementarity with a portion of the antisense strand of a double-stranded DNA molecule which encodes the OMP-1 protein is determined using the nucleotide sequence, SEQ ID NO:1, shown in FIG. 3A and described by the general formula a-b, where a is any integer between 1 to 843, where b is equal to a+14, and where both a and b correspond to the positions of nucleotide residues shown in SEQ ID NO:1.

The present invention also encompasses oligonucleotides that are useful as hybridization probes for detecting transcripts of the genes which encode the OMP proteins and P30F proteins or for mapping of the genes which encode the OMP proteins and P30F proteins. Preferably, such oligonucleotides comprise at least 210 nucleotides, more preferably at least 230, most preferably from about 210 to 280 nucleotides. Such hybridization probes have a sequence which is at least 90% complementary with a sequence contained within the sense strand of a DNA molecule which encodes each of OMP proteins and P30F proteins or with a sequence contained within its corresponding antisense strand. Such hybridization probes bind to the sense strand under stringent conditions. The term "stringent conditions" as used herein is the binding which occurs within a range from about Tm 5° C. (5° C. below the melting temperature Tm of the probe) to about 20° C. to 25° C. below Tm. The probes are used in Northern assays to detect transcripts of OMP and P30F homologous genes and in Southern assays to detect OMP and P30F homologous genes. The identity of probes which are 200 nucleotides in length and have full complementarity with a portion of the antisense strand of a double-stranded DNA molecule which encodes the OMP-1 protein is determined using the nucleotide sequence, SEQ ID NO: 1, shown in FIG. 3A and described by the general formula a-b, where a is any integer between 1 to 843, b is equal to a +200, and where both a and b correspond to the positions of nucleotide residues shown in SEQ ID NO: 1.

The present invention also encompasses isolated polynucleotides which are alleles of the genes which encode the OMP proteins and the P30F proteins. As used herein, an allele or allelic sequence is an alternative form of the gene which may result from one or more mutations in the sequences which encode the OMP proteins and P30F proteins. Such mutations typically arise from natural addition, deletion of substitution of nucleotides in the open reading frame sequences. Any gene may have none, one, or several allelic forms. Such alleles are identified using conventional techniques, such as for example screening libraries with probes having sequences identical to or complementary with one or more OMP or P30F polynucleotides.

The present invention also encompasses altered polynucleotides which encode OMP proteins and P30F proteins. Such alterations include deletions, additions, or substitutions. Such alterations may produce a silent change and result in an OMP protein or P30F protein having the same amino acid sequence as the OMP protein or P30F protein encoded by the unaltered polynucleotide. Such alterations may produce a nucleotide sequence possessing non-naturally occurring codons. For example, codons preferred by a particular prokaryotic or eucaryotic host may be incorporated into the nucleotide sequences shown in FIGS. 3-33 to increase the rate of expression of the proteins encoded by such sequences. Such alterations may also introduce new restriction sites into the sequence or result in the production of an OMP protein variant or P30F protein variant. Typically, such alterations are accomplished using site-directed mutagenesis.

Antibodies

In another aspect, the present invention relates to antibodies which are specific for and bind to at least one OMP protein or P30F protein. Such antibodies are useful research tools for identifying cells, particularly monocytes or macrophages, infected with *E. chaffeensis* or *E. canis* and for purifying the major outer membrane protein of *E. chaffeensis* or *E. canis* from partially purified preparations by affinity chromatography. Such antibodies are also useful for identifying bacterial colonies, particularly colonies of genetically-engineered bacteria, that are expressing the major outer membrane protein of *E. chaffeensis* or *E. canis*.

Kits

The present invention also relates to kits containing reagents for diagnosing *E. chaffeensis* and *E. canis*. The kit comprises one or more OMP proteins, or one or more *E. canis* proteins, or antigenic fragments thereof. For ease of detection, it is preferred that the OMP protein or P30F proteins be attached to a substrate such as a column, plastic dish, matrix, or membrane, preferably nitrocellulose. The kit may further comprise a biomolecule, preferably a secondary antibody, for detecting interactions between the isolated OMP protein or P30F protein and antibodies in a patient sample. Preferably, the biomolecule is coupled to a detectable tag such as an enzyme, chromophore, fluorophore, or radio-isotope. The kit is used by contacting a patient sample with the OMP protein or P30F protein under conditions that permit formation of antigen-antibody complexes. Then the biomolecule is added and the presence or absence of any resulting antigen-antibody complexes is detected by assaying for a change in the sample, for example, by observing the formation of a precipitate in the sample, the presence of radioactivity on the substrate, or a color change in the sample or on the substrate.

Diagnostic Method

The present invention also provides a method for detecting antibodies to the *E. chaffeensis* or *E. canis* in a sample of a bodily fluid from a patient. The method comprises providing an isolated outer membrane protein of *E. chaffeensis* or *E. canis*, particularly a recombinant form of the isolated protein, contacting the outer membrane protein or polypeptide with a sample taken from the patient; and assaying for the formation of a complex between the outer membrane protein or polypeptide and antibodies in the sample. For ease of detection, it is preferred that the isolated protein or polypeptide be attached to a substrate such as a column, plastic dish, matrix, or membrane, preferably nitrocellulose. The sample may be a tissue or a biological fluid, including urine, whole blood, or exudate, preferably serum. The sample may be untreated, subjected to precipitation, fractionation, separation, or purification before combining with the isolated protein or peptide. Interactions between antibodies in the sample and the isolated protein or peptide are detected by radiometric, colorimetric, or fluorometric means, size-separation, or precipitation. Preferably, detection of the antibody-outer membrane protein complex is by addition of a secondary antibody that is coupled to a detectable tag, such as for example, an enzyme, fluorophore, or chromophore. Formation of the complex is indicative of the presence of anti-E chaffeensis or anti-E canis antibodies, either IgM or IgG, in the patient. Thus, the method is used to determine whether a patient is infected with *E. chaffeensis* or *E. canis*.

Preferably, the method employs an enzyme-linked immunosorbent assay (ELISA) or a Western immunoblot procedure. Such methods are relatively simple to perform and do not require special equipment as long as membrane strips are coated with a high quality antigen. Accordingly, it is more advantageous to use a recombinant form of the outer membrane protein of *E. chaffeensis* or *E. canis* since such proteins, typically, are more pure and consistent in quality than a purified form of such protein.

Immunogenic Composition

The present invention also relates to immunogenic compositions comprising one or more OMP protein of *E. chaffeensis* and a pharmaceutically acceptable adjuvant and to immunogenic compositions comprising one or more P30F proteins of *E. canis* and a pharmaceutically acceptable adjuvant, which, preferably, enhances the immunogenic activity of the outer membrane protein in the host animal.

Preparing the OMP Proteins and the P30F Proteins

The OMP proteins and P30F proteins may be produced by conventional peptide synthesizers. The OMP proteins and P30F proteins may also be produced using cell-free translation systems and RNA molecules derived from DNA constructs that encode the OMP proteins and P30F proteins. Alternatively, OMP proteins and P30F proteins are made by transfecting host cells with expression vectors that comprise a DNA sequence that encodes the respective OMP protein or P30F protein and then inducing expression of the protein in the host cells. For recombinant production, recombinant constructs comprising one or more of the sequences which encode the OMP protein or P30F protein are introduced into host cells by conventional methods such as calcium phosphate transfection, DEAE-dextran mediated transfection, transvection, microinjection, cationic lipid-mediated transfection, electroporation, transduction, scrape lading, ballistic introduction or infection.

The OMP proteins or P30F proteins may be expressed in suitable host cells, such as for example, mammalian cells, yeast, bacteria, or other cells under the control of appropriate promoters using conventional techniques. Following transformation of the suitable host strain and growth of the host strain to an appropriate cell density, the cells are harvested by centrifugation, disrupted by physical or chemical means, and the resulting crude extract retained for further purification of the OMP protein or P30F protein.

Conventional procedures for isolating recombinant proteins from transformed host cells, such as isolation by initial extraction from cell pellets or from cell culture medium, followed by salting-out, and one or more chromatography steps, including aqueous ion exchange chromatography, size exclusion chromatography steps, and high performance liquid chromatography (HPLC), and affinity chromatography may be used to isolate recombinant OMP protein or P30F protein Preparation of Antibodies The OMP proteins, P30F proteins, and variants thereof are used as immunogens to produce antibodies immunospecific for one or more OMP protein or one or more P30F protein. The term "immunospecific" means the antibodies have substantially greater affinity for one or more OMP protein or P30F protein than for other proteins. Such antibodies may include, but are not limited to, polyclonal, monoclonal, chimeric, single chain, and Fab fragments.

Polyclonal antibodies are generated using conventional techniques by administering the OMP protein or P30F protein, or a chimeric molecule to a host animal. Depending on the host species, various adjuvants may be used to increase immunological response. Among adjuvants used in humans, BCG (*bacilli* Calmette-Guerin, and *Corynebacterium parvum* are especially preferable. Conventional protocols are also used to collect blood from the immunized animals and to isolate the serum and or the IgG fraction from the blood.

For preparation of monoclonal antibodies, conventional hybridoma techniques are used. Such antibodies are produced by continuous cell lines in culture. Suitable techniques for preparing monoclonal antibodies include, but are not limited to, the hybridoma technique, the human B-cell hybridoma technique, and the EBV hybridoma technique.

Various immunoassays may be used for screening to identify antibodies having the desired specificity. These include protocols which involve competitive binding or immunoradiometric assays and typically involve the measurement of complex formation between the respective OMP protein or P30F protein and the antibody.

Polynucleotides that Encode OMP Proteins and P30F Proteins

Polynucleotides comprising sequences encoding an OMP protein or P30F protein may be synthesized in whole or in part using chemical methods. Polynucleotides which encode an OMP protein or P30F protein, particularly alleles of the genes which encode an OMP protein or P30F protein, may be obtained by screening a genomic library of an *E. chaffeensis* or *E. canis* isolate with a probe comprising sequences identical or complementary to the sequences shown in FIGS. 3-33 or with antibodies immunospecific for a OMP protein or P30F protein to identify clones containing such polynucleotide.

Polynucleotides which Encode OMP-1 Protein and P30 Protein

A. Isolation of the Outer Membrane Proteins

*E. chaffeensis* Arkansas strain and *E. canis* Oklahoma strain were cultivated in the DH82 dog macrophage cell line and purified by Percoll density gradient centrifugation. Purified ehrlichiae (100 μg) were suspended with 10 mM sodium phosphate buffer, pH 7.4, containing 0.1% Sodium N-lauroyl sarcosine (Sarkosyl) [Sigma, St. Louis, Mo.], 50 μg/ml each DNase I (Sigma) and RNase A (Sigma), and 2.5 mM $MgCl_2$. After incubation at 37° for 30 min, the sample was separated by centrifugation at 10,000×g for 1 h into the soluble supernatant and the insoluble precipitate. The insoluble pellet was resuspended 2 to 3 times with 0.1% Sarkosyl and centrifuged. The final pellet was analyzed by sodium dodecyl sulfate (SDS)-polyacrylamide gel electrophoresis (PAGE) and by electron microscopy.

Transmission electron microscopy revealed that the purified ehrlichial fraction consists of a mixture of electron dense and light forms of *E. chaffeensis* with slight disintegration of inner membrane. Ehrlichiae were not surrounded with the host inclusion membrane. Various sizes of membrane vesicles (<1 μm) without significant ribosomes or nuclear materials were observed in the Sarkosyl-insoluble fraction from the organism. Succinic dehydrogenase (inner membrane marker enzyme of gram negative bacteria) activities were at less than the detection limit (1 n moles/min/mg of protein) in the Sarkosyl-insoluble fraction compared to approximately 10 n moles/min/mg of protein in the Percoll-purified organisms, suggesting that the insoluble fraction primarily consisted of the outer membrane of *E. chaffeensis.*

Analysis of the Sarkosyl-soluble, and insoluble fraction of *E. chaffeensis* by SDS-PAGE suggested that proteins of 30-kDa range in the insoluble fraction represent the major outer membrane proteins of this organism. Analysis of the Sarkosyl-soluble, and insoluble fraction of *E. canis* by SDS-PAGE suggested that proteins of 30-kDa range in the insoluble fraction represent the major outer membrane proteins of this organism also. *E. canis* was antigenically cross reactive with *E. chaffeensis*. These findings indicate that the 30-kDa range proteins represent the major outer membrane proteins of these two *Ehrlichia* spp.

To improve resolution of the outer membrane proteins, proteins in the Sarkosyl-insoluble pellet prepared from 400 μg of purified *E. chaffeensis* were separated by a reversed-discontinuous (Rd) SDS-PAGE (2.5-cm-long 17% gel on top of 11-cm-long 12% gel). At least five proteins of 30-kDa range in *E. chaffeensis* (P23, P25, P27, P28, and P29) were resolved from the Sarkosyl-insoluble proteins.

B. Cloning and Sequencing of the omp-1 Gene

The portion of the membrane containing bound proteins was excised and analyzed with an Applied Biosystems protein sequencer (Model 470). The N-terminal amino acid sequence of OMP-1 protein was determined as D P A G S G 1 N G N F Y I S G K Y M P, SEQ ID NO: 63. Based on 6th to 12th amino acids of this sequence, a forward primer, FECH1, having the sequence: 5'-CGGGATCCGAATTCGG(A/T/G/C)AT(A/T/C)AA(T/C)GG(A/T/G/C)AA(T/C)TT(T/C)TA-3'. SEQ ID NO:64 was designed. Amino acids at the 1 to 5 positions of the N terminus of OMP-1 were not included in this primer design. For insertion into an expression vector, a 14-bp sequence (underlined) was added at the 5' end of primer to create an EcOR1 and a BamHI site. The reverse primer, RECH2, which includes a NotI site at the 5' end for ligation into an expression vector had the sequence: 5'-AGCGGCCGCTTA(A/G)AA(T/C)A(C/G) (A/G)AA (C/T)CT T(C/G)C TCC-3'. SEQ ID NO:65.

Genomic DNA of *E. chaffeensis* was isolated from purified organisms. PCR amplification with FECH1 and RECH2 primers was performed using a Perkin-Elmer Cetus DNA Thermal Cycler (model 480). A 0.8-kb amplified product was cloned in the pCR11 vector of a TA closing kit, as described by the manufacturer (Invitrogen Co., San Diego, Calif.). The clone obtained was designated pCRIIp28. Both strands of the inserted DNA were sequenced by a dideoxy-termination method with an Applied Biosystems 373A DNA sequencer.

The 0.8-kb DNA fragment containing a partial OMP-1 gene, cloned in pCRIIp28, had an open reading frame (ORF) of 756 bp encoding a 251-amino acid recombinant protein (including both PCR primer regions) with a molecular mass of 27.2 kDa. The nucleotide sequence of the open reading frame, and the amino acid sequence of the polypeptide of the partial OMP-1 protein, are shown in FIG. 1.

A DNA fragment comprising the partial p30 gene was prepared in a similar manner, i.e., by PCR amplification of genomic DNA of *E. canis* using the forward primer, FECH1, which is described above, and a reverse primer, REC1, which is complimentary to the DNA sequence corresponding to amino acid positions 185 to 191 of the mature OMP-1 of *E. chaffeensis*. The sequence of REC1 is 5'-ACCTAACMCCTTGGTAAG-3', SEQ ID NO:66.

Genomic DNA of *E. canis* was isolated from the purified organism. PCR amplification was performed by using a Perkin-Elmer Cetus DNA Thermal Cycler (model 480). The 0.6-kb products were amplified with the FECHI-REC1 primer pair and were cloned into the pCRII vector of a TA cloning kit (Invitrogen Co., San Diego, Calif.). The clone obtained by the primer pair was designated pCRIIp30. Both strands of the insert DNA were sequenced by a dideoxy termination method with an Applied Biosystems 373 DNA sequencer.

The 0.6-kb DNA fragment containing a partial p30 gene cloned had an open reading frame (ORF) of 579 bp encoding a 193-amino-acid protein with a molecular mass of 21,175 Da. The partial P30 protein of *E. canis* was encoded by nucleotide 97 through nucleotide 672 of the sequence shown in FIG. 19A and comprised amino acid 33 through amino acid 224 of the sequence shown in FIG. 19B.

Polynucleotides which encode OMP 1A, OMP-1B, OMP-1C, OMP-1D, OMP-1F, and OMP1-E

A. Southern Blot Analysis.

Genomic DNA extracted from the purified *E. chaffeensis* (200 ng each) was digested with restriction endonucleases, electrophoresed, and transferred to Hybond-$N^+$ nylon membrane (Amersham, Arlington Heights, Ill.), by a standard method. The 0.8-kb p28 gene fragment from the clone pCRIIp28 was labeled with [$\alpha$-$^{32}$P]dATP by the random primer method using a kit (Boehringer Mannheim, Indianapolis, Ind.) and the labeled fragment was used as a DNA probe. Hybridization was performed at 60° C. in rapid hybridization buffer (Amersham) for 20 h. The nylon sheet was washed in 0.1×SSC (1×SSC containing 0.15M sodium chloride and 0.015M sodium citrate) with 1% SDS at 55° C. and the hybridized probes were exposed to Hyperfilm (Amersham) at −80° C.

Genomic Southern blot analysis with several restriction enzymes resulted in one or more DNA fragment(s) of *E. chaffeensis* which hybridized to $^{32}$P-labeled omp-1 gene probe. The restriction enzymes used did not cut within the p28 gene portion of the pCRIIp28 insert. Xba I, Bgl II, and Kpn I produced two bands, Spe I generated three bands, and EcOR V and Pst I produced multiple bands with different densities. EcOR I generated a broad band of 2.5 to 4 kb. These homologous genes are designated as omp-1 (outer membrane protein-1) family.

B. Cloning and Sequencing of Genomic Copies of *E. chaffeensis* omp-1 Gene.

Figure 2:
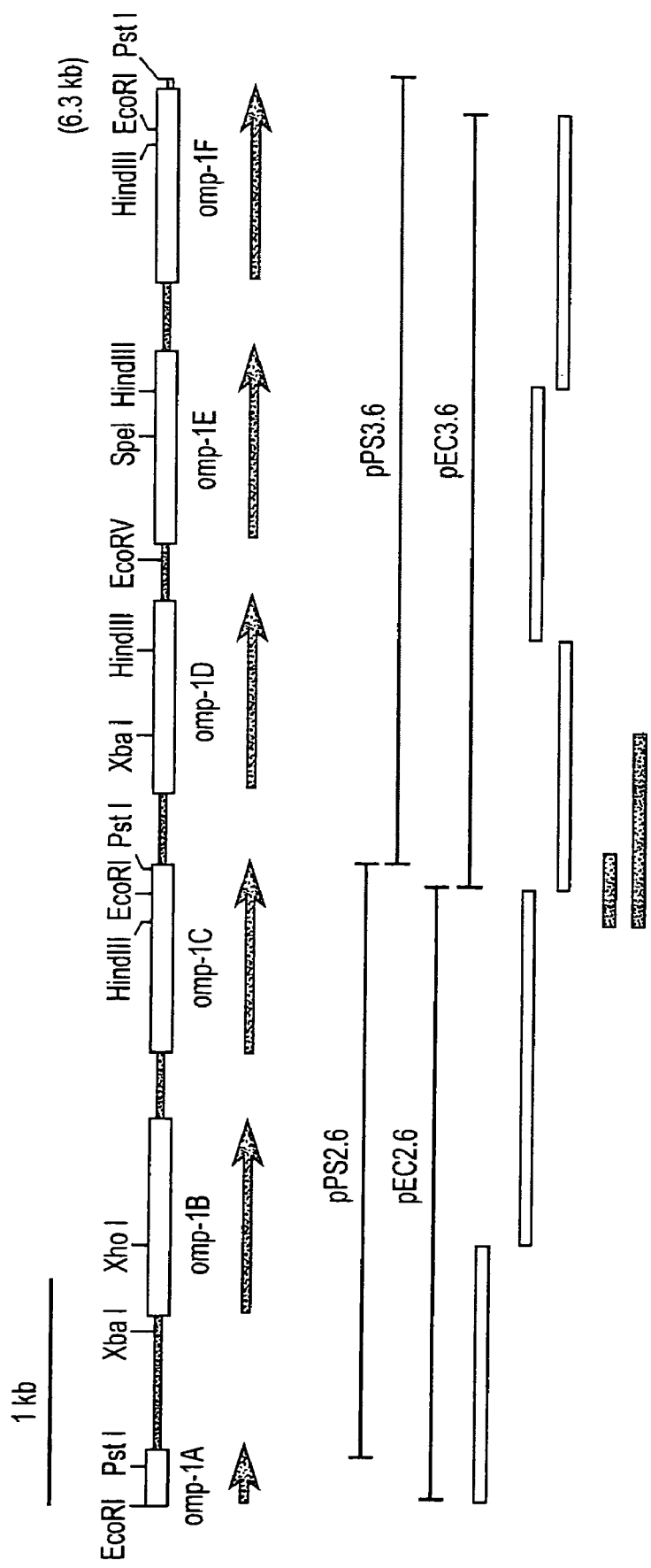

The EcOR I and Pst I fragments of DNA, detected by genomic Southern blot analysis as described above, were inserted into pBluescript II KS (+) vectors, and the recombinant plasmids were introduced into *E. coli* DH5a. Using the colony hybridization method with the $^{32}$P-labeled omp-1 gene probe, four positive clones were isolated from the transformant. The positive clones were designated pEC2.6, pEC3.6, pPS2.6, and pPS3.6. These contained the ehrlichial DNA fragments of 2.6-kb (EcOR I), 3.6 kb (EcOR I), 2.6 kb (Pst I), and 3.6 kb (Pst I), respectively. The inserts of the clones pEC3.6 and pPS2.6 overlapped as shown in FIG. 2. The overlapping area was further confirmed by PCR of *E. chaffeensis* genomic DNA with two pairs of primer sets interposing the junctions of the four clones. The 1.1- to 1.6-kb DNA fragments of HindIII-HindIII, HindIII-EcORI, or XhoI-EcORI in the pEC2.6 and pEC3.6 were subcloned for sequencing. DNA sequencing was performed with suitable synthetic primers by dideoxy-termination method as described above.

Four DNA fragments from 2.6 to 3.6 kb were cloned from the EcORI-digested and the PstI-digested genomic DNA of *E. chaffeensis* by colony hybridization with radiolabeled omp-1 gene probe. The inserted DNA of the two recombinant clones, pEC3.6 and PPS2.6, were overlapped. Sequencing revealed one 5'-truncated ORF of 243 bp (designated omp-1A) and five complete ORF of 836-861 bp (designated omp-1B to omp-1F), which are tandemly-arrayed and are homologous to the p28 gene (but are not identical), in the ehrlichial genomic DNA of 6,292 bp. The intergenic spaces were 581 bp between omp-1A and omp-1B and 260-308 bp among others. Putative promoter regions and ribosome-binding sites were identified in the noncoding regions.

C. Sequence Analysis and GenBank Accession Number.

Nucleotide sequences were analyzed with the DNASIS program (Hitachi Software Engineering Co., Ltd., Yokohama, Japan). A homology search was carried out with databases of the GenBank, Swiss Plot, PDB and PIR by using the software basic local alignment search tool in the BLAST network service (the National Center for Biotechnology Information, Bethesda, Md.). Phylogenetic analysis was performed by using the PHYLIP software package (version 3.5). An evolutional distance matrix, generated by using the Kimura formula in the PROTDIST, was used for construction of a phylogenetic tree by using the unweighted pair-group method analysis (UPGMA) (Felsenstein, J. 1989. PHYLIP-phylogeny inference package (version 3.3). Cladistics 5:164-166). The data were also examined using parsimony analysis (PROTPARS in PHYLIP). A bootstrap analysis was carried out to investigate the stability of randomly generated trees by using SEQBOOT and CONSENSE in the same package. The nucleotide sequence of the p28 gene and its gene copies has been assigned GenBank accession numbers U72291 and AF021338, respectively.

Proteins Encoded by the omp-1 Genes.

Five complete omp-1 gene copies (omp-1B to omp-1F) encode 279 to 287-amino acid proteins with molecular masses of 30,320-31,508 Da. The 25-amino acid sequence at the N-terminus of OMP-1B to OMP-1F (encoded in omp-1B to OMP-1F) is predicted to be a signal peptide because three carboxyl-terminal amino acids of the signal peptides (Ser-X-Ala in OMP-1B, Leu-X-Ser for OMP-C, and Ser-X-Ser for OMP-1D and OMP-1F) are included in the preferred amino acid sequence of signal peptidase at the processing sites proposed by Oliver. The calculated molecular masses of the mature OMP-1B to OMP-1F from the predicted amino acid sequences are 28,181 Da for OMP-1B, 27,581 Da for OMP-1C, 28,747 Da for OMP-1D, 27,776 Da for OMP-1E, and 27,933 Da for OMP-1F. The estimated isoelectric points are 4.76-5.76 in the mature OMP-1B to OMP-1F. An amino acid sequence in omp-1F gene (the 80th to 94th amino acids) was identical to the N-terminal amino acid sequences of *E. chaffeensis* native P23 protein as determined chemically, which indicates that P23 is derived from the OMP-1F gene.

Alignment of predicted amino acid sequences of the *E. chaffeensis* OMP-1 family and *Cowdria ruminantium*, revealed substitutions or deletions of one or several contiguous amino acid residues throughout the molecules. The significant differences in sequences among the aligned proteins are seen in the regions indicated SV (semivariable region) and HV (hypervariable region) 1 to 3 in FIG. 34. Computer analysis for hydropathy revealed that protein molecules predicted from all omp-1 gene copies contain alternative hydrophilic and hydrophobic motifs which are characteristic of transmembrane proteins. The HV1 and HV2 were found to locate in the hydrophilic regions.

The amino acid sequences of 5 mature proteins without signal peptides (OMP-1, and OMP-1C to OMP-1F) were sirmilar to one another (71-83%) but the sequence of OMP-1B was dissimilar to those of the 5 proteins (45-48%). The amino acid sequences of the 5 proteins showed an intermediate degree of similarity with that of *C. ruminantium* MAP-1 (59-63%), but the similarity between that of the OMP-1B and the *C. ruminantium* MAP-1 was low (45%). These relations are shown in a phylogenetic tree which was obtained based on the amino acid sequence alignment by UPGMA method in the PHYLIP software package. Three proteins (OMP-1, OMP-1D, and OMP-1F) and two proteins (OMP-1C and OMP-1E) formed two separate clusters. The OMP-1B was located distantly from these two clusters. The *C. ruminantium* MAP-1 was positioned between the OMP-1B and other members in the OMP-1 family.

Preparation of a Recombinant form of OMP-1 and P30

The 0.8-kb p28 gene from *E. chaffeensis* was excised from the clone pCRIIp28 by EcORI-NotI double-digestion, ligated into EcORI-NotI sites of a pET 29a expression vector, and amplified in *Escherichia coli* BL21 (DE3)pLysS (Novagen, Inc., Madison, Wis.). The clone (designated pET29p28) produced a fusion protein with a 35-amino acid sequence carried from the vector at the N terminus. The amino acid sequence of the OMP-1 portion of the fusion protein, referred to hereinafter as rOMP-1, is depicted in FIG. 1.

An expression vector comprising the p30 gene was used to prepare the recombinant form of P30. To prepare the expression vector, an 0.6-kb fragment was excised from the clone pCRIIp30 by EcOR1 digestion, ligated into EcOR1 site of a pET29a expression vector, and amplifed in *E. coli* BL21 (DE3)pLys (Novagen, Inc., Madison, Wis.). The clone (designated pET29p30) produced a fusion protein with a 35-amino-acid sequence and a 21-amino-acid sequence carried from the vector at the N and C termini, respectively. The fusion protein had an amino acid sequence consisting of 249-amino acid residues with a molecular mass of 27,316 Da. The amino acid sequence of the P30 portion of the fusion protein, referred to hereinafter as rP30, is amino acid 33 through amino acid 224 of the sequence shown in FIG. 19B.

Preparation of anti-rOMP1 Antibody

An rOMP-1 antigen was prepared by excising the gel band corresponding to the rOMP-1 protein in SDS-PAGE, mincing the band in phosphate-buffered saline (PBS), pH 7.4, and mixing with an equal volume of Freund's incomplete adjuvant (Sigrna). The rOMP-1 mixture (1 mg of protein each time) was subcutaneously injected into a rabbit every 2 weeks four times. A serum sample was collected from the rabbit to provide the anti-rOMP-1 antibody The anti-rOMP-1 antibody was examined by western immunoblot analysis. The results indicated that the rabbit anti-rOMP-1 antibody recognized not only rOMP-1 (31 kDa) and OMP-0.1 protein, but also P29 and P25 of *E. chaffeensis* and P30 of *E. canis*. These results indicate that OMP-1 shares antigenic epitopes with P25 and P29 in *E. chaffeensis* and P30 of *E. canis*.

The following examples are for purposes of illustration only and are not intended to limit the scope of the claims which are appended hereto.

EXAMPLE 1

Assaying for the Presence of Anti-OMP-1 Antibody in a Patient

Convalescent-phase serum from a patient with clinical signs of human ehrlichiosis was used. Western blot analyses using the rP28 protein as antigen was performed with 1:1,000 dilutions of this serum. Alkaline phosphatase-conjugated affinity-purified anti-human immunoglobulin G (Kirkegaard & Perry Laboratories, Inc., Gaithersburg, Md.) was used at a 1:1,000 or 1:2,000 dilution as secondary antibodies. Results indicated that serum from a patient with clinical signs of human ehrlichiosis reacted strongly to rOMP-1 protein (31 kDa).

EXAMPLE 2

Assaying for the Presence of Anti-OMP-1 Antibody in a Patient

Convalescent-phase serum from a patient with clinical signs of human ehrlichiosis was reacted with the rP30 protein of *E. canis* as described in Example 1. The serum reacted strongly to rP30. These results indicate the rP30 is useful for diagnosing an infection with *E. chaffeensis* in human patients.

EXAMPLE 3

Identifying *E. Chaffeensis*-Infected Cells Using Anti-rOMP-1 Antibody

*E. chaffeensis*-infected DH82 cells were sonicated and centrifuged at 400×g for 10 min. The supernatant was then centrifuged at 10,000×g for 10 min to obtain ehrlichia-enriched pellet. The pellet was resuspended and incubated with rabbit anti-rOMP-1 antibody or normal rabbit serum (1:100 dilution) at 37° C. for 1 h in PBS containing 1% bovine serum albumin (BSA-PBS). After washing, the ehrlichiae was incubated with gold-conjugated protein G (20 nm), Sigma) at 1:30 dilution for 1 h at room temperature in BSA-PBS. After washing again, the specimen was fixed with 1.25% formaldehyde, 2.5% glutaraldehyde, and 0.03% trinitrophenol in 0.1 M cacodylate buffer (pH 7.4) for 24h and postfixed in 1% osmium-1.5% potassium ferricyanide for 1 h (34). The section was then embedded in PolyBed 812 (Polysciences, Warraington, Pa.). The specimen was ultrathin sectioned at 60 nm, stained with uranyl acetate and lead citrate, and observed with a Philips 300 transmission electron microscope at 60 kV.

Transmission immunoelectron microscopy with colloidal gold-conjugated protein G and rabbit anti-rP28 antibody revealed gold particles bound to *E. chaffeensis* surface. The distribution of the particles was random, close to the surface, and appeared as if almost embedded in the membrane, suggesting that the antigenic epitope protrudes very little from the lipid bilayer. Nonetheless, the antigenic epitope was surface-exposed, and thus, could be recognized by rabbit anti-rOMP-1 antibody. No gold particles were observed on host cytoplasmic membrane or *E. chaffeensis* incubated with normal rabbit serum.

EXAMPLE 4

Immunization of Mice and *E. Chaffeensis* Challenge.

The rOMP-1 band in SDS-PAGE was excised, minced, and mixed with an equal volume of Freund's incomplete or complete adjuvant. Nine BALB/c male mice (6 weeks old) were divided into two groups. Five mice were intraperitoneally immunized a total of four times at 10-day intervals; twice with a mixture of the minced gel with the rOMP-1 (30 to 40 µg of protein per mouse each time) and incomplete adjuvant, and twice with a mixture of the recombinant protein (the same amount as before) and complete adjuvant. Four mice were intraperitoneally injected with a mixture of the minced gel without protein and the respective adjuvants. For ehrlichia-challenge, approximately 1×10$^7$ DH82 cells heavily-infected with *E. chaffeensis* were disrupted by sonication in serum-free DMEM (GIBCO-BRL) and centriftiged at 200×g for 5 min. The supernatant was diluted to a final volume of 5 ml, and 0.3 ml was inoculated intraperitoneally into each mouse 10 days after the last immunization. Before challenge, all 5-immunized mice had a titer of 1:160 against *E. chaffeensis* antigen by IFA and all 4-nonimmunized mice were negative.

At day 5 post-challenge, approximately 1 ml of blood was collected in an EDTA tube from each mouse and protection was assessed by PCR detection of *E. chaffeensis* 16S rDNA in the buffy coat of the collected blood. *E. chaffeensis* could not be reisolated in cell culture at day 10 postinfection. Day 5 post challenge is the optimum time at which establishment of ehrlichial infection can be examined by PCR without the influence of residual DNA from the ehrlichiae used as the challenge before the spontaneous clearance of organisms take place. The *E. chaffeensis*-specific DNA fragment was observed in all nonimmunized mice but not in any immunized mice, indicating that immunization of rOMP-1 apparently protects mice from ehrlichial infection and indicating that the OMP-1 is a potential protective antigen.

EXAMPLE 5

Assaying for the Presence of Anti-P30 Antibody in Dogs

The rP30 protein was used as an antigen in a Western immunoblot analysis and dot blot analysis to detect the presence of antibody to *E. canis* in serum from *E. canis* infected dogs. The results of the Western immunoblot analysis indicated that reactivity of the sera with rP30 was stronger than the reactivity that was observed when purified *E. canis* was used as antigen. The results of the dot blot assay indicated that rP30 is a useful and sensitive tool for serodiagnosis of canine ehrlichiosis.

What is claimed is:

1. An isolated or purified polypeptide comprising a sequence chosen from the following: a P30 protein, a variant of the P30 protein, an antigenic fragment of the P30 protein, wherein the P30 protein consists of SEQ ID NO. 32; a P30a protein, a variant of the P30a protein, an antigenic fragment of the P30a protein, wherein the P30a protein consists of SEQ ID NO. 34; a P30-1 protein, a variant of the p30-1 protein, an antigenic fragment of the P30-1 protein, wherein the P30-1 protein consists of SEQ ID NO. 36; a P30-2 protein, a variant of the P30-2 protein, an antigenic fragment of the P30-2 protein, wherein the P30-2 protein consists of SEQ ID NO. 38; a P30-3 protein, a variant of the P30-3 protein, an antigenic fragment of the P30-3 protein, wherein the P30-3 protein consists of SEQ ID NO. 40; a P30-4 protein, a variant of the P30-4 protein, an antigenic fragment of the P30-4 protein, wherein the P30-4 protein consists of SEQ ID NO. 42; a P30-5 protein, a variant of the P30-5 protein, an antigenic fragment of the P30-5 protein, wherein the P30-5 protein consists of SEQ ID NO. 44; a P30-6 protein, a variant of the P30-6 protein, an antigenic fragment of the P30-6 protein, wherein the P30-6 protein consists of SEQ ID NO. 54; a P30-7 protein, a variant of the P30-7 protein, an antigenic fragment of the P30-7 protein, wherein the P30-7 protein consists of SEQ ID NO. 56; a P30-8 protein, a variant of the P30-8 protein, an antigenic fragment of the P30-8 protein, wherein the P30-8 protein consists of SEQ ID NO. 46; a P30-9 protein, a variant of the P30-9 protein, an antigenic fragment of the P30-9 protein, wherein the P30-9 protein consists of SEQ ID NO. 58; a P30-10 protein, a variant of the P30-10 protein, an antigenic fragment of the P30-10 protein, wherein the P30-10 protein consists of SEQ ID NO. 48; a P30-11 protein, a variant of the P30-11 protein, an antigenic fragment of the P30-11 protein, wherein the P30-11 protein consists of SEQ ID NO. 60; a P30-12 protein, a variant of the P30-12 protein, and an antigenic fragment of the P30-12 protein, wherein the P30-12 protein consists of SEQ ID NO. 62; and wherein the variants or antigenic fragments of each said P30, P30a, P30-1, P30-2, P30-3, P30-4, P30-5, P30-6, P30-7, P30-8, P30-9, P30-10, P30-11, P30-12 protein are immunoreactive with at least one antibody that binds to their corresponding protein.

2. An isolated or purified polypeptide, wherein said polypeptide comprises a sequence that is at least 95% identical to an *E. canis* sequence chosen from: amino acid 26 through amino acid 288 of SEQ ID NO: 32, amino acid 26 through amino acid 287 of SEQ ID NO: 34, amino acid 55 through amino acid 307 of SEQ ID NO: 36, amino acid 26 through amino acid 280 of SEQ ID NO: 38, amino acid 26 through amino acid 283 of SEQ ID NO: 40, amino acid 26 through amino acid 276 of SEQ ID NO: 42, amino acid 27 through amino acid 293 of SEQ ID NO: 44, amino acid 31 through amino acid 293 of SEQ ID NO: 54, amino acid 31 through amino acid 296 of SEQ ID NO: 56, amino acid 27 through amino acid 299 of SEQ ID NO: 46, amino acid 27 through amino acid 281 of SEQ ID NO: 58, amino acid 26 through amino acid 280 of SEQ ID NO: 48, amino acid 26 through amino acid 279 of SEQ ID NO: 60, and amino acid 1 through amino acid 241 of SEQ ID NO: 62.

3. The isolated polypeptide of claim 1 wherein said polypeptide is the P30 protein, a variant of the P30 protein, or an antigenic fragment of the P30 protein.

4. An isolated polypeptide wherein said polypeptide comprises a sequence which is at least 95% identical to the sequence amino acid 33 through amino acid 224 of SEQ ID NO: 32.

5. The isolated polypeptide of claim 1, wherein said polypeptide is the P30a protein, a variant of the P30a protein, or an antigenic fragment of the P30a protein.

6. The isolated polypeptide of claim 1, wherein said polypeptide is the P30-1 protein, a variant of the P30-1 protein, or an antigenic fragment of the P30-1 protein.

7. The isolated polypeptide of claim 1, wherein said polypeptide is the P30-2 protein, a variant of the P30-2 protein, or an antigenic fragment of the P30-2 protein.

8. The isolated polypeptide of claim 1, wherein said polypeptide is the P30-3 protein, a variant of the P30-3 protein, or an antigenic fragment of the P30-3 protein.

9. The isolated polypeptide of claim 1, wherein said polypeptide is the P30-4 protein, a variant of the P30-4 protein, or an antigenic fragment of the P30-4 protein.

10. The isolated polypeptide of claim 1, wherein said polypeptide is the P30-5 protein, a variant of the P30-5 protein, or an antigenic fragment of the P30-5 protein.

11. The isolated polypeptide of claim 1, wherein said polypeptide is the P30-6 protein, a variant of the P30-6 protein, or an antigenic fragment of the P30-6 protein.

12. The isolated polypeptide of claim 1, wherein said polypeptide is the P30-7 protein, a variant of the P30-7 protein, or an antigenic fragment of the P30-7 protein.

13. The isolated polypeptide of claim 1, wherein said polypeptide is the P30-8 protein, a variant of the P30-8 protein, or an antigenic fragment of the P30-8 protein.

14. The isolated polypeptide of claim 1, wherein said polypeptide is the P30-9 protein, a variant of the P30-9 protein, or an antigenic fragment of the P30-9 protein.

15. The isolated polypeptide of claim 1, wherein said polypeptide is the P30-10 protein, a variant of the P30-10 protein, or an antigenic fragment of the P30-10 protein.

16. The isolated polypeptide of claim 1, wherein said polypeptide is the P30-11 protein, a variant of the P30-11 protein, or an antigenic fragment of the P30-11 protein.

17. The isolated polypeptide of claim 1, wherein said polypeptide is the P30-12 protein, a variant of the P30-12 protein, or an antigenic fragment of the P30-12 protein.

18. The isolated or purified polypeptide of claim 2, wherein said polypeptide comprises a sequence that is 100% identical to an *E. canis* sequence chosen from: amino acid 26 through amino acid 288 of SEQ ID NO: 32, amino acid 26 through amino acid 287 of SEQ ID NO: 34, amino acid 55 through amino acid 307 of SEQ ID NO: 36, amino acid 26 through amino acid 280 of SEQ ID NO: 38, amino acid 26 through amino acid 283 of SEQ ID NO: 40, amino acid 26 through amino acid 276 of SEQ ID NO: 42, amino acid 27 through amino acid 293 of SEQ ID NO: 44, amino acid 31 through amino acid 293 of SEQ ID NO: 54, amino acid 31 through amino acid 296 of SEQ ID NO: 56, amino acid 27 through amino acid 299 of SEQ ID NO: 46, amino acid 27 through amino acid 281 of SEQ ID NO: 58, amino acid 26 through amino acid 280 of SEQ ID NO: 48, amino acid 26 through amino acid 279 of SEQ ID NO: 60, and amino acid 1 through amino acid 241 of SEQ ID NO: 62.

19. The isolated or purified polypeptide of claim 18, wherein said polypeptide comprises a sequence that is 100% identical to the sequence amino acid 26 through amino acid 288 of SEQ ID NO: 32.

20. The isolated or purified polypeptide of claim 18, wherein said polypeptide comprises a sequence that is 100% identical to the sequence amino acid amino acid 26 through amino acid 287 of SEQ ID NO: 34.

21. The isolated or purified polypeptide of claim 18, wherein said polypeptide comprises a sequence that is 100% identical to the sequence amino acid 55 through amino acid 307 of SEQ ID NO: 36.

22. The isolated or purified polypeptide of claim 18, wherein said polypeptide comprises a sequence that is 100% identical to the sequence amino acid 26 through amino acid 280 of SEQ ID NO: 38.

23. The isolated or purified polypeptide of claim 18, wherein said polypeptide comprises a sequence that is 100% identical to the sequence amino acid 26 through amino acid 283 of SEQ ID NO: 40.

24. The isolated or purified polypeptide of claim 18, wherein said polypeptide comprises a sequence that is 100% identical to the sequence amino acid 26 through amino acid 276 of SEQ ID NO: 42.

25. The isolated or purified polypeptide of claim 18, wherein said polypeptide comprises a sequence that is 100% identical to the sequence amino acid 27 through amino acid 293 of SEQ ID NO: 44.

26. The isolated or purified polypeptide of claim 18, wherein said polypeptide comprises a sequence that is 100% identical to the sequence amino acid 31 through amino acid 293 of SEQ ID NO: 54.

27. The isolated or purified polypeptide of claim 18, wherein said polypeptide comprises a sequence that is 100% identical to the sequence amino acid 31 through amino acid 296 of SEQ ID NO: 56.

28. The isolated or purified polypeptide of claim 18, wherein said polypeptide comprises a sequence that is 100% identical to the sequence amino acid 27 through amino acid 299 of SEQ ID NO: 46.

29. The isolated or purified polypeptide of claim 18, wherein said polypeptide comprises a sequence that is 100% identical to the sequence amino acid 27 through amino acid 281 of SEQ ID NO: 58.

30. The isolated or purified polypeptide of claim 18, wherein said polypeptide comprises a sequence that is 100% identical to the sequence amino acid 26 through amino acid 280 of SEQ ID NO: 48.

31. The isolated or purified polypeptide of claim 18, wherein said polypeptide comprises a sequence that is 100% identical to the sequence amino acid 26 through amino acid 279 of SEQ ID NO: 60.

32. The isolated or purified polypeptide of claim 18, wherein said polypeptide comprises a sequence that is 100% identical to the sequence amino acid 1 through amino acid 241 of SEQ ID NO: 62.

* * * * *

UNITED STATES PATENT AND TRADEMARK OFFICE
CERTIFICATE OF CORRECTION

PATENT NO.         : 7,888,491 B2
APPLICATION NO.    : 10/901714
DATED              : February 15, 2011
INVENTOR(S)        : Yasuko Rikihisa et al.

It is certified that error appears in the above-identified patent and that said Letters Patent is hereby corrected as shown below:

In the Specification

Column 1, Lines 13-15, cancel the text beginning with "This work was supported" to and ending "certain rights in this invention." and insert the following language:
--This invention was made with government support under AI033123 and AI040934 awarded by the National Institutes of Health. The government has certain rights in the invention.--

Signed and Sealed this
Thirtieth Day of October, 2018

Andrei Iancu
*Director of the United States Patent and Trademark Office*

UNITED STATES PATENT AND TRADEMARK OFFICE
CERTIFICATE OF CORRECTION

PATENT NO. : 7,888,491 B2
APPLICATION NO. : 10/901714
DATED : February 15, 2011
INVENTOR(S) : Yasuko Rikihisa and Norio Ohashi It is certified that error appears in the above-identified patent and that said Letters Patent is hereby corrected as shown below:

In the Specification

Column 1, Lines 13-15 replace the Government Support Clause with:
--This invention was made with government support under grant number AI033123 awarded by the National Institutes of Health. The government has certain rights in the invention.--

This certificate supersedes the Certificate of Correction issued October 30, 2018.

Signed and Sealed this
Twenty-fifth Day of August, 2020

Andrei Iancu
*Director of the United States Patent and Trademark Office*